United States Patent
Brown et al.

(10) Patent No.: US 10,407,467 B2
(45) Date of Patent: Sep. 10, 2019

(54) POLYMYXIN DERIVATIVES AND THEIR USE IN COMBINATION THERAPY TOGETHER WITH DIFFERENT ANTIBIOTICS

(71) Applicant: New Pharma Licence Holdings Limited, Valletta (MT)

(72) Inventors: Pamela Brown, Reading (GB); Michael Dawson, Reading (GB); Mona Simonovic, Reading (GB); Steven Boakes, Reading (GB); Esther Duperchy, Reading (GB)

(73) Assignee: NEW PHARMA LICENCE HOLDINGS LIMITED, Valletta (MT)

( * ) Notice: Subject to any disclaimer, the term of this patent is extended or adjusted under 35 U.S.C. 154(b) by 0 days.

(21) Appl. No.: 14/892,757

(22) PCT Filed: May 21, 2014

(86) PCT No.: PCT/GB2014/051547
§ 371 (c)(1),
(2) Date: Nov. 20, 2015

(87) PCT Pub. No.: WO2014/188178
PCT Pub. Date: Nov. 27, 2014

(65) Prior Publication Data
US 2016/0222061 A1  Aug. 4, 2016

(30) Foreign Application Priority Data

May 22, 2013 (GB) .................................. 1309248.1
Mar. 11, 2014 (GB) .................................. 1404301.2

(51) Int. Cl.
| | |
|---|---|
| *C07K 7/62* | (2006.01) |
| *A61K 31/407* | (2006.01) |
| *A61K 38/00* | (2006.01) |
| *A61K 31/427* | (2006.01) |
| *A61K 31/431* | (2006.01) |
| *A61K 31/496* | (2006.01) |
| *A61K 31/575* | (2006.01) |
| *A61K 31/65* | (2006.01) |
| *A61K 31/7048* | (2006.01) |
| *A61K 31/7052* | (2006.01) |
| *A61K 38/08* | (2019.01) |

(52) U.S. Cl.
CPC .............. *C07K 7/62* (2013.01); *A61K 31/407* (2013.01); *A61K 31/427* (2013.01); *A61K 31/431* (2013.01); *A61K 31/496* (2013.01); *A61K 31/575* (2013.01); *A61K 31/65* (2013.01); *A61K 31/7048* (2013.01); *A61K 31/7052* (2013.01); *A61K 38/08* (2013.01); *A61K 38/00* (2013.01)

(58) Field of Classification Search
CPC ........... A61K 38/12; A61K 38/00; C07K 7/62
See application file for complete search history.

(56) References Cited

U.S. PATENT DOCUMENTS

| | | |
|---|---|---|
| 5,565,423 A | 10/1996 | Sandow et al. |
| 5,767,068 A | 6/1998 | VanDevanter et al. |
| 8,343,912 B2 | 1/2013 | Leese |
| 8,415,307 B1 | 4/2013 | Curran et al. |
| 2001/0021697 A1 | 9/2001 | Lowenstein et al. |
| 2008/0207874 A1 | 8/2008 | Leese et al. |
| 2008/0279820 A1 | 11/2008 | Hicks et al. |
| 2009/0215677 A1 | 8/2009 | Vaara et al. |
| 2009/0239792 A1 | 9/2009 | Vaara et al. |

(Continued)

FOREIGN PATENT DOCUMENTS

| | | |
|---|---|---|
| CN | 101851270 A | 10/2010 |
| EP | 0571921 A2 | 12/1993 |

(Continued)

OTHER PUBLICATIONS

Bergen et al., "Pharmacokinetics and pharmacodynamics of 'old' polymyxins: what is new?" Diagnostic Microbiology and Infectious Disease, 74: 213-223 (2012).
International Search Report and Written Opinion issued in International Patent Application No. PCT/GB2014/051547 dated Dec. 8, 2014.
Kanazawa et al., "Contribution of Each Amino Acid Residue in Polymyxin B3 to Antimicrobial and Lipopolysaccharide Binding Activity," Chemical & Pharmaceutical Bulletin, 57: 240-244 (2009).
Search Report issued in Great Britain Patent Application No. 1404301.2 dated Dec. 8, 2014.

(Continued)

*Primary Examiner* — Kaipeen E Yang
(74) *Attorney, Agent, or Firm* — Cantor Colburn LLP

(57) ABSTRACT

Described are compounds of formula (I) for use in combination treatment with a second active agent, such as rifampicin, for example for treatment of a microbial infection. The compound of formula (I) is a polymyxin compound is:

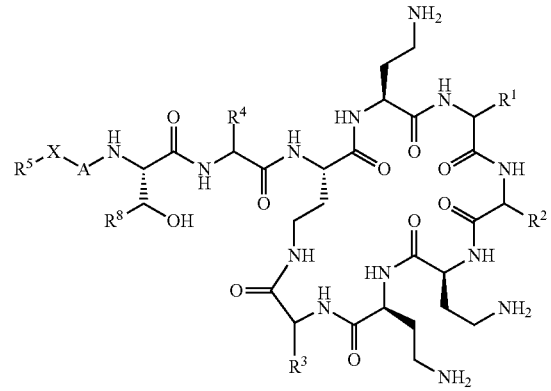

where the groups -A-, $-R^1$, $-R^2$, $-R^3$, $-R^4$, $-R^5$, $-R^6$, $-R^7$, $-R^8$, and $-X-$ are described in detail within the description.

25 Claims, 3 Drawing Sheets

(56) References Cited

U.S. PATENT DOCUMENTS

2010/0160215 A1 6/2010 Leese
2012/0316105 A1 12/2012 Magee et al.

FOREIGN PATENT DOCUMENTS

| | | |
|---|---|---|
| GB | 2128617 A | 5/1984 |
| WO | 88/00950 A2 | 2/1988 |
| WO | 2008/017734 A1 | 2/2008 |
| WO | 2009/098357 A1 | 8/2009 |
| WO | 2010/029196 A1 | 3/2010 |
| WO | 2010/075416 A1 | 7/2010 |
| WO | 2010/130007 A1 | 11/2010 |
| WO | 2012/051663 A1 | 4/2012 |
| WO | 2012/168820 A1 | 12/2012 |
| WO | 2013/072695 A1 | 5/2013 |
| WO | 2014/188178 A1 | 11/2014 |
| WO | 2015/149131 A1 | 10/2015 |

OTHER PUBLICATIONS

Sigma-Aldrich, "ChemFiles: Peptide Synthesis," 4: 1-19 (2007).
Tsubery et al., "Modulation of the Hydrophobic Domain of Polymyxin B Nonapeptide: Effect on Outer-Membrane Permeabilization and Lipopolysaccharide Neutralization," Molecular Pharmacology, 62: 1036-1042 (2002).
Velkov et al., "Teaching 'Old' Polymyxins New Tricks: New-Generation Lipopeptides Targeting Gram-Negative 'Superbugs'," ACS Chemical Biology, 9: 1172-1177 (2014).
Tsubery et al., "N-terminal modifications of Polymyxin B nonapeptide and their effect on antibacterial activity," Peptides, 22: 1675-1681 (2001).
Bergen et al., "Colistin Methanesulfonate is an Inactive Prodrug of Colistin against Pseudomonas aeruginosa," Antimicrobial Agents and Chemotherapy, 50: 1953-1958 (2006).
Chemical Abstracts Service Search Results, cited in search report issued in related Great Britain patent application dated Nov. 20, 2013.
De Visser et al., "Solid-phase synthesis of polymyxin B1 and analogues via a safety-catch approach," Journal of Peptide Research, 61: 298-306 (2003).
Diaz et al., "Fast and Efficient Access to a Family of Multifunctional 1,3,5-Trisubstituted Piperidines," Synthetic Communications, 38: 2799-2813 (2008).
Gallou et al., "Practical Synthesis of Unsymmetrical Ureas from Isopropenyl Carbamates," Journal of Organic Chemistry, 70: 6960-6963 (2005).
Katsuma et al., "Antimicrobial Activity of Des-Fatty Acyl-Polymyxin B Decapeptide N-Terminal Analogs," Peptide Science, 41: 549-550 (2005).
Katsuma et al., "Development of Des-Fatty Acyl-Polymyxin B Decapeptide Analogs with Pseudomonas aeruginosa-Specific Antimicrobial Activity," Chemical and Pharmaceutical Bulletin, 57: 332-336 (2009).
Kimura et al., "Polymyxin B Octapeptide and Polymyxin B Heptapeptide are Potent Outer Membrane Permeability Increasing Agents," Journal of Antibiotics, 45: 742-749 (1992).
Li et al., "Use of High-Performance Liquid Chromatography to Study the Pharmacokinetics of Colistin Sulfate in Rats Following Intravenous Administration," Antimicrobial Agents and Chemotherapy, 47: 1766-1770 (2003).
Magee et al., "Discovery of Dap-3 Polymyxin Analogs for the Treatment of Multidrug-Resistant Gram-negative Nosocomial Infections," Journal of Medicinal Chemistry, 56: 5079-5093 (2013).
O'Dowd et al., "Preparation of tetra-Boc-protected polymyxin B nonapeptide," Tetrahedron Letters, 48: 2003-2005 (2007).
Okimura et al., "Antimicrobial Activity of Various Aminocyclohexylcarbonyl-polymyxin B(2-10) Derivatives," Peptide Science, 45: 243-244 (2009).
Okimura et al., "Chemical Conversion of Natural Polymyxin B and Colistin to Their N-Terminal Derivatives," Bulletin of the Chemical Society of Japan, 80: 543-552 (2007).
Petrosillo et al., "Colistin monotherapy vs. combination therapy: evidence from microbiological, animal and clinical studies," Clinical Microbiology and Infection, 14: 816-827 (2008).
Quale et al., "Activity of Polymyxin B and the Novel Polymyxin Analogue CB-182,804 Against Contemporary Gram-Negative Pathogens in New York City," Microbial Drug Resistance, 18: 132-136 (2012).
Sato et al., "Des-Fatty Acyl-Polymyxin B Decapeptide Analogs with Antimicrobial Activity Specifically against Pseudomonas aeruginosa," Peptide Science, 44: 307-308 (2008).
Sato et al., "Novel Des-Fatty Acyl-Polymyxin B Derivatives with Pseudomonas aeruginosa-Specific Antimicrobial Activity," Chemical and Pharmaceutical Bulletin, 95: 597-602 (2011).
Shechter et al., "N-[(2-SUlfo)-9-fluorenylmethoxycarbonyl]3-gentamicin C1 Is a Long-Acting Prodrug Derivative," Journal of Medicinal Chemistry, 45: 4264-4270 (2002).
Vaara et al., "Novel Polymyxin Derivatives Carrying Only Three Positive Charges Are Effective Antibacterial Agents," Antimicrobial Agents and Chemotherapy, 52: 3229-3236 (2008).
Vaara et al., "A Novel Polymyxin Derivative That Lacks the Fatty Acid Tail and Carries Only Three Positive Charges Has Strong Synergism with Agents Excluded by the Intact Outer Membrane," Antimicrobial Agents and Chemotherapy, 54: 3341-3346 (2010).
Vaara et al., "Susceptibility of carbapenemase-producing strains of Klebsiella pneumoniae and Escherichia coli to the direct antibacterial activity of NAB739 and to the synergistic activity of NAB7061 with rifampicin and clarithromycin," Journal of Antimicrobial Chemotherapy, 65: 942-945 (2010).
Vaara, "Agents That Increase the Permeability of the Outer Membrane," Microbiological Reviews, 56: 395-411 (1992).
Voitenko et al., "Relationship between structure and histamine releasing action of polymyxin B and its analogues," Agents and Actions, 30: 153-156 (1990).
Weinstein et al., "Selective Chemical Modifications of Polymyxin B," Bioorganic & Medicinal Chemistry Letters, 8: 3391-3396 (1998).
Yamada et al., "Facile synthesis of N-alpha-protected-I-alpha, gamma-diaminobutyric acids mediated by polymer-supported hypervalent iodine reagent in water," Journal of Peptide Research, 64: 43-50 (2004).
Yousef et al., "Melatonin Attenuates Colistin-Induced Nephrotoxicity in Rats," Antimicrobial Agents and Chemotherapy, 55: 4044-4049 (2011).
International Search Report and Written Opinion issued in related PCT/GB2012/052844 dated Feb. 11, 2013.
Search Report issued in related Great Britain Patent Application No. GB1309248.1 dated Nov. 11, 2013.
Office Action dated May 12, 2016 by the Taiwan Intellectual Property Office in Taiwan Application No. 101142961.
International Search Report and Written Opinion dated Apr. 19, 2016 in International Application No. PCT/EP2015/077821.
Office Action dated Nov. 24, 2015 by the State Intellectual Property Office of China in Chinese Application No. 201280055987.6.
Gallardo-Godoy et al., "Activity and Predicted Nephrotoxicity of Synthetic Antibiotics Based on Polymyxin B", Journal of Medicinal Chemistry, 59:1068-1077 (2016).
International Search Report and Written Opinion issued in International Patent Application PCT/GB2014/051547 dated Dec. 8, 2014.
Examination Report issued in Eurasian Patent Application No. 201490634 dated Jun. 3, 2015.
Examination Report issued in Eurasian Patent Application No. 201490634 dated Oct. 12, 2015.
Examination Report issued in European Patent Application No. 12797961.5 dated Jun. 1, 2015.
Search Report issued in Great Britain Patent Application No. 1421019.9 dated Aug. 21, 2015.
Search Report issued in Great Britain Patent Application No. 1421020.7 dated Aug. 24, 2015.

(56) References Cited

OTHER PUBLICATIONS

International Search Report and Written Opinion issued in International Patent Application No. PCT/EP2015/055046 dated Jul. 10, 2015.
Examination Report issued in Colombian Patent Application No. 14-128978 dated Oct. 16, 2015.
Kato et al., "The Structure of Octapeptin D (Studies on Antibiotics from the Genus Bacillus. XXVIII)," Journal of Antibiotics, 33: 186-191 (1980).
Kline et al., "Synthesis and characterization of the colistin peptide polymyxin E1 and related antimicrobial peptides,"—Journal of Peptide Research, 57: 175-187 (2001).
Shoji et al., "The Structure of Polymyxin T1 (Studies on Antibiotics from teh Genus Bacillus. XXII)," Journal of Antibiotics, 30: 1042-1048 (1977).
Velkov et al., "Structure-Activity Relationships of Polymyxin Antibiotics," Journal of Medicinal Chemistry, 53: 1898-1916 (2010).

POLYMYXIN DERIVATIVES AND THEIR USE IN COMBINATION THERAPY TOGETHER WITH DIFFERENT ANTIBIOTICS

RELATED APPLICATIONS

The present case claims the priority of and benefit of GB 1309248.1 filed 22 May 2013 and GB 1404301.2 filed 11 Mar. 2014, the contents of both of which are hereby incorporated by reference in their entirety.

FIELD OF THE INVENTION

The present invention relates to novel compounds, combinations of compounds, pharmaceutical compositions comprising the compounds and the use of the compounds, pharmaceutical compositions and combinations for treatment, for example treatment of microbial infections, particularly by Gram-negative bacteria.

BACKGROUND

In susceptible individuals, certain Gram-negative bacteria such as *Escherichia coli, Klebsiella pneumoniae, Pseudomonas aeruginosa* and *Acinetobacter baumanii* can cause serious infections, such as pneumonia, urinary tract infections, skin and skin structure infections such as wound infections, ear infections, eye infections, intra-abdominal infections, bacterial overgrowth in the gastrointestinal tract and bacteraemia/sepsis. The treatment of serious bacterial infections in clinical practice can be complicated by antibiotic resistance. Recent years have seen a rise in infections by Gram-negative bacteria which are resistant to many types of antimicrobials including broad spectrum antibiotics such as aminoglycosides, cephalosporins and even carbapenems. There is therefore a need to identify new antimicrobials that are effective against Gram-negative bacteria, in particular against multidrug resistant Gram-negative bacteria.

Polymyxins are a class of antibiotics produced by the Gram-positive bacterium *Bacillus polymyxa*. First identified in the late 1940s, polymyxins, particularly polymyxin B and polymyxin E (colistin, usually as its prodrug colistin methane sulphonate) were used in the treatment of Gram-negative infections. However, these antibiotics exhibited side effects such as neurotoxicity and nephrotoxicity. Nevertheless the polymyxins now play an important role in the therapy of MDR Gram-negative infections due to the lack of viable alternatives. However, their use in therapy is limited to treatment of last resort.

WO 2008/017734 tries to address this toxicity problem by providing polymyxin derivatives carrying at least two but no more than three positive charges. These compounds are said to be effective antibacterial agents with reduced renal toxicity. It is hypothesised in the disclosure that the reduced number of positive charges decreases the affinity of the compound for isolated rat kidney tissue which in turn may lead to a reduction in nephrotoxicity.

Certain des-fatty acyl polymyxin derivatives have also been disclosed with reduced acute toxicity in mice whilst retaining good activity against pseudomonads (Katsuma et al. Chem. Pharm. Bull. 2009; 57, 332-336; Sato et al. Chem. Pharm. Bull. 2011; 59, 597-602). The compounds were significantly less active than polymyxin B against *E. coli* and *K. pneumoniae*.

WO 2010/075416 provides urea linked aryl polymyxin decapeptides including CB182,804, which is reported to have similar activity but reduced renal toxicity compared with polymyxin B. Phenyl cyclopropane polymyxin derivatives are also described in U.S. Pat. No. 8,415,307. These compounds are shown to have similar or reduced activity compared with polymyxin B.

WO 2012/168820 provides a further series of polymyxin derivatives reported to have reduced toxicity, and sometimes enhanced activity compared with polymyxin B, in which the diaminobutyrate group at position 3 in the tripeptide side chain is replaced by a diaminopropionate moiety.

Antibiotics are often used in combination for the treatment of infections for a number of reasons:
  To broaden coverage of pathogens for empiric therapy or for treatment of mixed infections
  To improve efficacy where the combination is more active than either antibiotic alone (additive) or more active than would be expected by simply summing the activity of the two antibiotics (synergistic)
  To suppress resistance development Indeed polymyxins are sometimes used in combination with other antibiotics (such as rifampicin, carbapenems, aminoglycosides or quinolones) for treatment of serious infections in the clinic for all of these reasons. Numerous microbiological and animal efficacy studies have been carried out on polymyxin-antibiotic combinations (Petrosillo et al. Clin. Microbiol. Infect. 2008; 14, 816-827). Combinations of polymyxins e.g. with neomycin and bacitracin are also available for topical use. Polymyxins act on the outer membrane of Gram-negative bacteria and are believed to facilitate the uptake of antibiotics which are less capable to cross the outer membrane barrier and hence enhance their activity.

As well as the use of polymyxins per se in combination, it has been reported that des fattyacyl polymyxin derivatives such as polymyxin B nonapeptide (PMBN), although not having very potent antibacterial activity, are still able to enhance the activity of antibiotics whose uptake is hindered by the outer membrane (Vaara et al. Microbiol. Rev. 1992; 56, 395-411). PMBN has reduced acute toxicity compared with polymyxin itself though it is unclear as to whether renal toxicity is reduced.

The use of less toxic 'permeabilisers' in combination with a second antibiotic would seem to offer the potential for therapeutic preparations with potent activity and reduced toxicity.

Despite this approach having been considered for some years such preparations have not been brought into medical use because they do not offer sufficient improvements over available therapies. Notably, their activity often falls short of that of the analogous polymyxin-antibiotic combination.

The compounds of WO 2008/017734 have been tested in combination with rifampicin, clarithromycin and other antibiotics and show some synergistic activity.

WO 2009/098357 provides polymyxin derivatives having no more than three positive charges, such as described in WO2008/017734, but with short acyl chains. These derivatives have poor intrinsic antimicrobial activity but are capable of potentiating the activity of the other agents.

CB-182,804 in the presence of rifampicin shows $MIC_{90}$ values equivalent or better than for polymyxin B plus rifampicin against *E. coli* and *K. pneumoniae* strains, but this compound is not quite as good against *A. baumanii* or *P. aeruginosa* strains (Quale et al. Microb. Drug Resist. 2012; 18, 132-136).

Activity of the desfatty acyl derivatives of Katsuma et al. and Sato et al. has not been reported in the presence of other antibiotics and neither have the compounds of WO 2012/168820 or U.S. Pat. No. 8,415,307.

There remains a need for less toxic polymyxin derivatives with strong potentiating activity for other antibiotics, and for combinations of such agents with partner antibiotics which offer therapeutic preparations with consistently potent activity across the target pathogens. Such compounds should also have an acceptable toxicity.

The present inventors have previously described in PCT/GB2012/052844, TW 101142961 and GCC 2012/22819, the contents of each of which are hereby incorporated in their entirety, polymyxin compounds for use in the treatment of microbial infections.

Surprisingly, the present inventors have found certain polymyxin derivatives, which have reduced toxicity compared to polymyxin or colistin, and are particularly effective at potentiating the activity of antibiotics such as rifampicin, and in some cases achieving enhanced in vitro potency compared to the polymyxin:antibiotic combination. Combinations containing these agents thus offer therapeutic options of consistently potent activity, but lower toxicity than currently available therapies.

SUMMARY OF THE INVENTION

In a general aspect the present invention provides a polymyxin compound of formula (I), as described herein, and its use in a method of treatment or prophylaxis, in combination with a second agent (which may be referred to as an active agent). The compounds of formula (I) may be used to treat a microbial infection, such as a Gram-negative bacterial infection.

In a first aspect of the invention there is provided a polymyxin compound of formula (I) for use in a method of treatment or prophylaxis, in combination with an active agent, wherein the active agent is selected from the group consisting of:
  rifampicin, rifabutin, rifalazil, rifapentine, and rifaximin;
  oxacillin, methicillin, ampicillin, cloxacillin, carbenicillin, piperacillin, tricarcillin, flucloxacillin, and nafcillin;
  azithromycin, clarithromycin, erythromycin, telithromycin, cethromycin, and solithromycin;
  aztreonam and BAL30072;
  meropenem, doripenem, imipenem, ertapenem, biapenem, tomopenem, and panipenem;
  tigecycline, omadacycline, eravacycline, doxycycline, and minocycline;
  ciprofloxacin, levofloxacin, moxifloxacin, and delafloxacin;
  Fusidic acid;
  Novobiocin;
  teichoplanin, telavancin, dalbavancin, and oritavancin,
and pharmaceutically acceptable salts and solvates thereof;

In a second aspect there is provided an active agent, such as defined in the first aspect, for use in a method of treatment or prophylaxis, in combination with a polymyxin compound of formula (I).

In a third aspect there is provided a combination of a polymyxin compound of formula (I) and an active agent as defined in the first aspect, for use in a method of treatment or prophylaxis In a fourth aspect there is provided a polymyxin compound of formula (I) for use in a method of treatment or prophylaxis of a microbial infection, in combination with an active agent as defined in the first aspect.

In a fifth aspect there is provided an active agent as defined in the first aspect for use in a method of treatment or prophylaxis of a microbial infection, in combination with a polymyxin compound of formula (I).

In a sixth aspect there is provided a method of treatment or prophylaxis, the method including the step of administering to a subject in need thereof a polymyxin compound of formula (I) and an active agent as defined in the first aspect.

In a seventh aspect there is provided a method of treatment or prophylaxis of a microbial infection, the method including the step of administering to a subject in need thereof a polymyxin compound of formula (I) and an active agent as defined in the first aspect.

In an eighth aspect there is provided the use of a polymyxin compound of formula (I) in the manufacture of a medicament for use in the treatment of a microbial infection in combination with an active agent as defined in the first aspect.

In a ninth aspect there is provided the use of an active agent as defined in the first aspect in the manufacture of a medicament for use in the treatment of a microbial infection in combination with a polymyxin compound of formula (I).

In a further aspect there is provided a pharmaceutical composition comprising a compound of formula (I) together with a second active agent, as defined in the first aspect, and a biologically acceptable excipient. Further, there is also provided a kit comprising a compound of formula (I) and comprising a second active agent, as defined in the first aspect. The compound of formula (I) and the second active agent may be provided separately within the kit.

In a further aspect of the invention there is provided a compound of formula (II). The compounds of formula (II) are a selection from the polymyxin compound of formula (I). The compounds of formula (II) are therefore provided in such aspects as described above for the compounds of formula (I).

The invention also provides a pharmaceutical composition comprising a compound of formula (II) and a biologically acceptable excipient, optionally together with a second active agent.

In a further aspect there is provided a compound of formula (II) or a pharmaceutical composition comprising the compound of formula (II) for use in a method of treatment.

The invention additionally provides a compound of formula (II) or a pharmaceutical composition comprising the compound of formula (II) for use in a method of treating a microbial infection, such as a Gram-negative bacterial infection.

The present invention also provides a method of identifying useful combinations for therapy, the method comprising testing a combination of a compound of formula (I) or (II) with a biologically active compound and determining the biological efficacy of the combination, for example with comparison to the biologically active compound alone and/or the compound of formula (I) or (II) alone.

In an alternative aspect, the compounds of formula (I) and (II) are suitable for use in the treatment of fungal infections, for example in combination together with an antifungal agent.

In a further aspect of the invention there is provided a compound of formula (I).

Other aspects of the invention are discussed in detail herein.

DETAILED DESCRIPTION OF THE INVENTION

Figure 1:
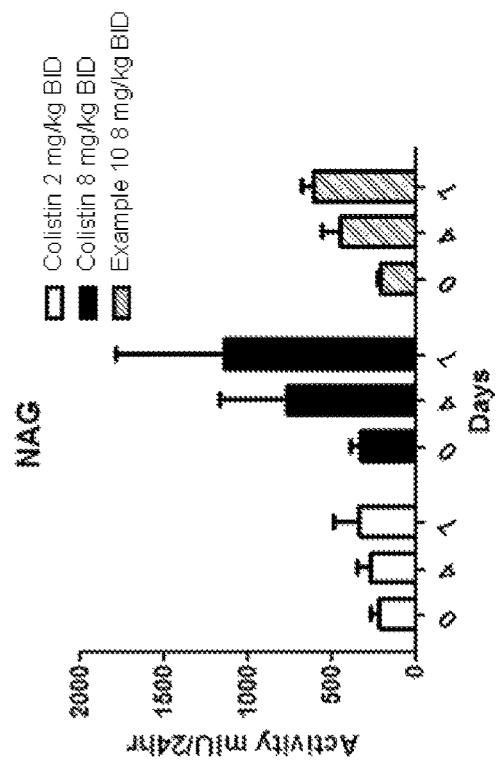
FIG. 1 shows the concentration of NAG (ng/24 h) at days 0, 4 and 7 for compounds 1, 4 and 10 and Colistin. The left-hand graph shows from left to right Colistin (2 mg/kg BID), Colistin (8 mg/kg BID), compound 1 (8 mg/kg BID) and 4 (8 mg/kg BID). The right-hand graph shows Colistin (2 mg/kg BID), Colistin (8 mg/kg BID) and compound 10 (8 mg/kg BID).
Figure 1:
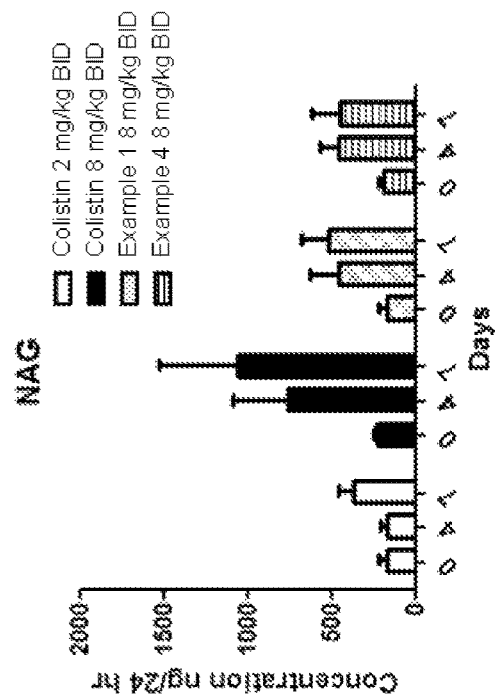

The present invention provides compounds of formula (I) and (II) for use in medical treatment, particularly in combination with a second agent. The present invention provides compounds of formula (II) and such compounds are a subset of the compounds of formula (I).

Broadly, the compounds of formula (I) and (II) are polymyxin compounds having an N terminal group that contains one, two or three hydroxyl groups and/or one, two or three amino groups. In addition, or as an alternative, the N terminal group has a nitrogen-containing heterocyclyl (or heterocyclylene) group and/or a nitrogen-containing heteroalkylene group. The N terminal group may be an alkyl group or may be or include an aryl, cycloalkyl or heterocyclyl group. The presence of a hydroxyl group or a basic amino group within the terminal group is associated with particular advantages, as discussed below.

The compounds of formula (I) and (II) have suitable antibacterial activity whilst also apparently exhibiting less toxicity, especially nephrotoxicity. The compounds may have comparable or improved biological activity compared to Polymyxin B or Colistin against one or more of *E. coli, P. aeruginosa, K. pneumonia,* or *A. baumannii* bacterial strains. Such compounds are useful alternatives to the polymyxin type compounds previously described in the art.

Some of the polymyxin compounds or polymyxin derivatives in the art are known or suspected to have a poor toxicity profile. For example, the use of compounds having a fatty acyl chain at the N terminal, such as Polymyxin B and Colistin, is associated with nephrotoxicity.

Vaara et al. (Antimicrob. Agents Chemother. 2008, 52, 3229) have suggested that the pharmacological and toxicity properties of a polymyxin compound may be altered with changes to the polymyxin polypeptide sequence. In particular, Vaara et al. have prepared a polymyxin compound having only three positive charges, whereas the polymyxin B nonapeptide carries five positive charges.

In contrast the present inventors have shown that adaptations to the N terminal of a polymyxin compound may reduce nephrotoxicity. As described herein, the N terminal has a substituent containing a hydroxyl group or an amino group (which may be in the form of a nitrogen-containing heterocycle).

Furthermore, the compounds of formula (I) and (II) are capable of increasing the antimicrobial activity of a second antimicrobial agent, such as rifampicin. Such combinations have comparable or improved biological activity compared to the combination of the second agent with Polymyxin B or Colistin, for example against one or more of *E. coli, P. aeruginosa, K. pneumonia,* or *A. baumannii* strains. Indeed, the inventors have found that the combination of a compound of formula (I) or (II) with a second active agent, such as an antimicrobial agent, provides an unexpected increase in biological activity. For example, compounds of formula (I) or (II) may have comparable biological activity compared to Polymyxin B or Colistin against one or more of *E. coli, P. aeruginosa, K. pneumonia,* or *A. baumannii* strains. However, when such compounds are used in combination with a second active agent, the combination has unexpectedly superior activity compared to the combination of Polymyxin B or Colistin with the same active agent. As noted above, the compounds of formula (I) and (II) may also posses an inherent antimicrobial activity.

Furthermore, the present inventors have found that each compound of formula (I) and (II) is active against a broad range of bacteria and each compound is capable of potentiating the activity of a second active agent, for example against *E. coli, P. aeruginosa, K. pneumonia,* or *A. baumannii* strains. In contrast the compounds and combinations previously described in the art have a varied profile of biological activity, and it is difficult to predict the extent to which a particular polymyxin compound will potentiate the activity of a second agent. In particular many known polymyxin derivatives, when used in combination with a second agent, have biological activities that are inferior to the combination of Polymyxin B or Colistin with the same active agent.

For example, WO 2008/017734 describes combinations of polymyxin derivatives with rifampicin, clarithromycin and other antibiotics. Combinations of NAB7061 and NAB739 with rifampicin are seen to have poor activity against *P. aeruginosa* compared with a combination of the Polymyxin B nonapeptide with rifampicin. Against *A. baumanii*, the combination of NAB739 with rifampicin has greater activity than combination of the Polymyxin B nonapeptide with rifampicin. However, the combination of NAB7061 with rifampicin has inferior activity. The combinations of NAB7061 and NAB739 with rifampicin are also seen to have superior activity against *E. coli* compared with the Polymyxin B nonapeptide combination. However, this improved activity is not predictable and improved activity is generally not consistent amongst the derivatives tested and the various microorganisms screened.

The combinations of the invention also apparently exhibit less toxicity compared to the combination of the second agent with Polymyxin B or Colistin, for example as measured against HK-2 cells. In particular the compounds have low nephrotoxicity.

Active Agent

The compounds of formula (I) and (II) may each be used together with a second agent. The inventors have found that such combinations have greater biological activity than would be expected from the individual activity of both compounds. The compounds of formula (I) and (II) can be used to potentiate the activity of the second agent. In particular, the compounds of formula (I) and (II) may be used together with a second agent to enhance the antimicrobial activity of that agent, for example against Gram-negative bacteria.

Without wishing to be bound by theory it is believed that the compounds of formula (I) and (II) act on the outer membrane of a cell e.g. a Gram-negative bacterial cell, to facilitate the uptake of the second agent into that cell. Thus, agents that are otherwise incapable or poor at crossing the outer membrane may be taken up into a target cell by the action of the compounds of formula (I) and (II).

In one embodiment, the combination of a compound of formula (I) or (II) with the second agent is active against Gram-negative bacteria. Here, it is not essential that individually either of the compound of formula (I) or (II) or the second agent have activity against Gram-negative bacteria.

In one embodiment, the second agent is an agent having a measured MIC value against a particular microorganism, such as a bacterium, that is less than 10, less than 5, or less than 1 micrograms/mL. The microorganism may be a Gram-negative bacteria, such as a Gram-negative bacteria selected from the group consisting of *E. coli, S. enterica, K. pneumoniae, K. oxytoca; E. cloacae, E. aerogenes, E. agglomerans, A. calcoaceticus, A. baumannii; Pseudomonas aeruginosa, Stenotrophomonas maltophila, Providencia stuartii, P. mirabilis*, and *P. vulgaris*.

Examples of second agents that have activity against Gram-negative bacteria include beta-lactams, tetracyclines, aminoglycosides and quinolones.

In one embodiment, the second agent is an agent having a measured MIC value against a particular microorganism, such as a Gram-negative bacterium, that is more than 4, more than 8, more than 16 or more than 32 micrograms/mL. In this embodiment, the second agent may be active against Gram-positive bacteria. For example, the second agent is an agent having a measured MIC value against a particular Gram-positive bacterium that is less than 10, less than 5, or less than 1 micrograms/mL. Here, the compound of formula (I) or (II) acts to facilitate the uptake of the second agent into the Gram-negative bacterial cell. The second agent is therefore able to act on a target within the Gram-negative bacterial cell, which target may be the same as the second agent's target in a Gram-positive bacterial cell.

The Gram-positive bacteria may be selected from the group consisting of *Staphylococcus* and *Streptococcus* bacteria, such as *S. aureus* (including MRSA), *S. epidermis, E. faecalis*, and *E. faecium*.

Examples of second agents that have activity against Gram-positive bacteria (at the MIC values given above, for example), and moderate activity against Gram-negative bacteria, include rifampicin, novobiocin, macrolides, pleuromutilins. In one embodiment, a compound having moderate activity against Gram-negative bacteria may have a measured MIC value against a Gram-negative bacterium that is less than 32, less than 64, or less than 128 micrograms/mL.

Also suitable for use are agents having activity against Gram-positive bacteria and which are essentially inactive against Gram-negative bacteria. Examples include fusidic acid, oxazolidinines (e.g. linezolid), glycopeptides (e.g. vancomycin), daptomycin and lantibiotics. In one embodiment, a compound having essentially no activity against Gram-negative bacteria may have a measured MIC value against a Gram-negative bacterium that is more than 32, more then 64, more than 128, more than 256 micrograms/mL.

MIC values for a particular agent may be determined using the techniques exemplified in the present application.

Under normal circumstances such agents are not necessarily suitable for use against Gram-negative bacteria owing to their relatively poor ability to cross the outer membrane of a Gram-negative bacterial cell. As explained above, when used together with a compound of formula (I) or (II), such agents are suitable for use.

In one embodiment, the active agent may be selected from the group consisting of rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts, solvates and prodrug forms thereof.

In one embodiment, the active agent may be selected from the group consisting of rifampicin, fusidic acid, novobiocin, oxacillin, azithromycin, aztreonam, meropenem, tigecycline, ciprofloxacin, and vancomycin.

In one embodiment, the active agent may be selected from the group consisting of rifampicin, fusidic acid, novobiocin, oxacillin, azithromycin, aztreonam, meropenem, tigecycline, and ciprofloxacin.

In one embodiment, the second agent is selected from the following classes of agent:
  Rifampicin family, including rifampicin, rifabutin, rifalazil, rifapentine, and rifaximin;
  Oxacillin family, including oxacillin, methicillin, ampicillin, cloxacillin, carbenicillin, piperacillin, tricarcillin, flucloxacillin, and nafcillin;
  Azithromycin family, including azithromycin, clarithromycin, erythromycin, telithromycin, cethromycin, and solithromycin;
  Aztreonam family, including aztreonam and BAL30072
  Meropenem family, including meropenem, doripenem, imipenem, ertapenem, biapenem, tomopenem, and panipenem;
  Tigecycline family, including tigecycline, omadacycline, eravacycline, doxycycline, and minocycline;
  Ciprofloxacin family, including ciprofloxacin, levofloxacin, moxifloxacin, and delafloxacin;
  Fusidic acid;
  Novobiocin;
  Vancomycin family, including vancomycin, teichoplanin, telavancin, dalbavancin, oritavancin, for example including teichoplanin, telavancin, dalbavancin, and oritavancin,
  and pharmaceutically acceptable salts and solvates thereof.

In addition or as an alternative to the second agents above, the second agent may be selected from the following classes of agent:
  Chloramphenicol;
  Clindamycin;
  Oxazolidinone family including linezolid, torezolid, and radezolid;
  Aminoglycoside family including amikacin, arbekacin, gentamicin, kanamycin, neomycin, netilmycin, paromomycin, streptomycin, tobramycin, apramycin, etimycin, and plazomycin;
  Daptomycin;
  Synercid;
  Pleuromutilin family, including retapamulin, and BC-3781;
  Lantibiotic family, including nisin, mersacidin, actagardine, deoxyactagardine B, NVB302, NVB333, Mu1140, and microbisporicin;
  Cephalosporin family, including ceftaroline, ceftobiprole, ceftriaxone, ceftolozone, cefepime, cefuroxime, cefpodoxime, cefdinir, cefixime, cefotaxime, and ceftazidime;
  Sulbactam; and
  Sulopenem,
  and pharmaceutically acceptable salts and solvates thereof The present inventors have found that the polymyxin compounds of formula (I) and (II) may be used together with certain compounds in the rifamycin family to treat microbial infections. The rifamycin family includes isolates rifamycin A, B, C, D, E, S and SV, and synthetically derivatised versions of these compounds, such as rifampicin (rifampin), rifabutin, rifalazil, rifapentine, and rifaximin, and pharmaceutically acceptable salts and solvates thereof.

In one embodiment, the active agent is rifampicin (rifampin) and pharmaceutically acceptable salts, solvates and prodrug forms thereof.

The present inventors have found that the polymyxin compounds of formula (I) and (II) may be used together with certain compounds in the meropenem family to treat microbial infections. In one embodiment, the meropenem family includes meropenem, doripenem, imipenem, ertapenem, biapenem, tomopenem, and panipenem, and pharmaceutically acceptable salts and solvates thereof.

The compounds of formula (II) may also be used together with the second agents above. The compounds of formula (II) may additionally be used together with other second agents such as vancomycin, fosfomycin, rifamycin, a beta-lactam (such as a cephalosporin or carbapenem), an aminoglycoside, a macrolide, a tetracyline, a lipopeptide, and/or an oxazolidinone.

In one embodiment, the compounds of formula (II) may additionally be used together with vancomycin or fosfomycin.

Alternatively, the second agent is not vancomycin, fosfomycin, rifamycin, a beta-lactam (such as a cephalosporin or carbapenem), an aminoglycoside, a macrolide, a tetracyline, a lipopeptide, an oxazolidinone and/or an anti-inflammatory such as a steroid.

The second agent may be used together with a further agent, for example an agent that limits or prevents the degradation of the second agent in vivo. For example, where the second agent has β-lactam functionality, an enzyme inhibitor may be used with the second agent to inhibit the action of β-lactamase. In another example a β-lactam antibiotic such as imipenem may be used together with a dehydropeptidase inhibitor, such as cilastatin, to prevent degradation of the β-lactam antibiotic by the kidney.

The second agent may optionally be used together with an anti-inflammatory such as a steroid.

Polymyxin Compounds of Formula (I) and (II)

The compounds of the invention of formula (I) and (II) are N terminal derivatives of the polymyxin series of compounds. The core of the compound of the invention is a deacylated version of a polymyxin compound or a nonapeptide version of a polymyxin compound, such as deacylated polymyxin B nonapeptide (PMBN) or deacylated Colistin.

The compound of formula (I) is represented thus:

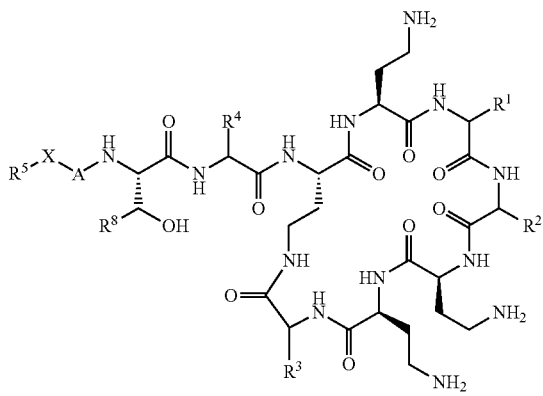

wherein:
—X— represents —C(O)—, —NHC(O)—, —OC(O)—, —CH$_2$— or —SO$_2$—; and
—R$^1$ together with the carbonyl group and nitrogen alpha to the carbon to which it is attached, is a phenylalanine, leucine or valine residue;
—R$^2$ together with the carbonyl group and nitrogen alpha to the carbon to which it is attached, is a leucine, iso-leucine, phenylalanine, threonine, valine or nor-valine residue;
—R$^3$ together with the carbonyl group and nitrogen alpha to the carbon to which it is attached, is a threonine or leucine residue;
—R$^4$ is C$_{1-6}$ alkyl substituted with one hydroxyl group or one amino group;
-A- is a covalent bond or an amino acid, such as an α-amino acid;
—R$^5$ is G-L$^2$-L$^1$-,
  -G is selected from:
    C$_{3-10}$ cycloalkyl,
    C$_{2-12}$ alkyl,
    C$_{5-12}$ aryl,
  -L$^1$- is a covalent bond, C$_{1-12}$ alkylene or C$_{2-12}$ heteroalkylene,
  -L$^2$- is a covalent bond or C$_{4-10}$ heterocyclylene,
  with the proviso that -L$^1$- is not C$_{1-12}$ alkylene when -G is C$_{2-12}$ alkyl,
  and G-L$^2$-L$^1$- is substituted with:
    (i) one, two or three hydroxyl groups, or
    (ii) one, two or three groups —NR$^6$R$^7$, or
    (iii) one or two groups —NR$^6$R$^7$, and one, two or three hydroxyl groups,
    with the proviso that (i), (ii) and (iii) are optional substituents when -L$^1$- is a nitrogen-containing C$_{2-12}$ heteroalkylene and/or -L$^2$- is a nitrogen-containing C$_{4-10}$ heterocyclylene,
or —R$^5$ is D-L$^1$-, where -D is C$_{4-10}$ heterocyclyl and -L$^1$- is as defined above, and D-L$^1$- is substituted with:
    (i) one, two or three hydroxyl groups, or
    (ii) one, two or three groups —NR$^6$R$^7$, or
    (iii) one or two groups —NR$^6$R$^7$, and one, two or three hydroxyl groups,
    with the proviso that (i), (ii) and (iii) are optional substituents when -L$^1$- is a nitrogen-containing C$_{2-12}$ heteroalkylene and/or -D is a nitrogen-containing C$_{4-10}$ heterocyclyl,
each —R$^6$ is independently hydrogen or C$_{1-4}$ alkyl;
each —R$^7$ is independently hydrogen or C$_{1-4}$ alkyl;
or —NR$^6$R$^7$ is a guanidine group; or
when -G is C$_{3-10}$ cycloalkyl or C$_{5-12}$ aryl, —R$^6$ and —R$^7$ together with the nitrogen atom form a C$_{4-10}$ heterocycle; and
and where an aryl group is present in —R$^5$ it is independently optionally substituted one or more substituents selected from —C$_{1-10}$ alkyl, such as —C$_{1-4}$ alkyl, halo, —CN, —NO$_2$, —CF$_3$, optionally —C(O)R$^{10}$, —NR$^{10}$C(O) R$^{10}$, —OCF$_3$, —CON(R$^{10}$)$_2$, —COOR$^9$, —OCOR$^{10}$, —NR$^{10}$COOR$^{10}$, —OCON(R$^{10}$)$_2$, —NR$^{10}$CON(R$^{10}$)$_2$, —OR$^9$, —SR$^9$, —NR$^{10}$SO$_2$R$^{10}$, —SO$_2$N(R$^{10}$)$_2$ and —SO$_2$R$^{10}$ where each —R$^9$ is independently —C$_{1-10}$ alkyl, such as —C$_{1-4}$ alkyl and each —R$^{10}$ is independently —H or —C$_{1-10}$ alkyl, such as —C$_{1-4}$ alkyl;
and optionally where an alkyl, cycloalkyl, or heterocyclyl group is present in —R$^5$ it is independently optionally substituted with one or more substituents selected from —C$_{1-10}$ alkyl, such as —C$_{1-4}$ alkyl, halo, —CN, —NO$_2$, —CF$_3$, —C(O)R$^{10}$, —NR$^{10}$C(O)R$^{10}$, —OCF$_3$, —CON (R$^{10}$)$_2$, —COOR$^9$, —OCOR$^{10}$, —NR$^{10}$COOR$^{10}$, —OCON $(R^{10})_2$, $-NR^{10}CON(R^{10})_2$, $-OR^9$, $-SR^9$, $-NR^{10}SO_2R^{10}$, $-SO_2N(R^{10})_2$ and $-SO_2R^{10}$ where each $-R^9$ is independently $-C_{1-10}$ alkyl, such as $-C_{1-4}$ alkyl and each $-R^{10}$ is independently $-H$ or $-C_{1-10}$ alkyl, such as $-C_{1-4}$ alkyl, except that alkyl is not substituted with alkyl;
$-R^8$ is hydrogen or methyl.

As described herein, in one embodiment, the compounds of formula (I) do not encompass deacylated polymyxin compounds, and do not encompass the polymyxin derivatives described by Katsuma et al. (*Chem. Pharm. Bull.* 2009, 57, 332).

The compounds of formula (II) are compounds including the compounds of formula (IIa), (IIb), (IIc) and (IId), optionally together with the compound of formula (IIe), (IIf) and (IIg). In one embodiment, the compounds of formula (II) are the compounds of formula (IIa).

The compounds of formula (IIa) are compounds where $-R^5$ is $G-L^2-L^1-$, and
-G is $C_{5-12}$ aryl,
-$L^1$- is a covalent bond, $C_{1-12}$ alkylene or $C_{2-12}$ heteroalkylene,
-$L^2$- is a covalent bond or $C_{4-10}$ heterocyclylene,
$-R^5$ is substituted with:
(i) one, two or three hydroxyl groups, or
(ii) one, two or three groups $-NR^6R^7$, or
(iii) one or two groups $-NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene,
and the aryl group is independently optionally substituted with one or more substituents selected from $-C_{1-4}$ alkyl, halo, $-CN$, $-NO_2$, $-CF_3$, $-NR^{10}C(O)R^{10}$, $-OCF_3$, $-CON(R^{10})_2$, $-COOR^9$, $-OCOR^{10}$, $-NR^{10}COOR^{10}$, $-OCON(R^{10})_2$, $-NR^{10}CON(R^{10})_2$, $-OR^9$, $-SR^9$, $-NR^{10}SO_2R^{10}$, $-SO_2N(R^{10})_2$ and $-SO_2R^{10}$ where each $-R^9$ is independently $-C_{1-10}$ alkyl, such as $-C_{1-4}$ alkyl and each $-R^{10}$ is independently $-H$ or $-C_{1-10}$ alkyl, such as $-C_{1-4}$ alkyl;
and $R^1$, $R^2$, $R^3$, $R^4$, $R^6$, $R^7$, $R^8$ have the same meanings as the compounds of formula (I) above. Additionally -A- and $-X-$ have the same meanings as the compounds of formula (I) above. Optionally, $-R^5-X-$ together are not Phe, His, Trp or Tyr, such as L-Phe, L-His, L-Trp and L-Tyr, for example when -A- is a covalent bond. Optionally, $-R^5-X-$ together are not Phe, and Trp, such as L-Phe and L-Trp, for example when -A- is a covalent bond.

The compounds of formula (IIb) are compounds where $-R^5$ is $G-L^2-L^1-$, and -G is $C_{3-10}$ cycloalkyl,
-$L^1$- is a covalent bond, $C_{1-12}$ alkylene or $C_{2-10}$ heteroalkylene,
-$L^2$- is a covalent bond or $C_{4-12}$ heterocyclylene,
with the proviso that -$L^2$- is a covalent bond only when -$L^1$- is $C_{2-10}$ heteroalkylene,
$-R^5$ is substituted with:
(i) one, two or three hydroxyl groups, or
(ii) one, two or three groups $-NR^6R^7$, or
(iii) one or two groups $-NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene,
and optionally the cycloalkyl group is independently optionally substituted with one or more substituents selected from $-C_{1-10}$ alkyl, such as $-C_{1-4}$ alkyl, halo, $-CN$, $-NO_2$, $-CF_3$, $-C(O)R^{10}$, $-NR^{10}C(O)R^{10}$, $-OCF_3$, $-CON(R^{10})_2$, $-COOR^9$, $-OCOR^{10}$, $-NR^{10}COOR^{10}$, $-OCON(R^{10})_2$, $-NR^{10}CON(R^{10})_2$, $-OR^9$, $-SR^9$, $-NR^{10}SO_2R^{10}$, $-SO_2N(R^{10})_2$ and $-SO_2R^{10}$ where each $-R^9$ is independently $-C_{1-10}$ alkyl, such as $-C_{1-4}$ alkyl and each $-R^{10}$ is independently $-H$ or $-C_{1-10}$ alkyl, such as $-C_{1-4}$ alkyl, except that alkyl is not substituted with alkyl,
and $R^1$, $R^2$, $R^3$, $R^4$, $R^6$, $R^7$, $R^8$ have the same meanings as the compounds of formula (I) above. Additionally -A- and $-X-$ have the same meanings as the compounds of formula (I) above.

The compounds of formula (IIc) are compounds where $-R^5$ is $G-L^2-L^1-$, where -G is $C_{3-10}$ cycloalkyl or $C_{2-12}$ alkyl,
-$L^1$- is a covalent bond or $C_{1-12}$ alkylene,
-$L^2$- is a covalent bond,
with the proviso that -$L^1$- is not $C_{1-12}$ alkylene when -G is $C_{2-12}$ alkyl,
$-R^5$ is substituted with:
(i) two or three groups $-NR^6R^7$, or
(ii) two groups $-NR^6R^7$, and one, two or three hydroxyl groups;
and optionally the alkyl or cycloalkyl group is independently optionally substituted with one or more substituents selected from $-C_{1-10}$ alkyl, such as $-C_{1-4}$ alkyl, halo, $-CN$, $-NO_2$, $-CF_3$, $-C(O)R^{10}$, $-NR^{10}C(O)R^{10}$, $-OCF_3$, $-CON(R^{10})_2$, $-COOR^9$, $-OCOR^{10}$, $-NR^{10}COOR^{10}$, $-OCON(R^{10})_2$, $-NR^{10}CON(R^{10})_2$, $-OR^9$, $-SR^9$, $-NR^{10}SO_2R^{10}$, $-SO_2N(R^{10})_2$ and $-SO_2R^{10}$ where each $-R^9$ is independently $-C_{1-10}$ alkyl, such as $-C_{1-4}$ alkyl and each $-R^{10}$ is independently $-H$ or $-C_{1-10}$ alkyl, such as $-C_{1-4}$ alkyl, except that alkyl is not substituted with alkyl,
and $R^1$, $R^2$, $R^3$, $R^4$, $R^6$, $R^7$, $R^8$ have the same meanings as the compounds of formula (I) above. Additionally -A- and $-X-$ have the same meanings as the compounds of formula (I) above. Optionally, $-R^5-X-$ together are not Lys, Dap, Arg, Dab, and Drg, such as L-Lys, L-Dap, L-Arg, L-Dab, and L-Drg, for example where -A- is a covalent bond.

The compounds of formula (IId) are compounds where $-R^5$ is $D-L^1-$, where $D-L^1-$ is substituted with:
(i) one, two or three hydroxyl groups, or
(ii) one, two or three groups $-NR^6R^7$, or
(iii) one or two groups $-NR^6R^7$, and one, two or three hydroxyl groups;
-$L^1$- is a covalent bond, $C_{1-12}$ alkylene or $C_{2-12}$ heteroalkylene,
with the proviso that (i), (ii) and (iii) are optional substituents when -$L^1$- is a nitrogen-containing $C_{2-12}$ heteroalkylene,
and optionally the heterocyclyl group is independently optionally substituted with one or more substituents selected from $-C_{1-10}$ alkyl, such as $-C_{1-4}$ alkyl, halo, $-CN$, $-NO_2$, $-CF_3$, $-C(O)R^{10}$, $-NR^{10}C(O)R^{10}$, $-OCF_3$, $-CON(R^{10})_2$, $-COOR^9$, $-OCOR^{10}$, $-NR^{10}COOR^{10}$, $-OCON(R^{10})_2$, $-NR^{10}CON(R^{10})_2$, $-OR^9$, $-SR^9$, $-NR^{10}SO_2R^{10}$, $-SO_2N(R^{10})_2$ and $-SO_2R^{10}$ where each $-R^9$ is independently $-C_{1-10}$ alkyl, such as $-C_{1-4}$ alkyl and each $-R^{10}$ is independently $-H$ or $-C_{1-10}$ alkyl, such as $-C_{1-4}$ alkyl, except that alkyl is not substituted with alkyl, and $R^1$, $R^2$, $R^3$, $R^4$, $R^6$, $R^7$, $R^8$ have the same meanings as the compounds of formula (I) above. Additionally -A-, -D, and —X— have the same meanings as the compounds of formula (I) above.

The compounds of formula (IIe) are compounds where -A- is an amino acid, such as an α-amino acid, and $R^1$, $R^2$, $R^3$, $R^4$, $R^5$, $R^6$, $R^7$, $R^8$, and —X— have the same meanings as the compounds of formula (I) above. It is noted that the compounds described by Katsuma et al. (*Chem. Pharm. Bull.* 2009, 57, 332) are Polymyxin B decapeptides. However, these compounds do not have the N terminal modifications that are present in the compounds of formula (IIe).

The compounds of formula (IIf) are compounds where -A- is a covalent bond, and $R^1$, $R^2$, $R^3$, $R^4$, $R^5$, $R^6$, $R^7$, $R^8$, and —X— have the same meanings as the compounds of formula (I) above, with the proviso that —X— and —$R^5$ together are not an L-α-amino acid residue. In one embodiment, —X— and —$R^5$ together are not L-Lys, L-Arg, L-Dap (L-α,β-diaminopropionic acid), L-Ser, L-Dab (L-α,γ-diaminobutyric acid), L-Dgp (L-α,β-diguanidinopropanoyl) or L-Abu.

In one embodiment, where —X— and —$R^5$ together are an α-amino acid, that α-amino acid is a D-α-amino acid residue.

It is noted that the compounds described by Katsuma et al. (*Chem. Pharm. Bull.* 2009, 57, 332) are des-fatty Polymyxin B decapeptides. The amino acid at the 1-position in the decapeptide is a L-α-amino acid, for example L-Lys, L-Arg, L-Dap (L-α,β-diaminopropionic acid), or L-Ser. The compounds of formula (IIf) do not encompass the compounds of Katsuma et al., as such amino acids are excluded from the definition of X— and —$R^5$ (when -A- is a covalent bond).

The compounds described by Sato et al. (*Peptide Science* 2007, 307) are des-fatty Polymyxin B decapeptides. The amino acid at the 1-position in the decapeptide is a L-α-amino acid, for example L-Dab, L-Dap, L-Dgp and L-Ser. The compounds of formula (IIf) do not encompass the compounds of Sato et al., as such amino acids are excluded from the definition of X— and —$R^5$ (when -A- is a covalent bond).

WO 2009/098357 describes a control compound NAB 705, which is a decapeptide comprising a Polymyxin B nonapeptide having an L-Abu residue at the N terminal. The compounds of formula (IIf) do not encompass the compound of WO 2009/098357, as the amino acid is excluded from the definition of —X— and —$R^5$ (when A- is a covalent bond). NAB 705 is also described in WO 2008/017734.

The compounds of Katsuma et al. and Sato et al. are not described for use in combination with an active agent.

The compounds of formula (IIg) are compounds where —$R^4$, together with the carbonyl group and nitrogen alpha to the carbon to which it is attached, is not Dab, for example is not (S)-Dab. Thus, —$R^4$ is not —$CH_2CH_2NH_2$ in an (S)-configuration about the carbon to which is attached. In this embodiment, -A-, $R^1$, $R^2$, $R^3$, $R^5$, $R^6$, $R^7$, $R^8$, and —X— have the same meanings as the compounds of formula (I) above.

In one embodiment, —$R^4$ is $C_1$ alkyl or $C_{3-6}$ alkyl substituted with one hydroxyl group or one amino group.

In one embodiment, —$R^4$ is $C_1$ alkyl substituted with one hydroxyl group or one amino group.

In one embodiment, —$R^4$, together with the carbonyl group and nitrogen alpha to the carbon to which it is attached, is Dap (α,β-diaminopropionic acid), such as (S)-Dap.

The compounds of formula (IIg) are compounds that do not share with Polymyxin B the amino acid residue at position 3. The work by Sato et al. and Katsuma et al., for example, is limited to the description of Polymyxin B and Colistin compounds, which possess a (S)-Dab residue at position 3.

WO 2012/168820 describes polymyxin compounds where the amino acid at position 3 has an altered side chain in comparison to Polymyxin B. WO 2012/168820 does not describe compounds having the N terminal groups (i.e. the group —X—$R^5$) that are described in the present case.

Where A is a covalent bond, $R^1$ (together with associated groups) is D-phenylalanine, $R^2$ (together with associated groups) is L-leucine, $R^3$ (together with associated groups) is L-threonine, $R^4$ (together with associated groups) is L-α,γ-diaminobutyric acid; and $R^8$ is methyl (and together with the associated groups is L-threonine), the compound is a polymyxin nonapeptide derivative having amino acids 2-10 of polymyxin B (polymyxin B nonapeptide). Further, where A is L-α,γ-diaminobutyric acid, the compound is a polymyxin derivative having amino acids 1-10 of polymyxin B.

Similarly, where A is a covalent bond, $R^1$ (together with associated groups) is D-leucine, $R^2$ (together with associated groups) is L-leucine, $R^3$ (together with associated groups) is L-threonine, $R^4$ (together with associated groups) is L-α,γ-diaminobutyric acid; and $R^8$ is methyl (and together with the associated groups is L-threonine), the compound is a polymyxin nonapeptide having amino acids 2-10 of polymyxin E (colistin nonapetide). Further, where A is L-α,γ-diaminobutyric acid, the compound is a polymyxin derivative having amino acids 1-10 of polymyxin E (colistin).

Polymyxin B

Polymyxin B nonapeptide has the structure shown below:

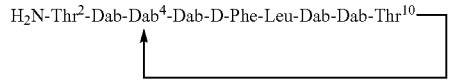

where positions 2, 4 and 10 are indicated (with reference to the numbering system used for the Polymyxin B decapeptide), and the amino acid residues are in the L-configuration, unless indicated.

The compounds of the invention are derivatives of polymyxin B nonapeptide, where (i) the N terminal amino group, —$NH_2$, is replaced with the group —NH-A-X—$R^5$ or —NH—X—$R^{15}$ as described herein and optionally (ii) the amino acid residues at 2, 3, 6, 7 and 10 positions are substituted with another amino acid residue.

For convenience, the compounds of the invention are represented by the formula (I) or (II) where the amino acids at positions 2, 3, 6, 7 or 10 are determined by the nature of the groups $R^8$, $R^4$, $R^1$, $R^2$ and $R^3$ respectively. Compounds of the invention, which include the variants described above, are biologically active.

A variant of the compound is a compound in which one or more, for example, from 1 to 5, such as 1, 2, 3 or 4 amino acids are substituted by another amino acid. The amino acid may be at a position selected from positions 2, 3, 6, 7 or 10 (referring to the numbering of residues used in polymyxin B). The substitution may be for another amino acid or for a stereoisomer.

—$R^1$

The —$R^1$ position corresponds to amino acid position 6 in the polymyxin compounds.

In one embodiment —$R^1$ together with the carbonyl group and nitrogen alpha to the carbon to which it is attached is a phenylalanine residue, for example a D-phenylalanine, or a leucine residue, such as a D-leucine residue.

—$R^2$

The —$R^2$ position corresponds to amino acid position 7 in the polymyxin compounds.

In one embodiment —$R^2$ together with the carbonyl group and nitrogen alpha to the carbon to which it is attached is a leucine or threonine residue, such as L-leucine or L-threonine.

—$R^3$

The —$R^3$ position corresponds to amino acid position 10 in the polymyxin compounds.

In one embodiment —$R^3$ together with the carbonyl group and nitrogen alpha to the carbon to which it is attached is a threonine residue, such as L-threonine.

—$R^4$

The —$R^4$ position corresponds to the side chain of the amino acid position 3 in the polymyxin compounds.

The group —$R^4$ together the carbonyl group and nitrogen alpha to the carbon to which it is attached, is an amino acid residue having an amino- or hydroxyl-containing side chain.

In one embodiment, —$R^4$ is $C_{1-4}$ alkyl, having one amino or one hydroxyl substituent.

In one embodiment, —$R^4$ has one amino substituent.

In one embodiment, —$R^4$ has one hydroxyl substituent.

The amino group may be —$NH_2$, —NHMe or —NHEt. In one embodiment, the amino group is —$NH_2$.

In one embodiment, —$R^4$ together with the carbonyl group and nitrogen alpha to the carbon to which it is attached, is α,γ-diaminobutyric acid (Dab), a serine residue, a threonine residue, a lysine residue, an ornithine residue, or α,β-diaminopropionic acid (Dap).

In one embodiment, —$R^4$ together with the carbonyl group and nitrogen alpha to the carbon to which it is attached, is α,γ-diaminobutyric acid (Dab), a serine residue, a lysine residue, or α,β-diaminopropionic acid (Dap).

In one embodiment, —$R^4$ together with the carbonyl group and nitrogen alpha to the carbon to which it is attached, is α,γ-diaminobutyric acid (Dab) or α,β-diaminopropionic acid (Dap), such as L-Dab or L-Dap.

In one embodiment, —$R^4$ together with the carbonyl group and nitrogen alpha to the carbon to which it is attached, is α,γ-diaminobutyric acid (Dab) or α,β-diaminopropionic acid (Dap), such as L-Dab or L-Dap.

In one embodiment, —$R^4$ together with the carbonyl group and nitrogen alpha to the carbon to which it is attached, is a lysine residue, such as L-Lys.

In one embodiment, —$R^4$ together with the carbonyl group and nitrogen alpha to the carbon to which it is attached, is Dab, such as L-Dab.

Compounds of the invention where —$R^4$ is a Dab side chain are obtainable from compounds such as Polymyxin B. Compounds where —$R^4$ is a Dap side chain may be prepared using the methods described in WO 2012/168820. Compounds where —$R^4$ is a serine side chain may be prepared using the methods described by Vaara et al. (see, for example, Antimicrob. Agents Chemother. 2008, 52, 3229).

—$R^8$

The amino acid residue including the group —$R^8$ corresponds to position 2 in the polymyxins.

In one embodiment, —$R^8$ is methyl. The resulting amino acid is therefore Thr.

In one embodiment, —$R^8$ is H. The resulting amino acid is therefore Ser.

—X—

The group —X— may be selected from —C(O)—, —NHC(O)—, —OC(O)—, —$CH_2$— and —$SO_2$—.

In one embodiment —X— is selected from —C(O)—, —$SO_2$— and —$CH_2$—.

In one embodiment —X— is —C(O)—.

In one embodiment —X— is —$SO_2$—.

In one embodiment —X— is —$CH_2$—.

The right-hand side of the group —X— is the point of attachment to NH, the amino terminal of the amino acid at position 2 or -A-, where present. The left-hand side of the group —X— is the point of attachment to —$R^5$.

-A-

In one embodiment, -A- is a covalent bond. Such compounds are referred to as nonapeptides, and are based on, for example, the nonapeptide forms of Polymyxin B, E and M (for example as having the structure shown above in relation to Polymyxin B). Nonapeptide forms of Polymyxin B and E are well known in the art. The compounds of the invention where -A- is a covalent bond may be prepared from nonapeptide forms by appropriate derivatisation of the N terminal.

In one embodiment, -A- is an amino acid. The amino acid may be an α-amino acid. Such compounds are referred to as decapeptides, and are based on, for example, deacylated decapeptide forms of Polymyxin B, E and M. Deacylated forms of Polymyxin B, E and M are well known in the art. Alternative decapeptides may be prepared from a nonapeptide or heptapeptide by appropriate coupling of an amino acid/s to the N terminal of the nonapeptide or heptapeptide. It is noted that the deacylated form Polymyxin M would appear to be identical to that reported for Polymyxin A by Cubist (see WO 2010/075416 and U.S. Pat. No. 8,415,307).

In one embodiment, -A- is an α-amino acid.

The α-amino acid includes proteinogenic ("natural") α-amino acids, optionally together with other α-amino acids.

In one embodiment, -A- is an amino acid selected from the group consisting of Lys, Arg, Dap, Ser, Thr, Ile, Tyr, His, Phe, Pro, Trp, Leu, Ala, Dab (α,γ-diaminobutyric acid), Dap (α,β-diaminopropionic acid), Dgp (α,β-diguanidinopropanoyl), ornithine and nor-valine, including L- and D-forms thereof.

In one embodiment, -A- is an amino acid selected from the group consisting of Dab, Pro, Dap, Gly, Ser, His, Phe, Arg, Tyr, and Leu, including L- and D-forms thereof.

In one embodiment, -A- is a D α-amino acid.

In one embodiment, -A- is a L α-amino acid.

Examples of α-amino acids that are not proteinogenic are those amino acids generated by post-translational modification, or by other means. Examples include Dab, Dap, Dgp (α,β-diguanidinopropanoyl), ornithine and nor-valine. Also included are amino acids such as the amino acid present in example compound A28. The amino acid has a piperidine side chain that is a gem di-substituent to the α-carbon. Thus the α-carbon is a ring atom in the piperidine ring. This is a cyclic analogue of Dab.

In one embodiment, -A- is a β-amino acid.

The compounds of the invention where -A- is an amino acid may be prepared from a deacylated nonapeptide, such as PMBN. The amino acid group may be added by simple amino acid coupling techniques. The N terminal of the resultant compound may be derivatised (after removal of any N terminal protecting groups, where appropriate) to provide the required $R^5$—X— terminal. Alternatively the N terminal of the amino acid group may be pre-derivatised prior to the amino acid coupling step. Thus the addition of the derivatised amino acid to the deacylated nonapeptide yields the required N terminal group directly.

In one embodiment, -A- is selected from Lys, Arg, Dap, Ser, Phe, Trp, Leu, Ala, Dab, Dap, ornithine or nor-valine, including L- and D-forms thereof.

In one embodiment, -A- is selected from Thr, Ser, Lys, Dab or Dap, for example L-Thr, L-Ser, L-Lys, L-Dab or L-Dap.

In one embodiment, -A- is Dab, such as L-Dab.

In an alternative embodiment, where -A- is an amino acid it is not Dab, for example it is not L-Dab.

—X— and —$R^5$

The compounds of formula (I) do not encompass the deacylated versions of Polymyxin B (Deacylpolymyxin B—DAPB), D, E (Deacylcolistin—DAC) or M, or Circulin A. The compounds of formula (I) do not encompass the nonapeptide versions of Polymyxin B (PMBN), D, E or M, or Circulin A.

In one embodiment, —X— and —$R^5$ together are not an α-amino acid residue, for example when -A- is a covalent bond. An α-amino acid residue is a group where —X— is —C(O)— and —$R^5$ has a group —$NR^6R^7$ (such as —$NH_2$) as a substituent to the carbon atom that is α to the group —X—.

In one embodiment, —X— and —$R^5$ together are not Thr, Ser, α,γ-diaminobutyric acid (Dab) or α,β-diaminopropionic acid (Dap) residues.

In one embodiment, for example where the core of the compound of formula (I) is Polymyxin B, X and $R^5$ together are not Lys, Arg, Dap, Ser, Phe, Trp, Leu or Ala residues.

In one embodiment, —X— and —$R^5$ together are not Lys, Arg, Dap, Ser, Phe, Trp, Leu, Ala α,γ-diaminobutyric acid (Dab) or α,β-diaminopropionic acid (Dap) residues.

In one embodiment, —X— and —$R^5$ together are not Ala, Ser, Thr, Val, Leu, Ile, Pro, Phe, Tyr, Trp, His, Lys or Arg residues.

In one embodiment, —X— and —$R^5$ together are not Ala, Ser, Thr, Val, Leu, Ile, Pro, Phe, Tyr, Trp, His, Lys, Arg,α, γ-diaminobutyric acid (Dab) or α,β-diaminopropionic acid (Dap) residues.

In one embodiment, —X— and —$R^5$ together are not an α-amino acid, for example a D or L α-amino acid, for example a L α-amino acid.

In one embodiment, —$R^5$ is not diaminophenyl, such as 3,5-diaminophenyl, for example when —X— is —C(O)—.

—$R^5$

In one embodiment, —$R^5$ is G-$L^2$-$L^1$-.

—$R^5$ may be G-$L^1$-, for example where -$L^2$- is a covalent bond.

—$R^5$ may be G-$L^2$-, for example where -$L^1$- is a covalent bond.

—$R^5$ may be -G, for example where -$L^1$- and -$L^2$- are covalent bonds.

In one embodiment, —$R^5$ is D-$L^1$-.

—$R^5$ may be -D, for example where -$L^1$- is a covalent bond.

In one embodiment, —$R^5$ has one, two or three hydroxyl and/or —$NR^6R^7$ groups. These groups may be provided on any group within —$R^5$, including -G, -D, -$L^1$- and -$L^2$-. In one embodiment, these groups are provided as substituents to -G, -D, and -$L^1$-.

It is noted that the hydroxyl and —$NR^6R^7$ groups are optionally substituents to the group D-$L^1$-. Where the hydroxyl and —$NR^6R^7$ substituents are discussed below, they may be referred to as substituents to —$R^5$.

In one embodiment, the one, two or three hydroxyl and/or —$NR^6R^7$ groups are optional substituents to —$R^5$. This may be the case where -$L^1$- is a nitrogen-containing $C_{2-12}$ heteroalkylene, and/or -$L^2$- is a nitrogen-containing $C_{4-10}$ heterocyclylene, and/or -D is a nitrogen-containing $C_{4-10}$ heterocyclyl.

In one embodiment, —$R^5$ has at least 5, at least 6, at least 7 or at least 8 carbon atoms present. In one embodiment, —$R^5$ has 1, 2, or 3 nitrogen atoms present. In one embodiment, the nitrogen atom is a basic nitrogen atom. The nitrogen atom may be present as NH.

In one embodiment, —$R^5$ has 1, 2, or 3 oxygen atoms present.

In one embodiment, —$R^5$ is not aminocyclohexyl, for example when -A- is a covalent bond, —X— is —C(O)— and —$R^1$, —$R^2$ and —$R^3$ are amino acid residues of polymyxin B.

Okimura et al. describe Polymyxin B nonapeptide compounds having aminocyclohexyl groups at the N terminal. These compounds are not described for use in combination with an active agent, In one embodiment, —$R^5$ is not an aminocyclohexyl group selected from the groups consisting of cis-2-aminocylcohexyl, trans-2-aminocylcohexyl, cis-3-aminocyclohexyl, cis-4-aminocylcohexyl, and trans-4-aminocylcohexyl. Additionally or alternatively, —$R^5$ is not trans-3-aminocyclohexyl.

Linker: -$L^2$-$L^1$- and -$L^1$-

Within the groups G-$L^2$-$L^1$- and D-$L^1$-, -$L^2$-$L^1$- and -$L^1$- may be regarded as linkers connecting the group —X— to -G or -D. The linker may be absent, for example where -$L^1$- and -$L^2$- are covalent bonds.

-$L^2$-$L^1$- in G-$L^2$-$L^1$-

In one embodiment, -$L^1$- and -$L^2$- are both covalent bonds. Thus, the group -G is connected directly to —X—. Here, the hydroxyl or amino groups (such as one, two or three hydroxyl and/or —$NR^6R^7$ groups) must be present on -G.

Where -$L^1$- is a nitrogen-containing $C_{2-12}$ heteroalkylene and/or -$L^2$- is a nitrogen-containing $C_{4-10}$ heterocyclylene, it is optional for G-$L^2$-$L^1$- to be substituted with one, two or three hydroxyl and/or —$NR^6R^7$ groups.

-$L^1$- in D-$L^1$-

In one embodiment, -$L^1$- is a covalent bond. Thus, the group -D is connected directly to —X—.

Where the group D-$L^1$- is substituted with a hydroxyl group or an amino group (such as one, two or three hydroxyl and/or —$NR^6R^7$ groups), the groups must be present on -D.

Where -$L^1$- is a nitrogen-containing $C_{2-12}$ heteroalkylene and/or -D is a nitrogen-containing $C_{4-10}$ heterocyclyl it is optional for D-$L^1$- to be substituted with one, two or three hydroxyl and/or —$NR^6R^7$ groups.

-$L^1$-

In one embodiment, -$L^1$- is a covalent bond or a $C_{1-12}$ alkylene group.

In one embodiment, -$L^1$- is a covalent bond.

In one embodiment, -$L^1$- is a $C_{1-12}$ alkylene group or a $C_{2-12}$ heteroalkylene group.

In one embodiment, -$L^1$- is a $C_{1-12}$ alkylene group.

In one embodiment, -$L^1$- is $C_{1-12}$ alkylene, for example $C_{1-6}$, $C_{1-4}$ or $C_{1-2}$ alkylene.

In one embodiment, -$L^1$- is —$CH_2$— or —$CH_2CH_2$—.

In one embodiment, -$L^1$- is $C_{2-12}$ alkylene, for example $C_{2-6}$ or $C_{2-4}$ alkylene.

In one embodiment, -$L^1$- is $C_{3-12}$ alkylene, for example $C_{3-6}$, $C_{4-12}$, $C_{5-12}$ or $C_{6-12}$ alkylene.

The alkylene group is a saturated, aliphatic alkylene group.

The alkylene group may be a linear or a branched alkylene group. In one embodiment, the alkylene group is linear.

Where -L$^1$- is an alkylene group and R$^5$ is substituted with one, two or three hydroxyl and/or —NR$^6$R$^7$ groups, one or more of the substituents may be substituents to the alkylene group.

In one embodiment, the alkylene group has one, two or three substituents.

In one embodiment, the alkylene group has one or two substituents, such as one substituent.

In one embodiment, the number of substituents on the alkylene group is no greater than the number of carbon atoms in the alkylene group. Thus, where -L$^1$- is a C$_2$ alkylene group it may be substituted with no more than two substituents.

Additional substituents, where present, may be located on -G or -D, where appropriate.

In one embodiment, the alkylene group is unsubstituted.

Where -L$^1$- is an alkylene group it may be substituted with a cycloalkyl group. A carbon atom in the alkylene group may form a covalent bond to a carbon ring atom of the group -G cycloalkyl. This arrangement is shown in example compounds 10 and A28. Alternatively, the cycloalkyl group may be a gem di-substituent to the alkylene group. Thus, a carbon atom in the alkylene group is also a carbon ring atom of the cycloalkyl group. This arrangement is shown in example compounds A30 and A34.

Alternatively, this latter arrangement in compounds such as A30 and A34 may be viewed as a cycloalkyl group having an optional alkyl substituent, where the one, two or three hydroxyl and/or —NR$^6$R$^7$ groups are located on the optional alkyl substituent.

In one embodiment, -L$^1$- is C$_{2-12}$ heteroalkylene. A heteroalkylene group is an alkylene group where one or more, such as two or three, or more, of the carbon atoms is replaced with a heteroatom selected from N, O and S. The superscript e.g. 4 in C$_4$ refers to the total number of carbon atoms and heteroatoms. The heteroatom of the heteroalkylene group is understood not to be a pendant amino, hydroxyl or thiol group.

In one embodiment, the heteroalkylene group contains one or two heteroatoms, for example one or two nitrogen atoms, such as one or two —NH—.

In one embodiment, heteroalkylene group is a nitrogen-containing heteroalkylene group.

The heteroatom may be provided as an interruption of the alkylene chain e.g. —CH$_2$—NH—CH$_2$—.

The heteroatom may be provided as a terminal group for connection to —X—, -L$^2$-, -G or -D, for example —CH$_2$—CH$_2$—NH— or —NH—CH$_2$—CH$_2$—. In these embodiments, the heteroatom is bonded to a carbon atom in —X—, -L$^2$-, -G or -D.

In one embodiment, the heteroatom of the heteroalkylene group is not covalently bonded to the group —X—.

In one embodiment, the heteroatom of the heteroalkylene group is not covalently bonded to the group -L$^2$-, -G or -D, where present. In an alternative embodiment, a heteroatom of the heteroalkylene group, such as —NH—, is covalently bonded to the group -L$^2$-, -G or -D, where present.

In one embodiment, -L$^1$- is C$_{2-12}$ heteroalkylene, for example C$_{2-6}$, C$_{2-4}$, C$_{3-6}$, C$_{3-12}$, C$_{4-6}$ or C$_{4-12}$ heteroalkylene.

The heteroalkylene group is a saturated, aliphatic heteroalkylene group.

The heteroalkylene group may be a linear or a branched heteroalkylene group. In one embodiment, the heteroalkylene group is linear.

In one embodiment, -L$^1$- is —NH—CH$_2$CH$_2$—NH—CH$_2$—.

In one embodiment, -L$^1$- is —CH$_2$—NH—CH$_2$CH$_2$—.

In one embodiment, the heteroalkylene group is unsubstituted.

In one embodiment, the heteroalkylene group is substituted, for example with one or two hydroxyl and/or —NR$^6$R$^7$ groups, such as one hydroxyl or —NR$^6$R$^7$ group. The substituents are provided on the carbon atoms within the heteroalkylene group In one embodiment, the number of substituents on the heteroalkylene group is no greater than the number of carbon atoms in the heteroalkylene group.

Where the heteroalkylene group is substituted, the substituents are preferably not provided on a carbon atom that is covalently bonded to a heteroatom of the heteroalkylene group. Where the heteroalkylene group is substituted, the substituents may be provided on a carbon atom that is not bonded to a heteroatom.

-L$^2$-

In one embodiment, -L$^2$- is a covalent bond.

In one embodiment, -L$^2$- is a C$_{4-10}$ heterocyclylene group, for example when -L$^1$- is a C$_{1-12}$ alkylene group.

In one embodiment, -L$^2$- is a C$_{4-7}$ heterocyclylene group, for example a C$_{5-7}$ or C$_{5-6}$ heterocyclylene group.

In one embodiment, the C$_{4-10}$ heterocyclylene contains one or two heteroatoms selected from N, S and O. Where a S atom is present, it may be in the form S, S(O) or S(O)$_2$. Where an N atom is present it may be in the form NH or NR, where —R is C$_{1-4}$ alkyl, such as methyl or ethyl. In one embodiment, the heterocyclylene group is a nitrogen-containing heterocyclylene. The heterocyclylene group may contain one or two nitrogen atoms. Each nitrogen atom may be optionally substituted with C$_{1-4}$ alkyl, where appropriate. In one embodiment the heterocyclylene group contains only nitrogen heteroatoms.

The term "heterocyclylene" in reference to the group -L$^2$- refers to a group (1) which has one or more heteroatoms (e.g., N, O, S) forming part of a ring system, wherein the ring system comprises one ring or two or more fused rings, wherein at least one ring of the ring system is a non-aromatic ring, and (2) which is attached to the rest of the molecule (including the groups -G and -L$^1$- as appropriate) via non-aromatic ring atoms (i.e., where each ring atom is part of a non-aromatic ring that is part of the ring system). At least one heteroatom is provided in a non-aromatic ring.

Thus, heterocyclylene may be a bicyclic ring system where one ring is an aromatic ring. The aromatic ring is not the ring that is connected to the rest of the molecule, as noted above. Examples of fused heterocyclyl systems are discussed below in relation to the group D.

In one embodiment, where a heterocyclylene group contains two or more fused rings, each ring is non-aromatic.

In one embodiment, the heterocyclylene group comprises one ring.

In one embodiment, the heterocyclylene group is unsubstituted. Thus, the hydroxyl and/or —NR$^6$R$^7$ groups are provided elsewhere, as required, for example on -L$^1$-, where present, or on -G or -D. Alternatively, where the heterocyclylene group is provided with a basic nitrogen group, such as NH, the hydroxyl and/or —NR$^6$R$^7$ groups are optional. In the absence of a basic nitrogen group, such as NH, the heterocyclylene group may be provided with a hydroxyl and/or —NR$^6$R$^7$ group.

In one embodiment, the heterocyclylene is connected to -L$^1$- or —X— via a carbon atom or nitrogen atom, where present, of the heterocyclylene ring.

In one embodiment, the heterocyclylene is connected to -G via a carbon atom or nitrogen atom, where present, of heterocyclylene ring.

In one embodiment, -L$^2$- is selected from piperidinylene, piperazinylene and pyrroldinylene. In one embodiment, -L$^2$- is selected from piperidinyl-1,4-ene, piperazinyl-1,4-ene and pyrroldinyl-1,3-ene.

It is noted that a heterocyclylene group does not encompass a pyridone diradical, such as a 2-pyridone diradical. Such compounds are considered to be aromatic, in view of the lactim tuatomoeric from. For the avoidance of doubt, therefore, -L$^2$- may be a heterocyclylene group, with the proviso that -L$^2$- is not a pyridone diradcial. Thus, the compound 5× of Magee at al, *J. Med. Chem.*, 2013, 56, 5079 is not encompassed by formula (I) of the present case.

Location of Hydroxyl and —NR$^6$R$^7$ Substituents

In one embodiment, a group —R$^5$, such as G-L$^2$-L$^1$- or D-L$^1$-, may be substituted with one, two or three hydroxyl groups.

In one embodiment, —R$^5$ is substituted with one hydroxyl group.

In one embodiment, a group —R$^5$ may be substituted with one, two or three groups —NR$^6$R$^7$.

In one embodiment, —R$^5$ is substituted with one —NR$^6$R$^7$ group.

In one embodiment, —R$^5$ is substituted with two or three groups —NR$^6$R$^7$.

In one embodiment, a group —R$^5$ may be substituted with one or two groups —NR$^6$R$^7$, and one, two or three hydroxyl groups.

In one embodiment, —R$^5$ is substituted with one —NR$^6$R$^7$ group and one hydroxyl group.

In one embodiment, a hydroxyl group, such as one, two or three hydroxyl groups, are substituents to -G.

In one embodiment, a hydroxyl group, such as one, two or three hydroxyl groups, are substituents to -D.

In one embodiment, a hydroxyl group, such as one, two or three hydroxyl groups, are substituents to -L$^1$-, where appropriate, for example where -L$^1$- is alkylene or heteroalkylene.

In one embodiment, a hydroxyl group, such as one, two or three hydroxyl groups, are substituents to -L$^2$-, where appropriate, for example where -L$^2$- is heterocyclylene.

In one embodiment, a —NR$^6$R$^7$ group, such as one, two or three —NR$^6$R$^7$ groups, are substituents to -G.

In one embodiment, a —NR$^6$R$^7$ group, such as one, two or three —NR$^6$R$^7$ groups, are substituents to -D.

In one embodiment, a —NR$^6$R$^7$ group, such as one, two or three —NR$^6$R$^7$ groups, are substituents to -L-, where appropriate, for example where -L$^1$- is alkylene or heteroalkylene.

In one embodiment, a —NR$^6$R$^7$ group, such as one, two or three —NR$^6$R$^7$ groups, are substituents to -L$^2$-, where appropriate, for example where -L$^2$- is heterocyclylene.

In one embodiment, G-L$^2$-L$^1$- is substituted with:
(i) one or two hydroxyl groups, or
(ii) one or two groups —NR$^6$R$^7$, or
(iii) one group —NR$^6$R$^7$ and one hydroxyl groups, with the proviso that (i), (ii) and (iii) are optional substituents when -L$^1$- is a nitrogen-containing C$_{2-12}$ heteroalkylene and/or -L$^2$- is a nitrogen-containing C$_{4-10}$ heterocyclylene.

In one embodiment, G-L$^2$-L$^1$- is optionally substituted with (i), (ii) and (iii), for instance where L$^1$- is a nitrogen-containing C$_{2-12}$ heteroalkylene and/or -L$^2$- is a nitrogen-containing C$_{4-10}$ heterocyclylene. In one embodiment, the proviso does not apply, therefore that (i), (ii) and (iii) are not optional substituents.

For the avoidance of doubt, where a group —R$^5$ is said to be substituted with one hydroxyl group (—OH), no further hydroxyl groups are present within —R$^5$. Likewise, where a group —R$^5$ is said to be substituted with one group —NR$^6$R$^7$, no further groups —NR$^6$R$^7$ are present within —R$^5$. Similarly, where —R$^5$ has two or three hydroxyl or —NR$^6$R$^7$ groups, the total number of hydroxyl or —NR$^6$R$^7$ groups is two or three.

As described in further detail below, where a hydroxyl group is present, it may be a substituent at a carbon atom α to the group —X—.

In one embodiment, where —R$^5$ has more than one substituent, the substituents are not located on the same carbon atom.

A carboxylic group (—COOH) is not to be construed as a hydroxyl group in the present case.

Where -L$^1$- has two or more carbon atoms present (e.g. C$_{2-12}$ alkylene or C$_{3-12}$ heteroalkylene) a substituent, where present, may be provided at a carbon atom that is α to the group —X—.

Similarly, where -L$^1$- and -L$^2$- are both covalent bonds, and -G is C$_{2-12}$ alkyl, the group C$_{2-12}$ alkyl may have a substituent at a carbon atom that is α to the group —X—.

In one embodiment, -L$^1$- is substituted with a hydroxyl group (for example one, two or three hydroxyl groups) and the hydroxyl group is provided at the carbon atom that is α to the group —X—. The present inventors have found that compounds having a hydroxyl group at the α carbon have a particularly improved potentiating activity compared to those compounds where the hydroxyl group is connected, for example, to a carbon atom that is not a the group —X—, for example β or γ to the group —X—, such as Example compound 25.

Similarly, where -L$^1$- and -L$^2$- are both covalent bonds, and -G is C$_{2-12}$ alkyl, the group C$_{2-12}$ alkyl may have a hydroxyl group provided at a carbon atom that is α to the group —X—.

Where -L$^1$- has more than two carbon atoms present (e.g. C$_{2-12}$ alkylene or C$_{3-12}$ heteroalkylene) a substituent, where present, may be provided at a carbon atom that is not α to the group X. For example, the substituent may be provided at a carbon atom that is β or γ to the group —X—. In one embodiment, no substituent is provided at the carbon atom α to the group —X—.

Similarly, where -L$^1$- and -L$^2$- are both covalent bonds, and -G is C$_{2-12}$ alkyl, the group C$_{2-12}$ alkyl may have a substituent that is not provided at a carbon atom that is α to the group —X—. For example, the substituent may be provided at a carbon atom that is β or γ to the group —X—.

In one embodiment, -L$^1$- is substituted with an amino group (for example one or two amino groups) and the amino group (i.e. —NR$^6$R$^7$) is provided at a carbon atom that is not α to the group X. Examples of compounds having such a substitution include Example compound 10 in the present case. The present inventors have found that compounds having an amino group at the α carbon, such as Example compound 40, may have reduced potentiating activity compared to those compounds where the amino group is connected, for example, to a carbon atom that is β or γ to the group —X—.

Subsequently, the inventors have established that the change in potentiating activity is related to the stereochemistry of the α carbon when it is substituted with the amino group. Example compounds A25 and A26 are diastereoisomers differing only in their stereochemistry at the α carbon. The compound A26 has superior activity to compound A25 when tested against various *E. coli, K. pneumoniae, P. aeruginosa,* and *A. baumannii* strains (see Table 6A).

Thus, in one embodiment, an amino group is provided at the carbon atom that is α to the group X.

Similarly, where -$L^1$- and -$L^2$- are both covalent bonds, and -G is $C_{2-12}$ alkyl may have an amino group provided at a carbon atom that is not α to the group —X—, for example β or γ to the group —X—.

In one embodiment, an amino or hydroxyl substituent is provided at a terminal carbon of the group -$L^1$- (e.g. $C_{2-12}$ alkylene or $C_{2-12}$ heteroalkylene) or the terminal carbon of the —$C_{2-12}$ alkyl, where present.

In one embodiment, the group -$L^1$- in D-$L^1$- is a covalent bond. Thus -D, which is a $C_{4-10}$ heterocyclyl, is connected directly to the group —X—.

In one embodiment, the group -$L^2$- is a $C_{4-10}$ heterocyclyl. Where -$L^1$- is a covalent bond, -$L^2$- is connected directly to the group —X—.

The connection of either these heterocyclyl groups to —X— is discussed below.

In one embodiment, an atom that is α to the group —X— may be a ring carbon atom of the heterocyclyl group. A ring heteroatom of the heterocyclyl group may be covalently bonded to the ring carbon atom that is α to the group —X— i.e. the ring heteroatom is β to the group —X—. In one embodiment, a ring heteroatom β to the group X is O or S, such as O. In one embodiment the ring heteroatom β to the group —X— is not N.

In one embodiment, a ring heteroatom γ to the group X is O, S or N.

In one embodiment, where -$L^1$- and -$L^2$- are both covalent bonds, and -G is a $C_{5-12}$ heteroaryl, the heteroaryl may be connected to the group —X— via a ring carbon atom, which is α to the group —X—). In one embodiment, a ring heteroatom, such as N, is not connected to the carbon atom which is α to the group —X—. Alternatively, a ring heteroatom, such as O or S, is connected to the carbon atom which is α to the group —X—.

In one embodiment, the group G-$L^2$-$L^1$- has one, two or three hydroxyl group and/or —$NR^6R^7$ substituents. These substituents may be provided on one or more of the groups -G-, -$L^2$- or -$L^1$-, where appropriate. In one embodiment, the substituents are provided on -G- and/or -$L^1$-. Where -$L^1$- is $C_{2-12}$ heteroalkylene, the one, two or three hydroxyl group and/or —$NR^6R^7$ substituents are optional.

The group D-$L^1$- optionally has one, two or three hydroxyl group and/or —$NR^6R^7$ substituents. Where the substituents are present they may be provided on -D or -$L^1$-, where appropriate.

In one embodiment, —$R^5$ is G-$L^2$-$L^1$-, where -G is $C_{5-12}$ aryl.

In one embodiment, —$R^5$ is G-$L^2$-$L^1$-, where -G is $C_{3-10}$ cycloalkyl or —$C_{2-12}$ alkyl, or —$R^5$ is D-$L^1$-, where D is $C_{4-10}$ heterocyclyl.

In one embodiment, G-$L^2$-$L^1$- is substituted with (i) one, two or three hydroxyl groups, (ii) one, two or three groups —$NR^6R^7$, or (iii) one or two groups —$NR^6R^7$, and one, two or three hydroxyl groups. Where an aryl group is present in G-$L^2$-$L^1$- it is independently optionally substituted one or more substituents selected from —$C_{1-10}$ alkyl, such as —$C_{1-4}$ alkyl, halo, —CN, —$NO_2$, —$CF_3$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$OCF_3$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-10}$ alkyl, such as —$C_{1-4}$ alkyl, and each —$R^{10}$ is independently —H or —$C_{1-10}$ alkyl, such as —$C_{1-4}$ alkyl.

In one embodiment, D-$L^1$- is optionally substituted with (i) one, two or three hydroxyl groups, (ii) one, two or three groups —$NR^6R^7$, or (iii) one, two or three groups —$NR^6R^7$, and one, two or three hydroxyl groups.

In one embodiment, D-$L^1$- is substituted with (i) one, two or three hydroxyl groups, (ii) one, two or three groups —$NR^6R^7$, or (iii) one, two or three groups —$NR^6R^7$, and one, two or three hydroxyl groups.

The groups $C_{3-10}$ cycloalkyl $C_{2-12}$ alkyl and $C_{4-10}$ heterocyclyl may be substituted with hydroxyl and/or —$NR^6R^7$ groups. Where the cycloalkyl or heterocyclyl groups include a fused aromatic ring, that aromatic ring may be optionally substituted with the optional substituents described herein. The optional further substituents do not include hydroxyl and/or —$NR^6R^7$ groups.

The group $C_{5-12}$ aryl is substituted with hydroxyl and/or —$NR^6R^7$ groups and the $C_{5-12}$ aryl group is optionally further substituted. The optional further substituents do not include hydroxyl and/or —$NR^6R^7$ groups.

It is not essential for the $C_{3-10}$ cycloalkyl, $C_{2-12}$ alkyl, $C_{5-12}$ aryl and $C_{4-10}$ heterocyclyl groups of -G and -D to be substituted with hydroxyl and/or —$NR^6R^7$ groups. In one embodiment, the hydroxyl and/or —$NR^6R^7$ groups may be provided on the linker elements of —$R^5$ e.g. -$L^1$- and/or -$L^2$-, where present.

Where —$R^5$ contains a nitrogen-containing heterocyclyl (or a nitrogen-containing heterocyclylene) or a nitrogen-containing heteroalkylene group, for example as part of -$L^1$-, -$L^2$- or -D, the hydroxyl and/or —$NR^6R^7$ groups may be optional.

Specifically, the hydroxyl and/or —$NR^6R^7$ groups are optional only where the heterocyclyl, heterocyclylene or heteroalkylene groups contain a basic nitrogen group, such as NH.

Thus, in one embodiment, G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
or a nitrogen-containing $C_{2-12}$ heteroalkylene and/or a nitrogen-containing $C_{4-10}$ heterocyclylene, where present, contains a basic nitrogen group, such as NH.

In one embodiment, G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclyl.

In one embodiment, G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups.

In one embodiment, D-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups
or a nitrogen-containing $C_{2-12}$ heteroalkylene, where present, and/or -D contains a basic nitrogen group, such as NH.

-D

The N terminal substituent of the polymyxin compound may include a $C_{4-10}$ heterocyclyl group ("heterocyclyl group"). Thus, in one embodiment, —$R^5$ includes the group -D, which is a $C_{4-10}$ heterocyclyl.

In one embodiment, -D is a nitrogen-containing heterocyclyl group. In such embodiments the hydroxyl and —NR⁶R⁷ groups are optional.

Where a heterocyclyl group does not contain a nitrogen ring atom, either or both of the heterocyclyl group and -L¹- must be substituted with one, two or three hydroxyl and/or —NR⁶R⁷ groups or -L¹- must be a nitrogen-containing $C_{2-12}$ heteroalkylene.

A heterocyclyl group may be optionally substituted, as described herein.

In one embodiment, $C_{4-10}$ heterocyclyl is $C_4$-6 or $C_{5-6}$ heterocyclyl, such as $C_5$ heterocyclyl or $C_6$ heterocyclyl.

In one embodiment, the $C_{4-10}$ heterocyclyl contains one or two heteroatoms selected from N, S and O. Where a S atom is present, it may be in the form S, S(O) or S(O)₂. Where an N atom is present it may be in the form NH or NR, where R is $C_{1-4}$ alkyl, such as methyl or ethyl.

In one embodiment, the heterocyclyl group is a nitrogen-containing heterocyclyl group.

In one embodiment, the $C_{4-10}$ heterocyclyl is piperidinyl, piperazinyl, morpholinyl, dioxanyl, thiomorpholinyl (including oxidised thiomorpholinyl), or pyrroldinyl.

In one embodiment, the $C_{4-10}$ heterocyclyl is piperidinyl, piperazinyl, thiomorpholinyl (including oxidised thiomorpholinyl), pyrroldinyl or morpholinyl.

In one embodiment, the $C_{4-10}$ heterocyclyl is piperidinyl, piperazinyl or pyrroldinyl.

Where a heterocyclyl is present it is connected to -L¹- or —X— via a ring carbon atom or a ring N atom, where present. In one embodiment, the heterocyclyl is connected via a ring carbon atom. In another embodiment, the heterocyclyl is connected via a ring nitrogen atom, where present.

Where a heterocyclyl is substituted with one, two or three hydroxyl and/or —NR⁶R⁷ groups, these groups are substituents to the heterocyclyl ring carbon atoms.

In one embodiment, a hydroxyl or —NR⁶R⁷ group, where present, is a substituent to a ring carbon atom that is 13 to a ring heteroatom.

In one embodiment, the heterocyclyl, if substituted, has a maximum of one or two substituents, which may be the same or different.

In one embodiment, the total number of carbon atoms in the heterocyclyl group, together with the total number of carbon atoms present in —R⁶ and —R⁷ (where present) is at least 5, at least 6, at least 7 or at least 8.

For the avoidance of doubt, the index "$C_{x-y}$" in terms such as "$C_{4-7}$ heterocyclyl", and the like, refers to the number of ring atoms, which may be carbon atoms or heteroatoms (e.g., N, O, S). For example, piperidinyl is an example of a $C_6$ heterocycyl group.

The term "heterocyclyl" in reference to the group -D refers to a group (1) which has one or more heteroatoms (e.g., N, O, S) forming part of a ring system, wherein the ring system comprises one ring or two or more fused rings, wherein at least one ring of the ring system is a non-aromatic ring, and (2) which is attached to the rest of the molecule by a non-aromatic ring atom (i.e., a ring atom that is part of a non-aromatic ring that is part of the ring system). For example: piperidino (piperidin-1-yl) and piperidin-4-yl are both examples of a $C_6$ heterocycyl group; 2,3-dihydro-1H-indol-1-yl (indolin-1-yl) is an example of a $C_9$ heterocycyl group; and both decahydro-quinolin-5-yl and 1,2,3,4-tetrahydroquinolin-4-yl are examples of a $C_{10}$ heterocyclyl group.

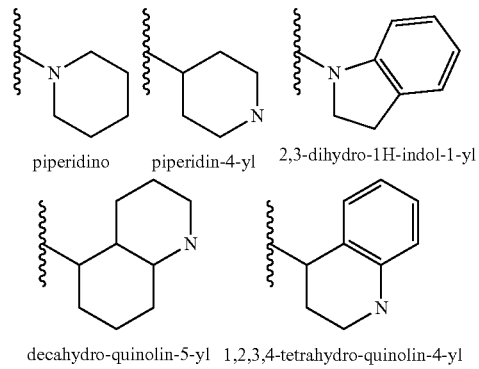

piperidino    piperidin-4-yl    2,3-dihydro-1H-indol-1-yl decahydro-quinolin-5-yl  1,2,3,4-tetrahydro-quinolin-4-yl The heterocyclyl group may be optionally substituted. The optional substituents are those described below.

In one embodiment, where a heterocyclyl group contains two or more fused rings, each ring is non-aromatic.

In one embodiment, the heterocyclyl group comprises one ring.

At least one heteroatom is provided in a non-aromatic ring.

-G

The group -G is selected from $C_{3-10}$ cycloalkyl, $C_{2-12}$ alkyl and $C_{5-12}$ aryl. A description of each of these is given below. The groups discussed below may be used together with any -L¹- and -L²-, as appropriate.

$C_{3-10}$ cycloalkyl

The N terminal substituent of the polymyxin compound may include a $C_{3-10}$ cycloalkyl group ("cycloalkyl group"). Thus, -G may be $C_{3-10}$ cycloalkyl.

When -G is $C_{3-10}$ cycloalkyl, -L¹- may be a covalent bond, $C_{1-12}$ alkylene or $C_{2-10}$ heteroalkylene, for example a covalent bond or $C_{1-12}$ alkylene.

When -G is $C_{3-10}$ cycloalkyl, -L²- may be a covalent bond or $C_{4-12}$ heterocyclyl, for example a covalent bond.

In one embodiment, $C_{3-10}$ cycloalkyl is a $C_3$-8 or $C_{3-6}$ cycloalkyl.

In one embodiment, $C_{3-10}$ cycloalkyl is cyclopentyl or cyclohexyl.

In one embodiment, the cycloalkyl, if substituted, has a maximum of one or two substituents, which may be the same or different.

In one embodiment, the number of substituents on the cycloalkyl group is no greater than the number of carbon atoms in the cycloalkyl group. Thus, where the alkyl group is a $C_6$ alkyl group it may be substituted with no more than six substituents.

In one embodiment, the total number of carbon atoms in the cycloalkyl group, together with the total number of carbon atoms present in —R⁶ and —R⁷ (where present) is at least 5, at least 6, at least 7 or at least 8.

In one embodiment, the cycloalkyl is cyclohexyl having a single hydroxyl or —NR⁶R⁷ group, such as a 4-substituted cyclohexyl group. In one embodiment, the cycloalkyl is cyclopentyl having a single hydroxyl or —NR⁶R⁷ group, such as a 2- or 3-substituted cyclopentyl group.

In one embodiment, the cycloalkyl is unsubstituted. In this embodiment, the substituents are located on the linker -L²-L¹-, which accordingly cannot be a covalent bond.

In one embodiment, for example where the core of the compound of formula (I) is Polymyxin B nonapeptide, the group G-L²-L¹- is not 2-aminocyclohexyl, 3-aminocyclohexyl or 4-aminocyclohexyl.

For the avoidance of doubt, "cycloalkyl" refers to a group (1) which has a ring system comprising one ring or two or more fused rings, wherein one ring of the fused ring system may be an aromatic ring, and (2) which is attached to the rest of the molecule by a non-aromatic ring atom (i.e., a ring atom that is part of a non-aromatic ring that is part of the ring system). For example: cyclohexyl is an example of a $C_6$ cycloalkyl group; and tetralin-2-yl is an example of a $C_{10}$ cycloalkyl group.

cyclohexyl          tetralin-2-yl

Where an aromatic ring is present, it may be optionally substituted. The optional substituents are those described as optional substituents for the $C_{5-12}$ aryl group.

In one embodiment, where the cycloalkyl comprises two or more fused rings, each ring is non-aromatic.

In one embodiment, the cycloalkyl group comprises one ring.

$C_{2-12}$ alkyl

The N terminal substituent of the polymyxin compound may be a $C_{2-12}$ alkyl group ("alkyl group"). Thus, -G may be $C_{2-12}$ alkyl.

When -G is $C_{2-12}$ alkyl, $-L^1-$ may be a covalent bond or $C_{2-10}$ heteroalkylene, such as a covalent bond.

When -G is $C_{2-12}$ alkyl, $-L^2-$ may be a covalent bond or $C_{4-12}$ heterocyclyl, for example a covalent bond.

In one embodiment, where -G is $C_{2-12}$ alkyl, both $-L^2-$ and $-L^1-$ are covalent bonds. Thus, -G is connected directly to —X—.

In one embodiment, $C_{2-12}$ alkyl is $C_{3-12}$ alkyl, for example $C_{4-12}$ or $C_{6-12}$ alkyl.

In one embodiment, $C_{2-12}$ alkyl is $C_{2-6}$ alkyl, for example $C_{2-4}$ alkyl.

The alkyl group is a saturated, aliphatic alkyl group. The alkyl group may be a linear or a branched alkyl group.

In one embodiment, the alkyl group is branched and the branch is not at the carbon atom that is α to the group $-L^2-$, $-L^1-$, or —X—.

In one embodiment, the number of substituents on the alkyl group is no greater than the number of carbon atoms in the alkyl group. Thus, where the alkyl group is a $C_2$ alkyl group it may be substituted with no more than two substituents.

In one embodiment, the total number of carbon atoms in the alkyl group, together with the total number of carbon atoms present in $—R^6$ and $—R^7$ (where present) is at least 5, at least 6, at least 7 or at least 8.

In one embodiment, the alkyl group has a substituent at the terminal carbon. Terminal carbon refers to a carbon atom that would be a $—CH_3$ if it bore no substituents. In a branched alkyl group this carbon may be the carbon atom that is at the terminal of the longest linear portion of the alkyl group.

In one embodiment, the alkyl group has a substituent that is located at a carbon atom that is β or γ the terminal carbon atom.

As noted above, in one embodiment, a $—NR^6R^7$ group, where present as a substituent to the alkyl group, is a substituent to a carbon atom that is not α to the group $-L^2-$, $-L^1-$, or —X—.

As noted above, in one embodiment, a hydroxyl group, where present as a substituent to the alkyl group, is a substituent to the carbon atom α to the group $-L^2-$, $-L^1-$, or —X—.

In one embodiment, the alkyl group has no substituent at the carbon atom α to the group $-L^2-L^1-$, or —X—.

In one embodiment, the alkyl, if substituted, has a maximum of one or two substituents, which may be the same or different.

In alternative aspects of the present invention, the group -G is a $C_{1-12}$ alkyl group rather than a $C_{2-12}$ alkyl group, and this alkyl group is substituted with hydroxyl groups and/or $—NR^6R^7$ as required. In one embodiment, $—R^5$ is $C_{1-12}$ alkyl group, such as $C_1$ alkyl. Where $—R^5$ is $C_1$ alkyl, one substituent is present, such as one $—NR^6R^7$ group.

The alkyl group may be optionally further substituted, as described in further detail below. In one embodiment, an alkyl group, if substituted, is substituted only with hydroxyl groups or $—NR^6R^7$ as required.

$C_{5-12}$ aryl

The N terminal substituent of the polymyxin compound may include or be a $C_{5-12}$ aryl group ("a group"). Thus, -G may be $C_{5-12}$ aryl.

When -G is $C_{5-12}$ aryl, $-L^1-$ may be a covalent bond, $C_{1-12}$ alkylene or $C_{2-10}$ heteroalkylene, for example a covalent bond or $C_{1-12}$ alkylene.

When -G is $C_{5-12}$ aryl, $-L^2-$ may be a covalent bond or $C_{4-12}$ heterocyclyl, for example a covalent bond.

The aryl group is optionally substituted, with these substituents being in addition to any hydroxyl or $—NR^6R^7$ groups.

In one embodiment, $C_{5-12}$ aryl is $C_{5-7}$ aryl

In one embodiment, $C_{5-12}$ aryl is $C_{6-10}$ carboaryl or $C_{5-12}$ heteroaryl.

In one embodiment, $C_{5-12}$ aryl is $C_{6-10}$ carboaryl.

In one embodiment, $C_{6-10}$ carboaryl is phenyl or napthyl.

In one embodiment, $C_{6-10}$ carboaryl is phenyl.

In one embodiment, $C_{5-12}$ aryl is $C_{5-12}$ heteroaryl, for example $C_{5-10}$, $C_{5-6}$, $C_5$ or $C_6$ heteroaryl.

The heteroaryl may contain one or two nitrogen atoms and additionally or alternatively, where the heteroaryl is a $C_5$ heteroaryl, it may contain an oxygen or sulfur atom In one embodiment, $C_{5-12}$ heteroaryl is independently furanyl, thienyl, pyrrolyl, imidazolyl, pyrazolyl, oxazolyl, isoxazolyl, thiazolyl, isothiazolyl, pyridyl, pyrimidinyl, pyrazinyl, pyridazinyl, quinolinyl, isoquinolinyl or indole. Additionally or alternatively, the $C_{5-12}$ heteroaryl is independently pyridone.

Where a heteroaryl is present in group -G it is connected to $-L^1-$, $-L^2-$ or —X— via a ring carbon atom or a ring N atom, where present. In one embodiment, the heteroaryl is connected via a ring carbon atom. In another embodiment, the heteroaryl is connected via a ring nitrogen atom, where present.

In one embodiment, $C_{5-12}$ aryl is phenyl or pyridine.

For the avoidance of doubt, "heteroaryl" refers to a group (1) which has one or more heteroatoms (e.g., N, O, S) forming part of a ring system, wherein the ring system comprises one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: pyridyl is an example of a $C_6$ heteroaryl group; isoquinolyl is an example of a $C_{10}$ heteroaryl group; and 1,2,3,4-tetrahydro-isoquinoline-7-yl is an example of a $C_{10}$ heteroaryl group.

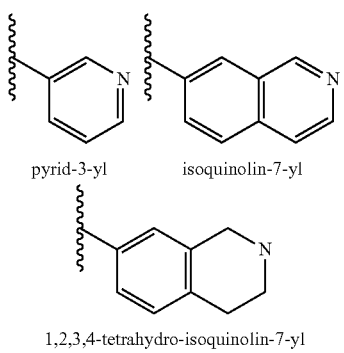

pyrid-3-yl          isoquinolin-7-yl 1,2,3,4-tetrahydro-isoquinolin-7-yl

In one embodiment, the aromatic ring atom contains a ring heteroatom.

In one embodiment, where a non-aromatic ring is provided, it has no optional substituents (though it may be provided with one or more hydroxyl or —$NR^6R^7$ groups).

In another embodiment, where a non-aromatic ring is provided, it is optionally substituted.

Suitable optional substituents for non-aromatic rings are discussed below in relation to cycloalkyl groups (where the non-aromatic ring contains only carbon ring atoms) and heterocyclyl groups (where the non-aromatic ring contains one or more heteroatom ring atoms).

In one embodiment, where a heteroaryl comprises two or more fused rings, each ring is an aromatic ring.

In one embodiment, the heteroaryl group comprises one aromatic ring.

Similarly, "carboaryl" refers to a group (1) which has a ring system comprising one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: phenyl is an example of a $C_6$ carboaryl group; and tetralin-6-yl is an example of a $C_{10}$ carboaryl group.

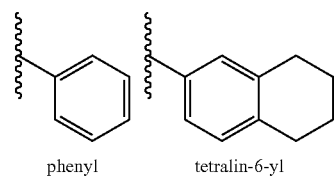

phenyl          tetralin-6-yl

In one embodiment, where a carboaryl comprises two or more fused rings, each ring is an aromatic ring.

In one embodiment, $C_{5-12}$ aryl is not diaminophenyl, such as 3,5-diaminophenyl, for example when —X— is —C(O)— and when -$L^1$- and -$L^2$- and are both covalent bonds.

In one embodiment, $C_{5-12}$ aryl is not trihydroxyphenyl, such as 3,4,5-trihydroxyphenyl, for example when —X— is —C(O)—.

It is noted that Sandow et al. (U.S. Pat. No. 5,565,423) describe Polymyxin octapeptides having a modified N terminal. The N terminal group contains a phenyl group that is optionally substituted by 1, 2 or 3 identical or different groups selected from hydroxyl, alkoxy, amino, carboxyl, alkylamino and halogen. The phenyl group may be linked to the N terminal via an alkylene spacer and/or an imino oxime group. Alternatively, the N terminal group contains a 2-aminothiazol-4-yl group.

The worked examples in Sandow et al. are limited to octapeptides having a 2-aminothiazol-4-yl group, a benzyl group or a 3,4,5-trihydroxyphenyl group. There are no examples where a nonapeptide or decapeptide are used, and there are no examples where the N terminal group contains amino functionality.

It is noted that WO 2012/168820 describes Polymyxin decapeptides having a modified N terminal. The publication suggests that the N terminal group could include aryl, aralkyl, heteroaryl and heteroaralkyl functionality, amongst other options. Aryl and heteroaryl groups may be linked to another aryl or heteroaryl group, amongst other options. The linker may be a bond, —$(CH_2)_n$—, —$(CH_2)_n$—O—$(CH_2)_p$—, —$(CH_2)_n$—S—$(CH_2)_p$—, or —$(CH_2)_n$—$NR^3$—$(CH_2)_p$—, where n is 0, 1, 2 or 3; and p is 0, 1, 2 or 3; and $R^3$ is H or $CH_3$.

The worked examples in WO 2012/168820 are limited to compounds where one aryl or heteroaryl group is linked directly to another aryl or heteroaryl group. There are no examples where a linker is present.

The compounds of the present case are distinguishable over the compounds in WO 2012/168820 for at least the reason that the compounds in the present case do not include derivatives where an aryl group is linked to the N terminal of a polymyxin nonapeptide derivative via another aryl group. In the present case an aryl group -G is linked to the N terminal directly or via a linker group -$L^2$-$L^1$-. The linker group -$L^2$-$L^1$- does not include arylene.

Furthermore, the compounds in the present case call for the N terminal group —$R^5$ to possess hydroxyl and/or —$NR^6R^7$ substituents, or to possess a nitrogen-containing heteroalkylene, heterocyclylene or heterocyclyl groups. Such groups are absent from the exemplified compounds in WO 2012/168820. The worked and comparative examples in the present case demonstrate that compounds that do not possess this requisite functionality have inferior biological activity. Example compound 37, containing a piperidine N terminal group, may be compared with comparative example compound C5, which contains a pyridine within the N terminal group. Compound 37 has superior activity against various K. pneumoniae and P. aeruginosa strains when compared with C5 (see Table 5A).

It is noted that heterocyclyl and heterocyclylene as referred to herein, refer to groups having at least one non-aromatic ring. It is noted that heteroaryl is used herein to refer to a group having at least one heteroatom-containing ring, such as at least one heteroatom-containing aromatic ring.

Compound having aryl groups at the N terminal are also described by Magee at al, J. Med. Chem., 2013, 56, 5079. An example is a compound 5× where an aryl group is linked to the N terminal of a polymyxin nonapeptide derivative via a pyridone group. Such a compound is not encompassed by the definitions of the present case. As explained above, a pyridone group is not considered to be a heterocyclene group within the meaning of that term as used in relation to the linker -$L^2$-. It is noted that the compound 5× was found to be less active compared to PMB in a murine neutropenic thigh model against P. aeruginosa strains.

Aryl Group Substituents

The group —$R^5$ may include an aryl group, for example where -G is $C_{5-12}$ aryl or $C_{3-10}$ cycloalkyl contains a fused aromatic ring, or where -D is $C_{4-10}$ heterocyclyl containing a fused aromatic ring.

Each aryl group is optionally substituted with one or more substituents.

Where the aryl group is optionally substituted, there may be one, two or three optional substituents.

Where a heteroaryl group is substituted, the substituents may be provided on a ring carbon atom, for example an aromatic ring carbon atom.

Each optional substituent is selected from the list consisting of —$C_{1-4}$ alkyl, halo, —CN, —$NO_2$, —$CF_3$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$OCF_3$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-4}$ alkyl and each —$R^{10}$ is independently —H or —$C_{1-4}$ alkyl.

In an alternative embodiment, each optional substituent is selected from the list consisting of —$C_{1-8}$ alkyl, such as —$C_{1-4}$ alkyl, halo, —CN, —$NO_2$, —$CF_3$, —$C(O)R^{10}$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$OCF_3$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-10}$ alkyl, such as —$C_{1-4}$ alkyl, and each —$R^{10}$ is independently —H or —$C_{1-10}$ alkyl, such as —$C_{1-4}$ alkyl.

In one embodiment, each optional substituent is independently selected from —$C_{1-8}$ alkyl, such as —$C_{1-4}$ alkyl, halo, —$NR^{10}C(O)R^{10}$, —$CON(R^{10})_2$, —$COOR^9$, —$OCOR^{10}$, —$NR^{10}COOR^{10}$, —$OCON(R^{10})_2$, —$OCF_3$, —$NR^{10}CON(R^{10})_2$, —$OR^9$, and —$SR^9$, where each —$R^9$ is independently —$C_{1-10}$ alkyl, such as —$C_{1-4}$ alkyl and each —$R^{10}$ is independently —H or —$C_{1-10}$ alkyl, such as —$C_{1-4}$ alkyl.

In one embodiment, each optional substituent is independently selected from —$C_{1-8}$ alkyl, such as —$C_{1-4}$ alkyl and halo.

In one embodiment, a halo group is —F, —Cl or —Br.

In one embodiment, a substituent is —$C_{1-8}$ alkyl, such as —$C_{1-4}$ alkyl.

In one embodiment, where a nitrogen atom is provided in an aromatic ring, it may be optionally substituted with —$R^9$ or —$R^{10}$, where appropriate. Typically, an aromatic ring nitrogen atom is unsubstituted or is optionally substituted with —$C_{1-8}$ alkyl, such as —$C_{1-4}$ alkyl, —$C(O)R^{10}$, —$CON(R^{10})_2$, —$COOR^9$, $SO_2N(R^{10})_2$ and —$SO_2R^{10}$. A reference to the substitution of an aromatic nitrogen ring atom refers to the replacement of a hydrogen radical in a group NH with a substituent group, for example where NH occurs in aromatic groups such as pyrrole, pyrazole and imidazole. In one embodiment, substitution does not refer to quaternised nitrogen ring atoms.

The optional substituents may include a —$C_{1-8}$ alkyl group, such as a $C_{1-4}$ alkyl group, e.g. —$R^9$ or —$R^{10}$, either alone or as part of a larger substituent group. It is noted that each $C_{1-8}$ alkyl group present, such as each $C_{1-4}$ alkyl group, may be substituted with the one, two or three hydroxyl and/or —$NR^6R^7$ groups.

In one embodiment, —$R^9$ or —$R^{10}$ are not substituted with a hydroxyl or —$NR^6R^7$ group.

Alkyl, Cycloalkyl and Heterocyclyl Group Substituents

In one embodiment, where an alkyl, cycloalkyl, or heterocyclyl group is present in —$R^5$, that group is independently optionally substituted with one or more substituents selected from —$C_{1-10}$ alkyl, such as —$C_{1-4}$ alkyl, halo, —CN, —$NO_2$, —$CF_3$, —$C(O)R^{10}$, —$NR^{10}C(O)R^{10}$, —$OCF_3$, —$CON(R^{10})_2$, —$COOR^9$, —$OCOR^{10}$, —$NR^{10}COOR^{10}$, —$OCON(R^{10})_2$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-10}$ alkyl, such as —$C_{1-4}$ alkyl, and each —$R^{10}$ is independently —H or —$C_{1-10}$ alkyl, such as —$C_{1-4}$ alkyl, except that alkyl is not substituted with alkyl.

In one embodiment, the optional substituents are selected —$C_{1-10}$ alkyl, such as —$C_{1-4}$ alkyl, —CN, —$NO_2$, —$C(O)R^{10}$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ and —$R^{10}$ is as defined above.

In one embodiment, the optional substituents are selected —$C_{1-10}$ alkyl, such as —$C_{1-4}$ alkyl, —$C(O)R^{10}$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ and —$R^{10}$ is as defined above.

In one embodiment an alkyl, cycloalkyl, or heterocyclyl group is not provided with optional substituents.

In one embodiment, each optional substituent is independently selected from —$C_{1-8}$ alkyl, such as —$C_{1-4}$ alkyl.

In one embodiment, each optional substituent is independently selected from —$C_{1-8}$ alkyl, such as —$C(O)R^{10}$.

A heterocycle group may be substituted on a ring carbon atom or a ring nitrogen atom. Where a heterocycle group is substituted at nitrogen, the substituents are selected appropriately for that atom. For example, a nitrogen ring atom may be substituted with a group selected from —$C_{1-4}$ alkyl, —$CF_3$, —$C(O)R^{10}$, —$CON(R^{10})_2$, —$COOR^9$, —$SO_2N(R^{10})_2$ and —$SO_2R^{10}$. In a further example, a nitrogen ring atom may be substituted with —$C_{1-4}$ alkyl, —$C(O)R^{10}$, and —$COOR^9$.

The optional substituents may include a —$C_{1-8}$ alkyl group, such as a $C_{1-4}$ alkyl group, e.g. —$R^9$ or —$R^{10}$, either alone or as part of a larger substituent group. It is noted that each $C_{1-8}$ alkyl group present, such as each $C_{1-4}$ alkyl group, may be substituted with the one, two or three hydroxyl and/or —$NR^6R^7$ groups.

In one embodiment, —$R^9$ or —$R^{10}$ are not substituted with a hydroxyl or —$NR^6R^7$ group.

—$R^6$ and —$R^7$

In one embodiment, each —$R^6$ and —$R^7$, where present, is H.

In one embodiment, —$R^6$ is H and —$R^7$ is alkyl, such as methyl or ethyl, such as methyl.

In one embodiment, —$R^6$ is methyl or ethyl, such as methyl.

Where -G is an aryl or cycloalkyl group, —$R^6$ and —$R^7$ may together with the nitrogen atom form a heterocycle, for example $C_{4-10}$ heterocyclyl.

In one embodiment, the $C_{4-10}$ heterocyclyl contains one or two heteroatoms selected from N, S and O. Where a S atom is present, it may be in the form S, S(O) or $S(O)_2$. Where an N atom is present it me be in the form NH or NR, where R is $C_{1-4}$ alkyl, such as methyl or ethyl.

In one embodiment, the $C_{4-10}$ heterocyclyl is piperidinyl, piperazinyl, morpholinyl, dioxanyl, thiomorpholinyl (including oxidised thiomorpholinyl), or pyrroldinyl.

In one embodiment, the $C_{4-10}$ heterocyclyl is piperidinyl, piperazinyl, thiomorpholinyl (including oxidised thiomorpholinyl), pyrroldinyl or morpholinyl.

In one embodiment, the $C_{4-10}$ heterocyclyl is piperidinyl, piperazinyl or pyrroldinyl.

In one embodiment, one group —$NR^7R^8$, where present, is a guanidine group, such as —$NHC(NH)NH_2$.

—$R^9$

In one embodiment, —$R^9$ is methyl or ethyl.

In one embodiment, —$R^9$ is methyl.

—R¹⁰

In one embodiment, —R¹⁰ is —H.
In one embodiment, —R¹⁰ is methyl or ethyl.
In one embodiment, —R¹⁰ is methyl.

Salts, Solvates and Other Forms

Examples of salts of compound of formula (I) and (II) include all pharmaceutically acceptable salts, such as, without limitation, acid addition salts of strong mineral acids such as HCl and HBr salts and addition salts of strong organic acids such as a methanesulfonic acid salt. Further examples of salts include sulphates and acetates such as trifluoroacetate or trichloroacetate.

In one embodiment the compounds of the present disclosure are provided as a sulphate salt or a trifluoroacetic acid (TFA) salt. In one embodiment the compounds of the present disclosure are provided as acetate salts.

A compound of formula (I) or (II) can also be formulated as prodrug. Prodrugs can include an antibacterial compound herein described in which one or more amino groups are protected with a group which can be cleaved in vivo, to liberate the biologically active compound. In one embodiment the prodrug is an "amine prodrug". Examples of amine prodrugs include sulphomethyl, as described in e.g., Bergen et al, *Antimicrob. Agents and Chemotherapy*, 2006, 50, 1953 or HSO₃—FMOC, as described in e.g. Schechter et al, *J. Med Chem* 2002, 45(19) 4264, and salts thereof. Further examples of amine prodrugs are given by Krise and Oliyai in *Biotechnology: Pharmaceutical Aspects*, 2007, 5(2), 101-131.

In one embodiment a compound of formula (I) or (II) is provided as a prodrug.

A reference to a compound of formula (I) or (II) is also a reference to a solvate of that compound. Examples of solvates include hydrates.

A compound of formula (I) or (II) includes a compound where an atom is replaced by a naturally occurring or non-naturally occurring isotope. In one embodiment the isotope is a stable isotope. Thus a compound described here includes, for example deuterium containing compounds and the like. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Certain compounds of formula (I) or (II) may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-6}$alkyl includes n-propyl and iso-propyl; butyl includes n-, iso-, sec-, and tert-butyl; methoxyphenyl includes ortho-, meta-, and para-methoxyphenyl).

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Preferred Compounds

In one embodiment, a compound of formula (I) or (II) is selected from the groups consisting of the exemplified compounds described herein.

In one aspect of the invention there is provided a compound of formula (I).

In one embodiment, the compound is a compound of formula (I) with the proviso that, $R^5$—X— together is not a group selected from the list consisting of Lys, Arg, Dap, Ser, Dab, Dgp (α,β-diguanidinopropanoyl), Thr and Abu. The proviso may apply where -A- is a covalent bond. Each of the amino acids may be an L-amino acid.

In one embodiment, the compound is a compound of formula (I) with the proviso that $R^5$—X— together is not a group selected from the list consisting of 2-aminocyclohexyl, 3-aminocyclohexyl and 4-aminocyclohexyl. The proviso may apply where -A- is a covalent bond.

Each of the provisos above may apply only when the core of the compound is a Polymyxin B nonapeptide i.e. where —$R^1$ to —$R^4$ and —$R^8$ have the substituents present in Polymyxin B nonapeptide.

Methods of Treatment

The compounds of formula (I) and (II), or pharmaceutical formulations containing these compounds, are suitable for use in methods of treatment and prophylaxis. The compounds may be administered to a subject in need thereof. The compounds are suitable for use together with an active agent ("a second active agent"), for example a second active agent that is an antimicrobial agent.

The compounds of formula (I) and (II) are for use in a method of treatment of the human or animal body by therapy. In some aspects of the invention, a compound of formula (I) and (II) may be administered to a mammalian subject, such as a human, in order to treat a microbial infection.

Another aspect of the present invention pertains to use of a compound of formula (I) and (II) in the manufacture of a medicament for use in treatment. In one embodiment, the medicament comprises a compound of formula (I) and (II). In one embodiment, the medicament is for use in the treatment of a microbial infection.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The compounds may be used to treat a subject having a microbial infection, or at risk of infection from a microorganism, such as a bacterium.

The microbial infection may be a bacterial infection such as a Gram-negative bacterial infection.

Examples of Gram-negative bacteria include, but are not limited to, *Escherichia* spp., *Klebsiella* spp., *Enterobacter* spp., *Salmonella* spp., *Shigella* spp., *Citrobacter* spp., *Morganella morganii*, *Yersinia pseudotuberculosis* and other Enterobacteriaceae, *Pseudomonas* spp., *Acinetobacter* spp., *Moraxella*, *Helicobacter*, *Stenotrophomonas*, Bdellovibrio, acetic acid bacteria, *Legionella* and alpha-proteobacteria such as *Wolbachia* and numerous others.

Medically relevant Gram-negative cocci include three organisms, which cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae*, *Klebsiella pneumoniae*, *Legionella pneumophila*, *Pseudomonas aeruginosa*), primarily urinary problems (*Escherichia coli*, *Enterobacter cloacae*), and primarily gastrointestinal problems (*Helicobacter pylori*, *Salmonella enterica*).

Gram-negative bacteria associated with nosocomial infections include *Acinetobacter baumannii*, which causes bacteremia, secondary meningitis, and ventilator-associated pneumonia in intensive-care units of hospital establishments.

In one embodiment the Gram-negative bacterial species is selected from the group consisting of *E. coli, S. enterica, K. pneumoniae, K. oxytoca; E. cloacae, E. aerogenes, E. agglomerans, A. calcoaceticus, A. baumannii; Pseudomonas aeruginosa, Stenotrophomonas maltophila, Providencia stuartii, P. mirabilis*, and *P. vulgaris*.

In one embodiment the Gram-negative bacterial species is selected from the group consisting of *E. coli, K. pneumoniae, Pseudomonas aeruginosa*, and *A. baumannii*.

The compounds of formula (I) or (II) or compositions comprising the same are useful for the treatment of skin and soft tissue infections, gastrointestinal infection, urinary tract infection, pneumonia, sepsis, intra-abdominal infection and obstetrical/gynaecological infections. The infections may be Gram-positive or Gram-negative bacterial infections.

The compounds of formula (I) or (II) or compositions comprising the same are useful for the treatment of *Pseudomonas* infections including *P. aeruginosa* infection, for example skin and soft tissue infections, gastrointestinal infection, urinary tract infection, pneumonia and sepsis.

The compounds of formula (I) or (II) or compositions comprising the same are useful for the treatment of *Acinetobacter* infections including *A. baumanii* infection, for pneumonia, urinary tract infection and sepsis.

The compounds of formula (I) or (II) or compositions comprising the same are useful for the treatment of *Klebsiella* infections including *K. pneumoniae* infection, for pneumonia, urinary tract infection, meningitis and sepsis.

The compounds of formula (I) or (II) or compositions comprising the same are useful for the treatment of *E. coli* infection including *E. coli* infections, for bacteremia, cholecystitis, cholangitis, urinary tract infection, neonatal meningitis and pneumonia.

The active agent may be an agent that has activity against the microorganism. The active agent may be active against Gram-negative bacteria. The active agent may be active against a microorganism selected from the list given above.

In one embodiment, the second active agent has an MIC value of 10 micrograms/mL or less against a microorganism such as *E. coli*, in the absence of the compound of formula (I) or (II).

The microorganism may be a microorganism selected from the group above.

Specific compounds for use as second active agents are described herein and include:
rifampicin, rifabutin, rifalazil, rifapentine, and rifaximin;
oxacillin, methicillin, ampicillin, cloxacillin, carbenicillin, piperacillin, tricarcillin, flucloxacillin, and nafcillin;
azithromycin, clarithromycin, erythromycin, telithromycin, cethromycin, and solithromycin;
aztreonam and BAL30072;
meropenem, doripenem, imipenem, ertapenem, biapenem, tomopenem, and panipenem;
tigecycline, omadacycline, eravacycline, doxycycline, and minocycline;
ciprofloxacin, levofloxacin, moxifloxacin, and delafloxacin;
Fusidic acid;
Novobiocin;
teichoplanin, telavancin, dalbavancin, and oritavancin,
and pharmaceutically acceptable salts and solvates thereof;

In one embodiment, specific compounds for use as second active agents are described herein and include rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts and solvates thereof.

In an alternative aspect, the compounds of formula (I) and (II) are suitable for use in the treatment of fungal infections, for example in combination together with an antifungal agent. The antifungal agent may be selected from a polyene antifungal, for example amphotericin B, an imidazole, triazole, or thiazole antifungal, for example micaonazole, fluconazole or abafungin, an allylamine, an echinocandin, or another agent, for example ciclopirox.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included.

For example, use with patients who have not yet developed the condition, but who are at risk of developing the condition, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, as described herein, in which two or more treatments or therapies are combined, for example, sequentially or simultaneously.

Combination Therapy

A compound of formula (I) or (II) may be administered in conjunction with an active agent.

Administration may be simultaneous, separate or sequential.

The methods and manner of administration will depend on the pharmacokinetics of the compound of formula (I) or (II) and the second agent.

By "simultaneous" administration, it is meant that a compound of formula (I) or (II) and a second agent are administered to a subject in a single dose by the same route of administration.

By "separate" administration, it is meant that a compound of formula (I) or (II) and a second agent are administered to a subject by two different routes of administration which occur at the same time. This may occur for example where one agent is administered by infusion and the other is given orally during the course of the infusion.

By "sequential" it is meant that the two agents are administered at different points in time, provided that the activity of the first administered agent is present and ongoing in the subject at the time the second agent is administered.

Generally, a sequential dose will occur such that the second of the two agents is administered within 48 hours, preferably within 24 hours, such as within 12, 6, 4, 2 or 1 hour(s) of the first agent. Alternatively, the active agent may be administered first, followed by the compound of formula (I) or (II).

Ultimately, the order and timing of the administration of the compound and second agent in the combination treatment will depend upon the pharmacokinetic properties of each.

The amount of the compound of formula (I) or (II) to be administered to a subject will ultimately depend upon the nature of the subject and the disease to be treated. Likewise, the amount of the active agent to be administered to a subject will ultimately depend upon the nature of the subject and the disease to be treated.

Formulations

In one aspect, the present invention provides a pharmaceutical composition comprising a compound of formula (I) or (II) together with a pharmaceutically acceptable carrier. The pharmaceutical composition may additionally comprise a second active agent. In an alternative embodiment, where a second agent is provided for use in therapy, the second agent may be separately formulated from the compound of formula (I) or (II). The comments below made in relation to the compound of formula (I) or (II) may therefore also apply to the second agent, as separately formulated.

While it is possible for the compound of formula (I) or (II) to be administered alone or together with the second agent, it is preferable to present it as a pharmaceutical formulation (e.g., composition, preparation, medicament) comprising at least one compound of formula (I) or (II), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound of formula (I) or (II), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound. The composition optionally further comprises the second active agent in a predetermined amount.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005.

The formulations may be prepared by any methods well known in the art of pharmacy. Such methods include the step of bringing into association the compound of formula (I) or (II) with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs. Where a liposome is used, it is noted that the liposome may contain both the compound of formula (I) or (II) and the second agent.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound. As an alternative method of administration, a dry powder delivery may be used as an alternative to nebulised aerosols.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases. Additionally or alternatively, a formulation for pulmonary administration may be formulated for administration from a nebuliser or a dry powder inhaler. For example, the formulation may be provided with carriers or liposomes to provide a suitable particle size to reach the appropriate parts of the lung, to aid delivery of an appropriate dose and/or to enhance retention in the lung tissue.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semiliquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 100 µg/mL, for example from about 10 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

Generally, the methods of the invention may comprise administering to a subject an effective amount of a compound of formula (I) or (II) so as to provide an antimicrobial effect. The compound of formula (I) or (II) may be administered at an amount sufficient to potentiate the activity of a second active agent. The second active agent is administered to a subject at an effective amount so as to provide an antimicrobial effect.

It will be appreciated by one of skill in the art that appropriate dosages of the compound of formula (I) or (II) or the active agent, and compositions comprising the compound of formula (I) or (II) or the active agent, can vary from patient to patient. Determining the optimal dosage will generally involve the balancing of the level of therapeutic benefit against any risk or deleterious side effects. The selected dosage level will depend on a variety of factors including, but not limited to, the activity of the particular compound of formula (I) or (II) or the active agent, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound of formula (I) or (II) or the active agent and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of a compound of formula (I) or (II) or the active agent is in the range of about 10 µg to about 250 mg (more typically about 100 µg to about 25 mg) per kilogram body weight of the subject per day. Where the compound of formula (I) or (II) or the active agent is a salt, an ester, an amide, a prodrug, or the like, the amount administered is calculated on the basis of the parent compound and so the actual weight to be used is increased proportionately.

Kits

One aspect of the invention pertains to a kit comprising (a) a compound of formula (I) or (II), or a composition comprising a compound as defined in any one of formula (I) or (II), e.g., preferably provided in a suitable container and/or with suitable packaging; and (b) instructions for use, e.g., written instructions on how to administer the compound or composition.

The written instructions may also include a list of indications for which the compound of formula (I) or (II) is a suitable treatment.

In one embodiment, the kit further comprises (c) a second active agent, or a composition comprising the second active agent. Here, the written instructions may also include a list of indications for which the second active agent, together with the compound of formula (I) or (II), is suitable for treatment.

Routes of Administration

A compound of formula (I) or (II), a second agent, or a pharmaceutical composition comprising the compound of formula (I) or (II), or the second agent may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject/patient may be any of its forms of development, for example, a foetus.

In one preferred embodiment, the subject/patient is a human.

It is also envisaged that the invention may be practised on a non-human animal having a microbial infection. A non-human mammal may be a rodent. Rodents include rats, mice, guinea pigs, chinchillas and other similarly-sized small rodents used in laboratory research.

Methods of Preparation

Compounds of formula (I) and (II) can be prepared by conventional peptide synthesis, using methods known to those skilled in the art. Suitable methods include solution-phase synthesis such as described by Yamada et al, *J. Peptide Res.* 64, 2004, 43-50, or by solid-phase synthesis such as described by de Visser et al, *J. Peptide Res*, 61, 2003, 298-306, and Vaara et al, *Antimicrob. Agents and Chemotherapy,* 52, 2008. 3229-3236. These methods include a suitable protection strategy, and methods for the cyclisation step. Alternatively, compounds may be prepared from readily available polymyxins, for example by removal of the N-terminal amino acid of the polymyxin (residue 1). Such a method is described herein for the preparation of compounds based on residues 2-10 of polymyxins B and E.

As shown herein, it is possible to derivatise the N terminal group of a deacylated polymyxin compound, such as deacylated polymyxin B and deacylated polymyxin B nonapeptide, without derivatising the amino groups that are present in the side chains of the polymyxin compound. As described herein, the side chains of the polymyxin compound may be selectively protected without protecting the N terminal group. The N terminal group may then be reacted to provide the appropriate N terminal substituent. The side chain protection may subsequently be removed.

A protected Polymyxin can also be cleaved to the corresponding heptapeptide by cleavage of amino acids 1-3. Methods for this cleavage are described in WO 2012/168820, and WO 1988/00950. As shown herein this can be derivatised by coupling to appropriately substituted dipeptides or tripeptides to provide novel polymyxin derivatives.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. Where technically appropriate embodiments may be combined and thus the disclosure extends to all permutations and combinations of the embodiments provided herein.

Certain aspects and embodiments of the invention will now be illustrated by way of example and with reference to the figures described above.

ABBREVIATIONS

| Abbreviation | Meaning |
| --- | --- |
| PMBN | Polymyxin B nonapeptide |
| PMB | Polymyxin B |
| Thr | Threonine |
| Ser | Serine |
| DSer | D-serine |
| Leu | Leucine |
| Ile | Isoleucine |
| Phe | Phenylalanine |
| Dphe | D-phenylalanine |
| Val | Valine |
| Dab | α,γ-Diaminobutyric acid |
| DIPEA | N,N-diisopropylethylamine |
| BOC-ON | 1-(Boc-oxyimino)-2-phenyl acetonitrile |
| EDC | 1-ethyl-3-(3-octaminopropyl)carbodiimide hydrochloride |
| PyBOP | (Benzotriazol-1-yl-oxy)tripyrrolidinophosphonium hexafluorophosphate |
| HATU | 2-(7-aza-1H-benzotriazol-1-yl)-1,1-3,3-tetramethyluronium hexafluorophosphate |
| HOAt | 1-Hydroxy-7-azabenzotriazole |
| DCM | Dichloromethane |
| TFA | Trifluoroacetic acid |
| ND | Not determined |
| N/A | Not applicable |
| DMF | N,N-Dimethylformamide |
| PMBH | Polymyxin B heptapeptide (4-10) |
| PMBD | Polymyxin B decapeptide |
| Pro | Proline |
| Dap | α,β-Diaminopropionic acid |
| Gly | Glycine |
| Thr | Threonine |
| His | Histidine |
| Phe | Phenylalanine |

EXAMPLES

The following examples are provided solely to illustrate the present invention and are not intended to limit the scope of the invention, as described herein.

Nomenclature-Compounds are named based on the natural polymyxin core from which they are synthetically derived.

Synthesis Examples

Intermediate 1—Polymyxin B Nonapeptide

A mixture of EDTA (1.4 g), potassium chloride (1.1 g) and L-cysteine (0.12 g) was dissolved in water (475 mL) and potassium phosphate buffer (pH 7, 25 mL). The reaction was stirred at 37° C. for 10 min then Polymyxin B (10.3 g) was added. After stirring for 2 h at 37° C. papain (3.36 U/mg) was added and stirred for a further 18 h at 37° C. The progress of the reaction was monitored by LC-MS using the conditions outlined in Table 1. The crude material was separated into 87 mL fractions and purified using 10 g SCX cartridge (×6), eluting first with methanol (100 mL) and then 20% ammonia (aq, sp.g.880) in methanol (100 mL). The ammonia fractions were isolated and evaporated to give the product as beige solid, yield 4.95 g, 60% m/z 482, $[M+2H]^{2+}$.

Intermediate 3—Colistin (Polymyxin E) Nonapeptide

Colistin (polymyxin E, 5 g) was treated with immobilised papain (185 ELU/g), potassium phosphate buffer (25 mM; pH 7, 1.25 L), potassium chloride (30 mM), EDTA (10 mM) and cysteine (1 mM) at 37° C. for 32 h with gentle agitation to produce colistin (polymyxin E) nonapeptide. The progress of the reaction was monitored by LC-MS using the conditions outlined in Intermediate 1, Table 1. The immobilised papain was removed by filtration and the filtrate was concentrated in vacuo to leave a solid residue which was re-suspended in 10% aqueous methanol and left at room temperature overnight. The supernatant was decanted and concentrated in vacuo. Colistin (Polymyxin E) nonapeptide was purified from the residue by SPE on C18 silica (10 gm), eluting with 0-25% aqueous methanol. Evaporation of the appropriate fractions gave the product as a white solid. m/z 465.32 $[M+2H]^{2+}$.

TABLE 1

LC-MS conditions

Micromass Platform LC

| | |
|---|---|
| Column: | Zorbax 5μ C18 (2) 150 × 4.6 mm |
| Mobile Phase A: | 10% Acetonitrile in 90% Water, 0.15 %TFA or 0.1% formic |
| Mobile Phase B: | 90% Acetonitrile in 10% Water, 0.15 %TFA or 0.1% formic |
| Flow rate: | 1 mL/min |

| | | | | | |
|---|---|---|---|---|---|
| Gradient: | Time 0 min | 100% | A | 0% | B |
| Time 10 min | | 0% | A | 100% | B |
| Time 11 min | | 0% | A | 100% | B |
| Time 11.2 min | | 100% | A | 0% | B |
| Time 15 min | | 100% | A | 0% | B |
| Cycle time 15 min | | | | | |
| Injection volume: | 20 μL | | | | |
| Detection: | 210 nm | | | | |

Intermediate 2—Tetra-(Boc) Polymyxin B Nonapeptide

Selective BOC protection of the free γ-amino groups on the Dab residues of polymyxin B nonapaptide was carried out using the procedure of H. O'Dowd et al, *Tetrahedron Lett.*, 2007, 48, 2003-2005. Polymyxin B Nonapeptide (Intermediate 1 1.00 g, 1.0 mmol) was dissolved in water (4.4 mL), dioxane (4.4 mL), triethylamine (4.4 mL) and the mixture was stirred for 10 min prior to the addition of 1-(Boc-oxyimino)-2-phenyl acetonitrile (Boc-ON) (0.77 g; 3.11 mmol). After stirring for 18 h, a further addition of Boc-ON (0.1 g, 0.4 mmol) was added and the mixture was stirred for a further 3 h. The progress of the reaction was followed by LC-MS, once complete the mixture was quenched by the addition of 20% methanolic ammonia (50 mL). The mixture was then evaporated to dryness and re-dissolved in methanol which was subsequently loaded onto silica. The crude material was purified using chromatography (eluent 0-20% methanol in dichloromethane) on silica gel (40 g) to afford tetra-(Boc) polymyxin B nonapeptide as a white solid (0.5 g, 36%). TLC, $R_f$ 0.2 (10% methanol in dichloromethane). m/z 1362.8[MH]$^+$.

Intermediate 4—Tetra-(Boc) Colistin (Polymyxin E) Nonapeptide

Colistin (Polymyxin E) Nonapeptide (2.5 g, 2.69 mmol) was suspended in water (35 mL) with sonication. Dioxane (35 mL) and triethylamine (35 ml) were added and the mixture was cooled in ice for 10 min prior to the addition of 1-(Boc-oxyimino)-2-phenyl acetonitrile (Boc-ON) (2.65 g; 10.76 mmol). The progress of the reaction was followed by LC-MS and reached completion after 10 minutes, whereupon the mixture was quenched by addition of 20% methanolic ammonia (25 mL). The liquid phase was decanted and the residual solid was re-dissolved in water and extracted sequentially with dichloromethane and iso-butanol. Based on LC-MS analysis, the decanted liquid and both dichloromethane and iso-butanol extracts were pooled together followed by concentration in vacuo to give yellow gum which was loaded onto flash chromatography (Si 60A-35-70). The column was eluted with 0-20% methanol (containing 2% ammonia) in dichloromethane. The column fractions eluted with 7-10% methanol (containing 2% ammonia) in dichloromethane afforded tetra-(Boc) colistin (polymyxin E) nonapeptide as a white solid (1.18 g, 33%). m/z 1329.7 [M+H]$^+$.

Intermediate 5—Tri-(Boc) Polymyxin B Heptapeptide

PMB sulphate (2 g) was dissolved in water (20 mL) followed by addition of 1,4 dioxane (40 mL) and left to stir for 10 minutes at room temperature. To the reaction mixture was added Boc anhydride (4.42 g) was added as solid and the reaction was stirred at room temperature and was monitored by HPLC. The reaction mixture was then adjusted to pH 6 using 1 M HCl, the precipitate which formed was filtered and washed with water (50 mL) and heptane (50 mL), to leave $Boc_5PMB$ as a white solid (2.4 g, 85%). This material (1 g) was dissolved in 1,4-butanediol (112.5 mL) and the mixture was stirred at 40° C. overnight. To the solution potassium phosphate (75 mL, 0.12 5M pH 8.0) was added over one minute, causing the formation of a white suspension. The reaction was diluted by adding 112.5 mL butanediol and 75 mL potassium phosphate (0.125 M pH 8.0), but the white emulsion persisted. The temperature of the reaction was reduced to 37° C. and then Savinase 16 L (250 µL) was added and the reaction was stirred at room temperature overnight. As the reaction progressed the white emulsion cleared to form a transparent solution due to the formation of the more soluble $PMBH-Boc_3$. The reaction mixture was diluted with water (50 ml) and was then extracted with DCM (100 mL) The DCM layer was collected and evaporated in vacuo to afford a colourless oil. The resulting oil was diluted in 50% methanol (aq.) and was loaded onto four preconditioned 10 g Varian Bond Elut SCX cartridges and the flow through was collected. The cartridges were washed with two column volumes of 50% methanol (aq.) and then $PMBH-Boc_3$ was eluted from the column using two column volumes of 20% ammonia in methanol. The resulting eluent was evaporated to dryness in vacuo to afford purified $PMBH-Boc_3$ (610 mg). m/z 1062.6 $[M+H]^+$.

Intermediate 6—Penta-(Boc) Polymyxin B Decapeptide

PMB sulphate (2 g) was dissolved in 100 mM potassium phosphate pH 8.0 (500 mL approx.). To the solution, crude polymyxin acylase (extracted from *Pseudomonas* sp. M-6-3W) was added at a ratio of 0.0125 g enzyme: 1 g PMB. The reaction was stirred at 37° C. for 16 hours. The reaction mixture was then loaded onto Varian Bond Elut SCX resin (cartridges preconditioned according to manufacturer's instructions) and then the cartridges were washed with water. The de-acylated polymyxin decapeptide (PMB) was eluted from the SCX column using 20% ammonia in methanol and the resulting fractions were evaporated to dryness. (b) PMBD (2.2 g) was dissolved in water (10 mL) followed by addition of 1,4-dioxane (10 mL) and triethylamine (10 mL) with stirring at room temperature. To the reaction mixture Boc-ON (5 equiv.) was added as solid and the reaction was stirred at room temperature and was monitored by HPLC. $PMBD-Boc_5$ was purified by flash chromatography loading in DCM and then developing the column using a step gradient of $DCM:MeOH:NH_3$ of 100:0:0, 91:7:2, 88:10:2, 83:15:2 and 78:20:2. Fractions containing $PMBD-Boc_5$ were evaporated to dryness to afford a white powder (0.48 g, 15%). m/z 1563.8 $[M+H]^+$.

Intermediate 7—Thr(O-$^t$Bu) Tetra-(N-Boc) Polymyxin B Nonapeptide

Step 1—(S)-2-((S)-2-Benzyloxycarbonylamino-3-tert-butoxy-butyrylamino)-4-tert-butoxycarbonylamino-butyric acid methyl ester To a stirred suspension of (S)-2-Benzyloxycarbonylamino-3-tert-butoxy-butyric acid DHCA salt (3.65 g, 7.4 mmol) and (S)-2-Amino-4-tert-butoxycarbonylamino-butyric acid methyl ester HCl salt (2.0 g, 7.4 mmol) in a mixture of DCM (60 mL) and DMF (120 mL) was added N,N-diisopropylethylamine (3.85 mL, 22.1 mmol). To this stirred mixture was added 1-hydroxy-7-azabenzotriazole (1.0 g, 7.3 mmol) followed by N-(3-dimethylaminopropyl)-N'-ethylcarbodiimide HCl salt (1.42 g, 7.4 mmol). The mixture was stirred for 17 h at ambient temperature then filtered under suction to remove the insoluble by-product, which was discarded. The filtrate was concentrated to a yellow oil which was partitioned between a solvent mixture of $EtOAc/Et_2O$ (1:1) (250 mL) and 0.5 M hydrochloric acid (200 mL). The aqueous phase was re-extracted with fresh solvent mixture (100 mL) and the combined organic extracts were successively washed with water (150 mL) and sat. $NaHCO_3$ solution (150 mL), dried ($Na_2SO_4$) and concentrated to a colourless oil (3.72 g). This oil was purified by silica gel chromatography on a 100 g SepPak cartridge, eluting with a solvent gradient of EtOAc/i-hexane (0-70%). Fractions containing the product ($R_f$ 0.26 in EtOAc/i-hexane 3:7, visualized with $KMnO_4$ spray) were pooled and concentrated to give the title compounds as a colourless foam (3.58 g, 6.8 mmol, 92% yield). m/z 524 ($MH^+$, 100%).

Step 2—(S)-2-((S)-2-Benzyloxycarbonylamino-3-tert-butoxy-butyrylamino)-4-tert-butoxycarbonylamino-butyric acid A solution of lithium hydroxide monohydrate (0.861 g, 20.5 mmol) in water (16 mL) was added to a stirred solution of (S)-2-((S)-2-Benzyloxycarbonylamino-3-tert-butoxy-butyrylamino)-4-tert-butoxycarbonylamino-butyric acid methyl ester (3.58 g, 6.8 mmol) in methanol (64 mL) at ambient temperature and stirred for 19 h. To this solution was added 1M HCl (24 mL) resulting in a milky mixture (pH 1) which was quickly extracted with DCM (3×135 mL). The combined organic extract was dried ($Na_2SO_4$) and concentrated to give the title compound as a colourless foam (3.27 g, 6.4 mmol, 94% yield). M/z 532 [MNa]+, 1041 [2M+Na]+.

Step 3-$CbzHNPMBN(OBu)(Boc)_4$ (S)-2-((S)-2-Benzyloxycarbonylamino-3-tert-butoxy-butyrylamino)-4-tert-butoxycarbonylamino-butyric acid (1.73 g, 3.39 mmol) and Intermediate 5 (3.0 g, 2.8 mmol) were charged to a flask to which dry DCM (85 ml) and dry DMF (17 mL) were added with stirring. To the stirred solution was added N,N-diisopropylethylamine (1.46 ml, 8.4 mmol) and after stirring for 5 min., O-(7-azabenzotriazol-1-yl)-N,N,N'N'-tetramethyluronium hexafluorophosphate (1.29 g, 3.39 mmol) was added in a single portion. The mixture was sonicated for 2 minutes then left to stir at ambient temperature for 18 h. The reaction mixture was then evaporated and the residue re-evaporated from toluene (3×100 mL). The residue was dried under vacuum for 3 h to ensure removal of toluene. Water (50 ml) was added to this material and the mixture was rapidly stirred for 3 h with occasional sonication. The title compound was collected by suction filtration as a fine, white solid and washed with water (2×25 mL) then dried under vacuum for 15 h (4.6 g, 3.0 mmol, 100% yield). m/z 1554[MH+].

Step 4—Title Compound

The product from step 3 (5.41 g, 3.48 mmol), ammonium formate (6.6 g, 104.4 mmol) and 10% Pd—C (2.0 g) were charged to a flask under $N_2$. MeOH (270 mL) was added and the mixture was stirred under N₂ for 4.5 h. LCMS showed MH⁺ for product and loss of starting material. The mixture was filtered under suction through a pad of celite and washed through with MeOH (50 mL). The filtrate and washings were evaporated to a colourless oil which was partitioned between a solvent mixture of EtOAc/MeOH (4:1)(250 mL) and water (250 mL).

The aqueous phase was further extracted with the same, fresh solvent mixture (2×100 mL). The combined organic extracts were dried (Na₂SO₄) and evaporated to a colourless oil (~6 g). This material was purified by chromatography on silica gel (100 g SepPak column) eluting with a gradient of MeOH/EtOAc (0-4%). Fractions containing the product ($R_f$ 0.30 in EtOAc/MeOH/NH₄OH₈₈₀ 95:5:1, visualized with KMnO₄ spray) were pooled and evaporated to give the title compound as a crispy foam (4.0 g, 2.8 mmol, 81% yield). m/z 1420 [MH+].

Intermediate 8—Thr(O-ᵗBu) Penta-(N-Boc) Polymyxin B decapeptide

Prepared from Intermediate 7 and N-α-Z—N-γ-BOC-L-Dab using Method 2B followed by CBZ-deprotection following the method of Intermediate 7, step 4, to afford the title compound as a white foam in 83% yield. m/z 1620 [MH+].

Method 1—General Method of Preparation of Nonapeptide Amide Derivatives

Step 1. The corresponding carboxylic acid (5 equiv. with respect to the polymyxin substrate) was dissolved in dichloromethane (2 mL/mmol). N,N-Diisopropylethyalmine (5.0 equiv.) and 2-(1H-7-Azabenzotriazol-1-yl)-1,1,3,3-tetramethyl uronium hexafluorophosphate (HATU) (5.0 equiv.) were then added to the reaction mixture. After 30 min stirring at room temperature compound of intermediate 2 or intermediate 4 (1.0 equiv.) was added. After 16 h the completion of the reaction was confirmed by LC-MS and the reaction mixture was evaporated to dryness and purified using column chromatography on silica gel (eluent 0-10% methanol in dichloromethane). The appropriate fractions were concentrated to leave the product as a colourless oil (typical yield 58%).

Step 2. The product from Step 1 was dissolved in dichloromethane (20 mL/mmol). Trifluoroacetic acid (60 equiv.) was added and the mixture was stirred at room temperature for 16 h, after which time LC-MS confirmed completion of the reaction. The reaction mixture was concentrated in vacuo to leave the trifluoroacetate salt as a colourless oil. To this was added water (10 mL/mmol) and the mixture was sonicated for 5 min. To the resulting suspension was added 1 M NaHCO₃ until the mixture reached pH 9. The mixture was then passed through a 10 g C18 SPE column, eluting sequentially with 0, 40, 50, 60, 70, 80 and 100% aqueous methanol. Product-containing fractions were pooled and evaporated. The residue was suspended in water and 0.1 M H₂SO₄ added until pH 7 was reached. The solution was lyophilised overnight to afford the sulphate salt as a white solid. Compound purity was assessed by HPLC using the conditions outlined in Table 2.

TABLE 2

Analytical HPLC conditions

| Column: | Phenomenex Hyperclone 5μ C18 (2) 150 × 4.6 mm |
|---|---|
| Mobile Phase A: | 10% Acetonitrile in 90% Water, 0.15 %TFA |
| Mobile Phase B: | 90% Acetonitrile in 10% Water, 0.15 %TFA |
| Flow rate: | 1 mL/min |
| Gradient: | Time 0 min 100% A 0% B |
| | Time 10 min 0% A 100% B |
| | Time 11 min 0% A 100% B |
| | Time 11.2 min 100% A 0% B |
| Cycle time 15 min | |
| Injection volume: | 20 μL |
| Detection: | 210 nm |

Method 2—General Method of Preparation of Nonapeptide Amides

Step 1—The BOC protected nonapeptide was prepared using the conditions of Method 1. After completion if the reaction, the crude reaction mixture was adsorbed onto silica and chromatographed on a silica cartridge, eluting with 0-20% methanol in dichloromethane. Product-containing fractions were combined and evaporated to a white foam. The product thus obtained was re-purified by silica gel chromatography to obtain the product as a white foam.

Step 2—The purified product from Step 2 was dissolved in dichloromethane (2 mL), treated with TFA (1 mL) and the mixture stirred at room temperature for 1 hour. The solvent was evaporated and the residue azeotroped with toluene, to leave a white solid. This was dissolved in water (10 mL) and washed with dichloromethane (5 mL). The aqueous phase was evaporated to low volume and lyophilised overnight to afford the TFA salt of the product as a white solid.

Method 2A—Further General Method of Preparation of Nonapeptide Amides

Step 1—The protected polymyxin substrate (0.07 mmol) was dissolved in dichloromethane (4 mL), and treated with the corresponding carboxylic acid (1.5 equiv. with respect to the polymyxin substrate), N,N-Diisopropylethyalmine (3.0 equiv.), followed by HATU (2.0 equivalent). After 16 h the completion of the reaction was confirmed by LC-MS and the reaction mixture was evaporated to dryness. Water (~10 mL) was added and the mixture triturated then stirred vigorously for 1 h. The resultant precipitate was collected by filtration and dried in vacuo overnight.

Step 2—The Boc-protected derivative from Step 1 was dissolved in dichloromethane (3 mL) and treated with TFA (1 mL). The reaction mixture was stirred at room temperature until LCMS confirmed complete deprotection. The solvent was evaporated and the residue chromatogaphed by prep HPLC using the conditions of Method 3, step 6. Product-containing fractions were combined, evaporated to low volume, and lyophilised to afford the product as the TFA salt.

Method 3—General Method for the Preparation of Dipeptide Amide Derivatives of Polymyxin B Heptapeptide Step 1—Coupling of Carboxylic Acids to Methyl Esters of Amino Acid 1

The appropriate carboxylic acid (1.1 equiv.), the appropriate (N-Boc or OBuᵗ) amino acid methyl ester hydrochloride (1 equiv.), EDC hydrochloride (1.1 equivs.) and HOAt (1.1 equiv.) were charged to a flask. DCM (8 mL/mmol with respect to the amino acid methyl ester) was added and to the stirred mixture under nitrogen was added DIPEA (3 equiv.) to give a yellow solution. The solution was stirred for 18 h, diluted with an equal volume of DCM and the solution washed successively with water (16 mL/mmol with respect to amino acid) and sodium hydrogen carbonate solution (16 mL/mmol). The solution was dried (Na₂SO₄) and evaporated to a residue. The residue was purified by chromatography on silica gel (gradient elution with EtOAc/isohexane). Relevant fractions were pooled and evaporated to afford the desired methyl ester product (m/z [M+H]$^+$ detectable in the LCMS spectrum). Where a racemic acid is used, the product is obtained as a mixture of diastereoisomers.

Step 2—Hydrolysis of the Methyl Ester Product from Step 1

To a stirred solution of the product from step 1 (1 equiv.) in methanol (5 mL/mmol with respect to the methyl ester) was added a solution of lithium hydroxide monohydrate (3 equiv.) in water (0.5 mL/mmol of reagent). The resulting solution was stirred at ambient temperature for 24 h then poured into water (25 mL/mmol with respect to methyl ester). This solution was adjusted to pH 1 by the addition of 1 M hydrochloric acid (3 equiv.) and the mixture was extracted with DCM (3×). The combined organic extracts were dried (Na$_2$SO$_4$) and evaporated to afford the desired carboxylic acid (m/z [M+H]$^+$ detectable in the LCMS spectrum). Where a racemic acid is used in step 1, the product is obtained as a mixture of diastereoisomers.

Step 3—Coupling of the Carboxylic Acid Product from Step 2 with the Methyl Ester of Amino Acid 2

This step was carried out in the same manner as that described in step 1, using the carboxylic acid from step 2 and the appropriate (N-Boc or OBu$^t$) amino acid methyl ester hydrochloride. The methyl ester product (m/z [M+H]$^+$ detectable in the LCMS spectrum) was isolated as described in step 1. Where a racemic acid was used in step 1, the product is obtained as a mixture of diastereoisomers.

Step 4—Hydrolysis of the Methyl Ester Product from Step 3

This step was carried out in the same manner as that described in step 2, using the methyl ester from step 3. The carboxylic acid product (m/z [M+H]$^+$ detectable in the LCMS spectrum) was isolated as a mixture of diastereoisomers.

Step 5—Coupling of the Carboxylic Acid Product from Step 4 with Tri-(Boc) Polymyxin B Heptapeptide (Intermediate 5)

PyBoP (2 equiv.) was added to a stirred solution of the carboxylic acid from step 4 (2 equiv.) in dry DCM (15 mL/mmol with respect to acid). DIPEA (2 equiv.) was then added and the solution stirred for 30 min. To this solution was then added a solution of Intermediate 5 (1 equiv.) in dry DCM (12 mL/mmol with respect to acid) and dry DMF (1.5 mL/mmol with respect to acid) and the whole mixture was stirred for 16 h. The mixture was then evaporated to a thick oil which was partitioned between EtOAc and water. The organic phase was washed with saturated sodium hydrogen carbonate solution then brine, dried (Na$_2$SO$_4$) and evaporated to a foam. The material was purified by chromatography on silica gel (gradient elution with MeOH/EtOAc) to afford the polypeptide product (m/z [M+H]$^+$ detectable in the LCMS spectrum). Where a racemic acid was used in step 1, the product is obtained as a mixture of diastereoisomers.

Step 6—Deprotection of the Polymyxin B Heptapeptide Product from Step 5

TFA (30 mL/mmol with respect to polypeptide) was added to a stirred solution of the polypeptide from step 5 in DCM (60 mL/mmol). The solution was stirred for 3.5 h then evaporated and dried under vacuum for 1 h. The residue was purified by HPLC (conditions below) and lyophilised to afford the TFA salt of the product as a white solid. Where a racemic acid was used in step 1, the product is obtained as a mixture of diastereoisomers. (See Table 4 for examples).

TABLE 3

| Prep HPLC conditions | |
|---|---|
| Column: | Sunfire C18 OBD 5 µm × 30 mm × 150 mm |
| Mobile Phase A: | Acetonitrile + 0.15%TFA |
| Mobile Phase B: | water + 0.15%TFA |
| Flow rate: | 25 mL/min |

| Gradient: | Time 0 min | 3% | A | 97% | B |
|---|---|---|---|---|---|
| Time 2 min | | 3% | A | 97% | B |
| Time 25 min | | 40% | A | 60% | B |
| Time 30 min | | 97% | A | 3% | B |
| Time 32 min | | 97% | A | 3% | B |
| Detection: | 210 nm | | | | |

Method 3A

The coupling was carried out as described in Method 3, using a CBZ-protected amino acid at Step 3. An additional CBZ deprotection step (Step 5A) was included prior to step 6.

Step 5A—CBZ Deprotection:

A mixture of the protected intermediate from Step 5 (0.0573 mmol) and 10% Pd/C paste (10 mg) in ethanol (4 mL) was stirred under an atmosphere of hydrogen for 18 h. Further 10% Pd/C paste (10 mg) was added and stirring was continued for a further 24 h. The reaction mixture was filtered through a pad of celite and the filtercake was washed with ethanol (2×). The combined organics were evaporated to afford a crude oil. This was purified by reverse phase preparatory HPLC using the conditions of Method 3 step 6 to afford the desired product as a colourless glass (20%). (m/z [M+H]$^+$ detectable in the LCMS spectrum).

Method 3B

Method 3B consists of steps 1-2 of Method 3A followed by coupling to BOC-protected PMBN (Intermediate 2) to give the protected decapeptide. Deprotection following Method 3A, Step 5A for CBZ deprotection and Step 6 for Boc deprotection affords the desired compound, details given in Table 4.

The compounds were isolated as sulphate salts, unless otherwise indicated.

General Preparation of Acetate Salts

Acetate salts may be prepared if required, by the following protocol.

A TFA salt (50 mg) may be dissolved in water, and taken to pH 9 with 1 M NaHCO$_3$. The mixture may then passed through a 1 g C18 SPE column, eluting with water (20 mL) followed by 80% methanol/water. Product-containing fractions may be pool treated with 0.1 M acetic acid (10 equiv). The solution may be concentrated under reduced pressure, then lyophilised overnight to afford the acetate salt, typically as a white solid. Compound purity may eb assessed by HPLC using the conditions outlined in Table 2.

Synthesis of Carboxylic Acids

Carboxylic acids used for the assembly of polymyxin derivatives were secured either via commercial sources, or prepared using methods known to those skilled in the art. Alkyl substituted piperidine carboxylic acids, such as cis-4-Octyl piperidine 2-carboxylic acid used for example A43 were prepared according to the general method below:

General method of synthesis of alkyl substituted pyridine carboxylic acids:

Step 1. To a solution of the appropriate bromo pyridine carboxylic acid ethyl ester 5.0 (mmol) in ethyl acetate (20 mL) under nitrogen was added triethylamine (1.1 mL, 7.5 mmol), 1-octyne (1.1 mL, 7.5 mmol), bis(triphenylphosphine)palladium (II) dichloride (176 mg, 0.25 mmol) and copper iodide (10 mg, 0.05 mmol). The reaction mixture was stirred at 50 deg C. for 16 hours, then filtered under suction through Celite and washed through with ethyl acetate. The filtrate was evaporated at reduced pressure. The residue was purified by silica gel chromatography eluting with 0-50% ethyl acetate in iso-hexane to yield the corresponding oct-1-ynylpyridine carboxylic acid ethyl ester.

Step 2. To a solution of the oct-1-ynylpyridine carboxylic acid ethyl ester (4.60 mmol) in acetic acid (100 mL) was added platinum oxide (100 mg). The reaction mixture was hydrogenated for 16 h., then filtered under suction through Celite and washed through with ethyl acetate. The filtrate was evaporated at reduced pressure and then the residue was partitioned between ethyl acetate and water. The pH of the aqueous layer was adjusted to pH10 by the addition of 0.880 ammonia. After separation of the layers, the aqueous phase was re-extracted with ethyl acetate and then the combined organic layers were passed through a hydrophobic frit. The solvent was evaporated at reduced pressure and the residue purified by silica gel chromatography eluting with 0-100% (80:20:2 ethyl acetate:methanol:880 ammonia) in ethyl acetate to afford the reduced product.

Step 3. To a solution of the octylpiperidine carboxylic acid ethyl ester (3.20 mmol) in dichloromethane (50 mL) was added triethylamine (680 μL, 4.8 mmol), followed by di-tert-butyl dicarbonate (1.06 g, 4.8 mmol). The reaction mixture was stirred at room temperature for 16 hours and then concentrated at reduced pressure. The residue was dissolved in diethyl ether and washed with ammonium chloride solution. After separation of the layers, the aqueous phase was re-extracted with diethyl ether. The combined organic phases were dried (MgSO4), filtered and concentrated at reduced pressure. The products were purified by silica gel chromatography eluting with 0-30% diethyl ether in iso-hexane. Stereochemistry was assigned by comparison to compounds in the literature, e.g. Syn. Comm., 2008, 38, 2799.

Step 4. To a solution of the BOC protected material (0.89 mmol) in dioxane (5 mL) and water (2 mL) was added lithium hydroxide monohydrate (76 mg, 1.80 mmol). The reaction mixture was stirred at room temperature for 16 hours and then treated with a further quantity of lithium hydroxide monohydrate (100 mg) for 2 days. The reaction mixture was concentrated at reduced pressure and the residue partitioned between ethyl acetate and water. The aqueous phase was acidified by the addition of 1M hydrochloric acid and the product extracted into ethyl acetate. The organic phase was passed through a hydrophobic frit and the solvent evaporated at reduced pressure to yield the corresponding octyl piperidine carboxylic acid.

TABLE 4

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 1 | C51H88N14O13 | 1104.67 | 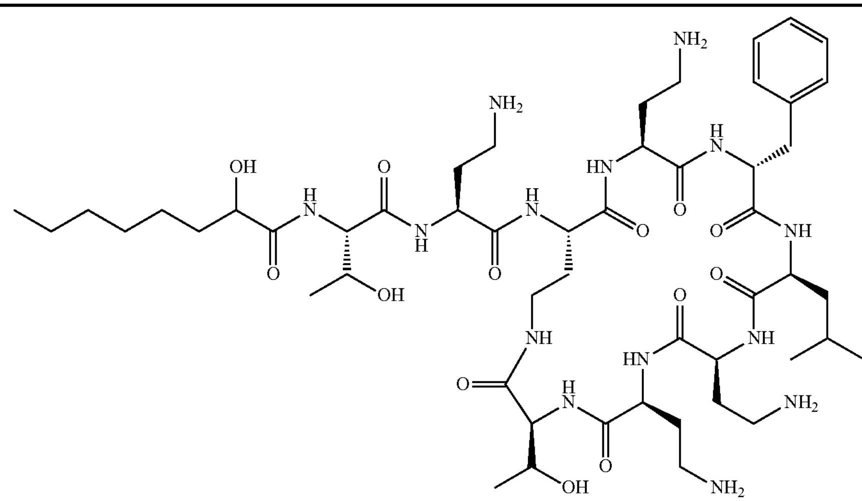 | 1 | Int. 2 | [2(R,S)-2-Hydroxyoctanoyl] polymyxin B nonapeptide | 5.93 | 1104.9 [MH]+ |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| 2 | C49H85N15O12 | 1075.65 | 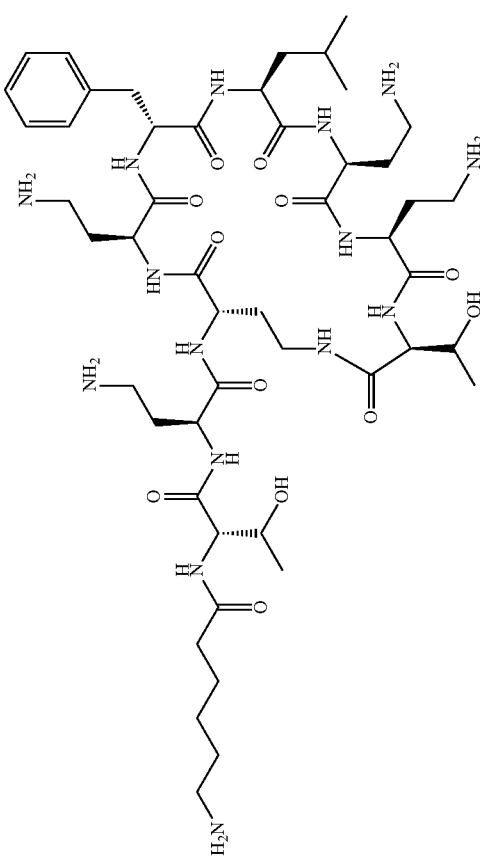 | 1 | Int. 2 | 6-Aminohexanoyl polymyxin B nonapeptide | 4.97 | 1077.15 [MH]+. |
| 3 | C46H79N15O12 | 1033.60 | 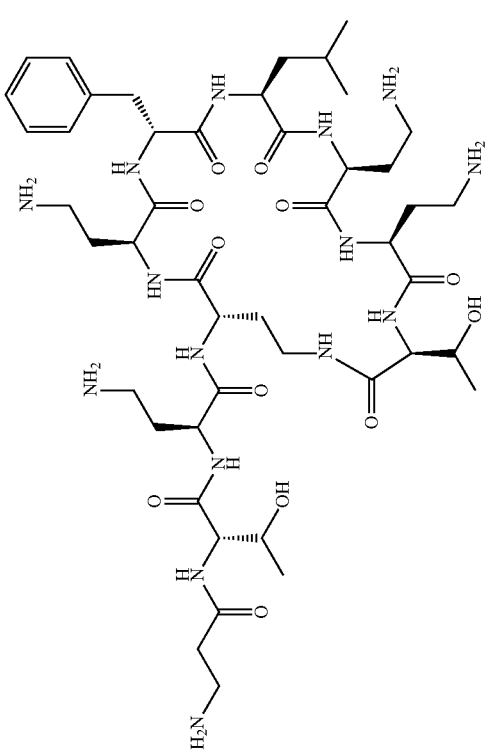 | 1 | Int. 2 | 3-Aminopropanoyl polymyxin B nonapeptide | 4.97 | 1034.42, [MH]+ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 4 | C47H81N15O12 | 1047.62 | 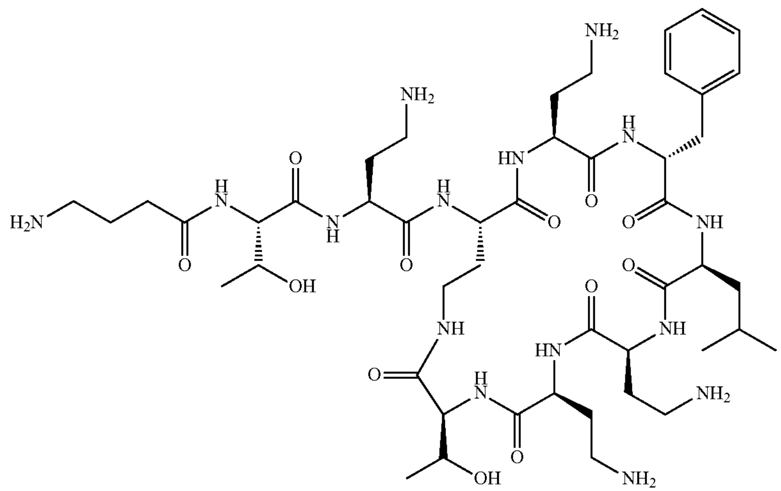 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCN)C(C)O)CCNC(=O)[C@H](C(C)O)NC(=O)[C@H](CCN)NC(=O)[C@H](CCN)NC1=O] | 1 | Int. 2 | 4-Aminobutanoyl polymyxin B nonapeptide | 4.97 | 524.91 [M + 2H]$^{2+}$. |
| 5 | C50H79N15O12 | 1081.60 | 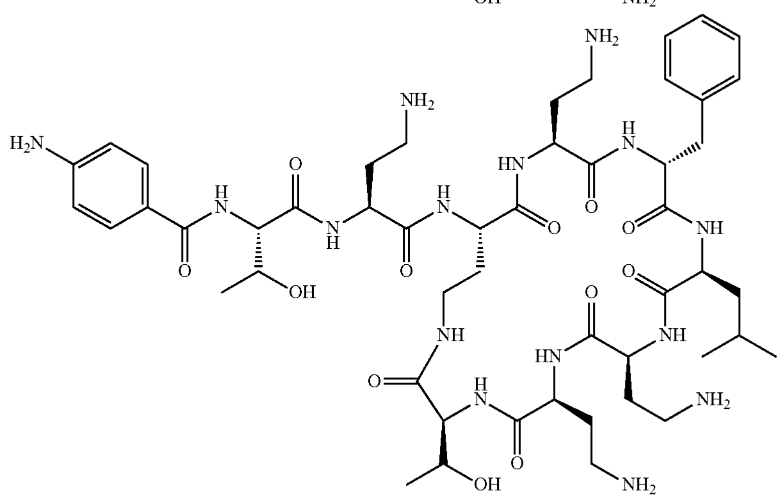 | 1 | Int. 2 | 4-Aminobenzoyl polymyxin B nonapeptide | 5.15 | 1081.7, [M]$^+$ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 6 | C48H83N15O12 | 1061.63 | 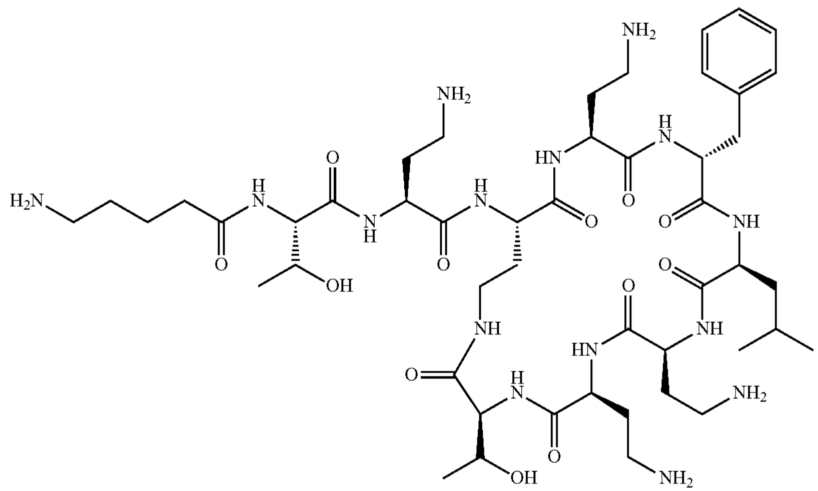 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCCCN)C(C)O)CCNC(=O)[C@H](C(C)O)NC(=O)[C@H](CCN)NC(=O)[C@H](CCN)NC1=O] | 1 | Int. 2 | 5-Aminopentanoyl polymyxin B nonapeptide | 5.09 | 1062.7 [MH]+ |
| 7 | C49H83N15O12 | 1073.63 | 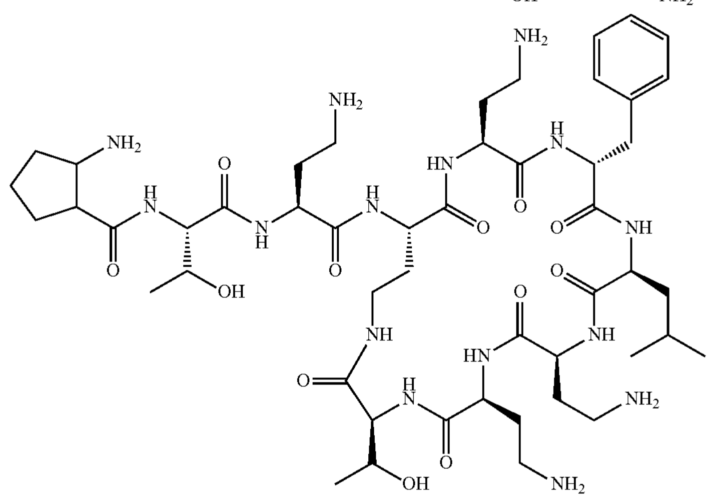 | 1 | Int. 2 | (1R,S/2R,S)-2-Aminocyclopentane-carbonyl polymyxin B nonapeptide | 5.07 | 1074.87, [MH]+. |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 8 | C45H76N14O13 | 1020.57 | 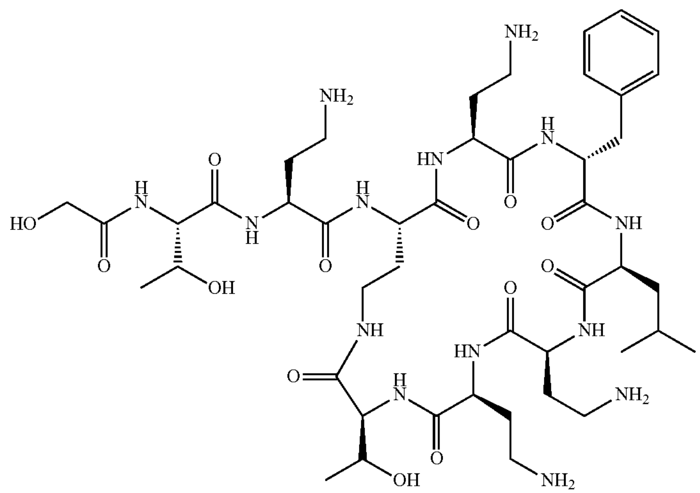 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CO)C(C)O)CCNC(=O)[C@H](C(C)O)NC(=O)[C@H](CCN)NC(=O)[C@H](CCN)NC1=O] | 1 | Int. 2 | Hydroxyacetyl polymyxin B nonapeptide | 5.00 | 1021.1 (MH+) |
| 9 | C48H81N15O12 | 1059.62 | 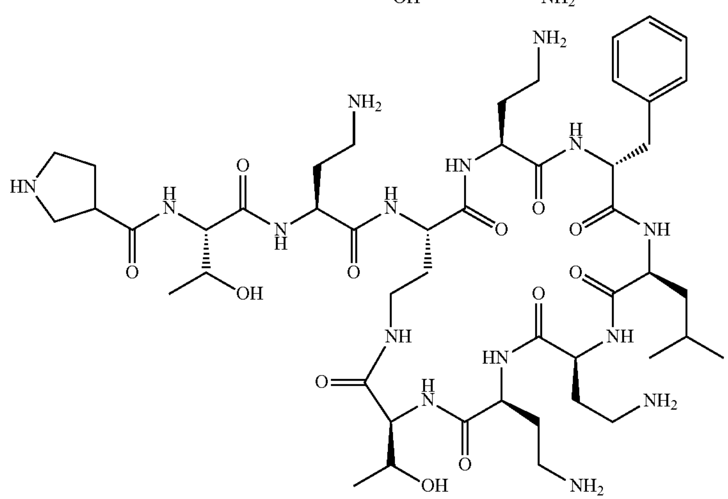 | 1 | Int. 2 | [3(R,S)-Pyrrolidine-3-carbonyl]polymyxin B nonapeptide | 4.91 | 1060.58 [MH]+ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 10 | C52H89N15O12 | 1115.68 | 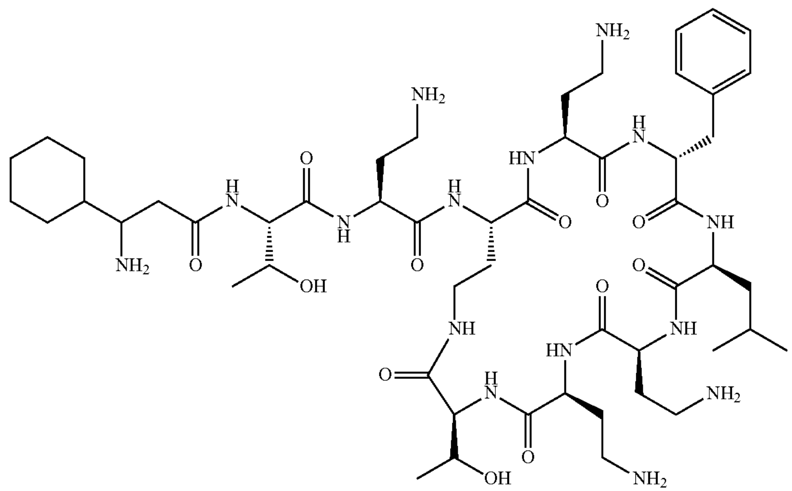 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CC(N)C2CCCCC2)C(C)O)CCNC(=O)[C@H](C(C)O)NC(=O)[C@H](CCN)NC(=O)[C@H](CCN)NC1=O] | 1 | Int. 2 | [3(R,S)-3-Amino-3-cyclohexane-propanoyl]Polymyxin B nonapeptide | 5.24 | 1116.78, [MH]+. |
| 11 | C49H85N15O12 | 1075.65 | 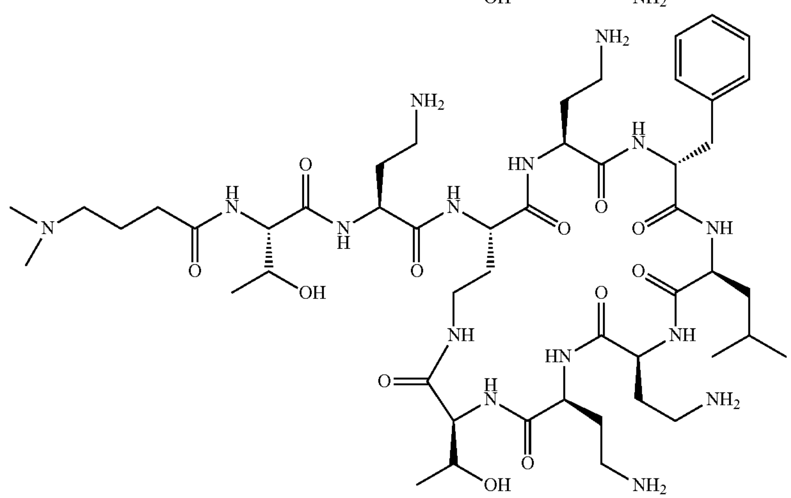 | 1 | Int. 2 | 4-(N,N-dimethylamino)-butanoyl polymyxin B nonapeptide | 4.92 | 1076 (MH+) |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| 12 | C50H85N15O14S | 1151.61 | 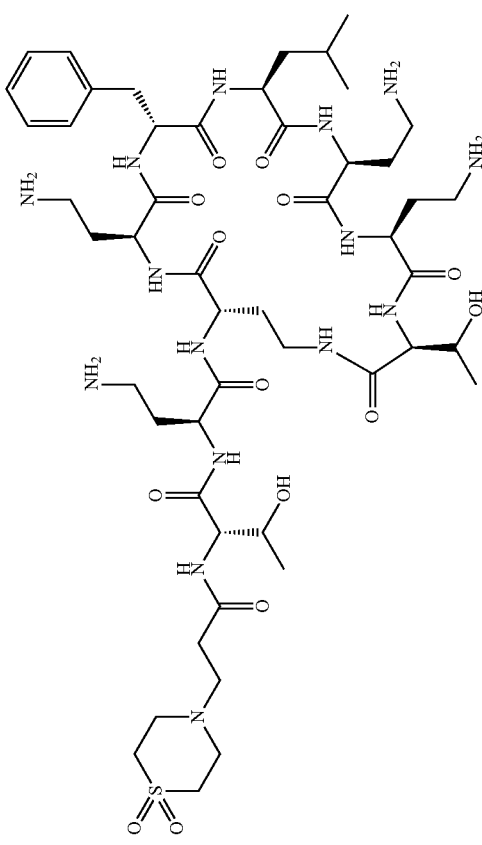 | 1 | Int. 2 | 3-(1,1-dioxo-thiomorpholine-4-yl)propanoyl Polymyxin B nonapeptide | 4.99 | 1052.7 (MH+) |
| 13 | C50H87N15O12 | 1089.67 | 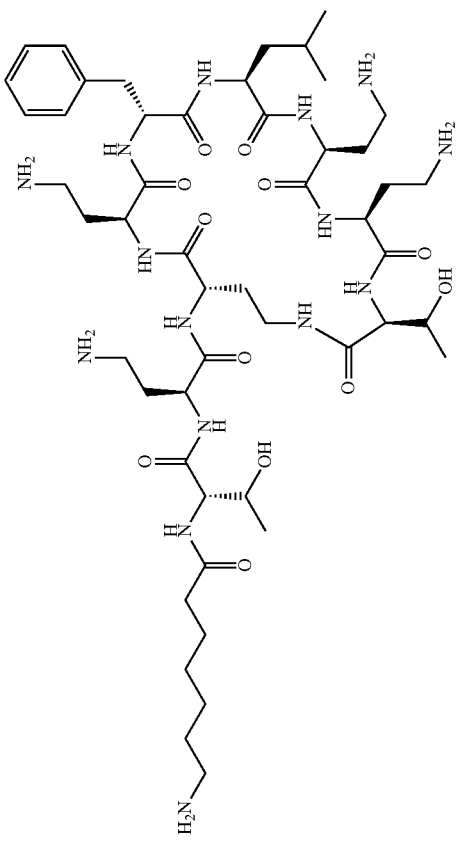 | 1 | Int. 2 | 7-Aminoheptanoyl polymyxin B nonapeptide | 4.75 | 1091.76 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 14 | C51H87N15O13 | 1117.66 | 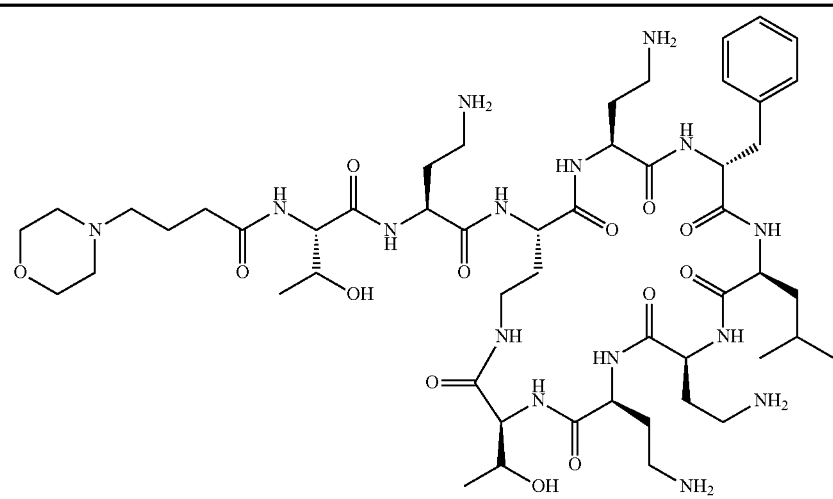 | 2 | Int. 2 | 4-Morpholinylbutanoyl polymyxin B nonapeptide, trifluoroacetate salt | 5.14 | 1118.6 (MH$^+$) |
| 15 | C47H80N14O13 | 1048.60 | 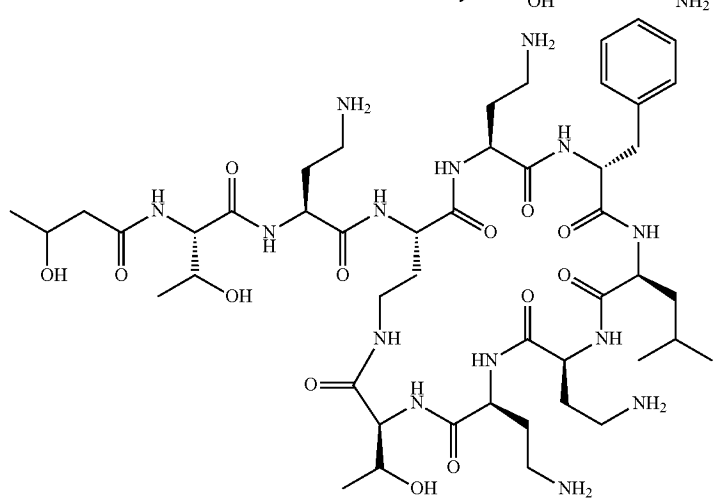 | 1 | Int. 2 | 3(RS)-3-Hydroxybutanoyl polymyxin B nonapeptide | 4.83 | 525.3 (M + 2H)$^{+2}$ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 16 | C48H83N15O12 | 1061.63 | 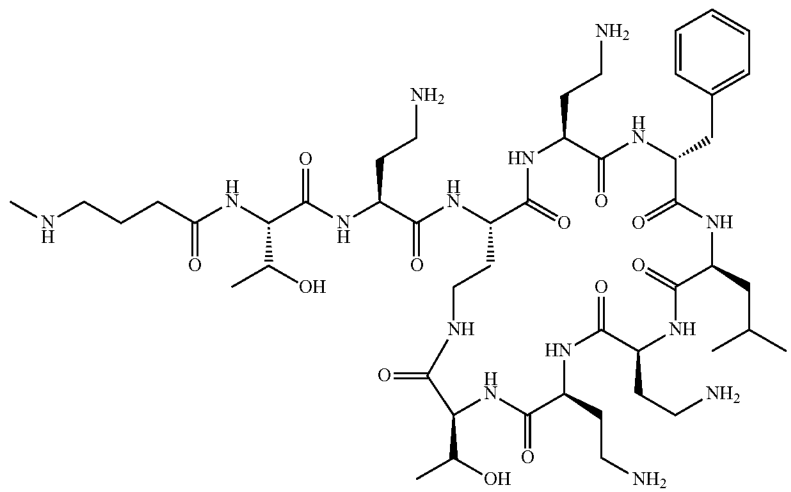 [SMILES: CNCCCC(=O)N[C@H](C(=O)N[C@@H](CCN)C(=O)N[C@H]1CCNC(=O)[C@H](C(C)O)NC(=O)[C@H](CCN)NC(=O)[C@H](CCN)NC(=O)[C@H](CC(C)C)NC(=O)[C@@H](Cc2ccccc2)NC(=O)[C@H](CCN)NC1=O)C(C)O] | 1 | Int. 2 | 4-(N-methylamino)-butanoyl polymyxin B nonapeptide | 4.92 | 1062.4 (MH+) |
| 17 | C50H85N15O12 | 1087.65 | 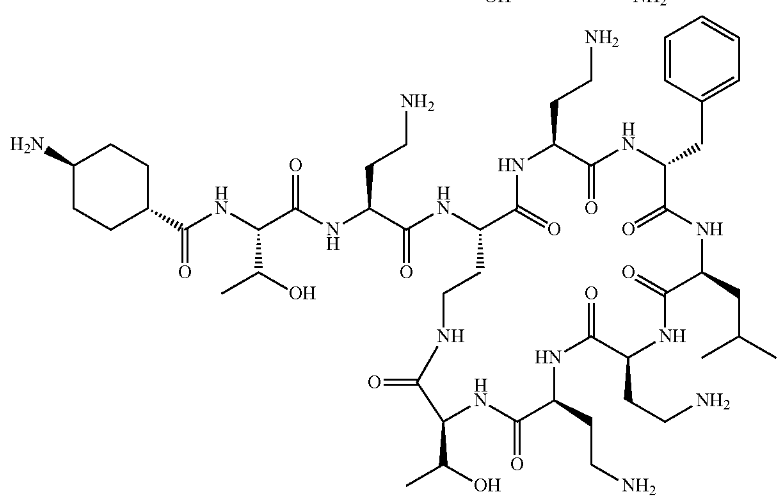 | 1 | Int. 2 | Trans-4-aminocyclohexane-carbonyl polymyxin B nonapeptide | 4.95 | 1087.1 (M+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 18 | C51H79BrN14O13 | 1176.5, 1174.5 | 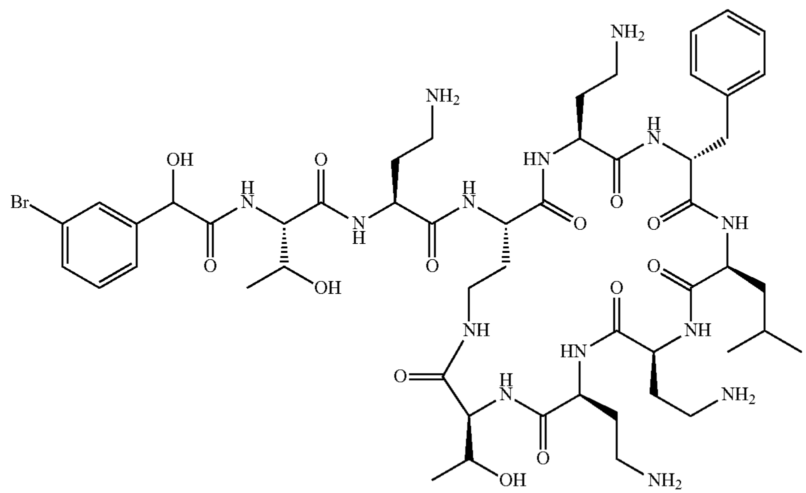 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)C(O)c2cccc(Br)c2)C(C)O)CCNC(=O)[C@H](C(C)O)NC(=O)[C@H](CCN)NC(=O)[C@H](CCN)NC1=O] | 1 | Int. 2 | 2-(R,S)-2-hydroxy-2-(3-bromophenyl) ethanoyl)3 polymyxin B nonapeptide | 5.71, 6.02 | 1177.9, 1176.10, [MH]+ |
| 19 | C48H90N14O13 | 1070.68 | 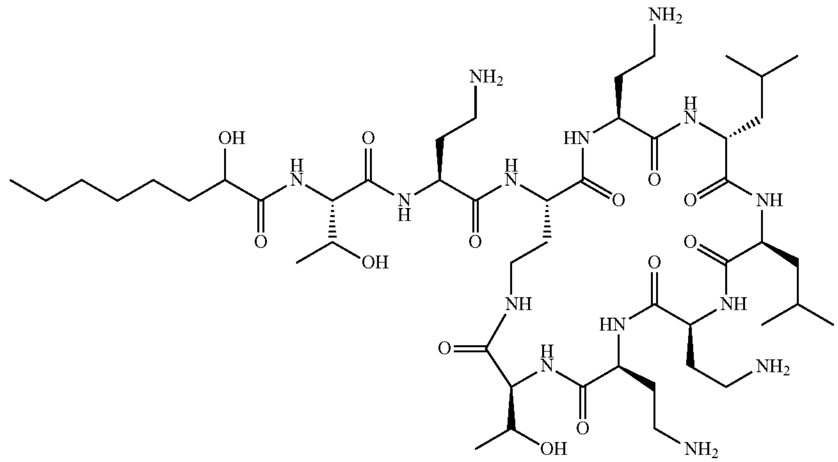 [SMILES: CCCCCCC(O)C(=O)N[C@H](C(=O)N[C@@H](CCN)C(=O)N[C@H]1CCNC(=O)[C@H](C(C)O)NC(=O)[C@H](CCN)NC(=O)[C@H](CCN)NC(=O)[C@H](CC(C)C)NC(=O)[C@@H](CC(C)C)NC(=O)[C@H](CCN)NC1=O)C(C)O] | 1 | Int. 4 | 2-(RS)-2-Hydroxyoctanoyl polymyxin E nonapeptide | 5.92 | 1071.3 [MH]+ |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| 20 | C50H85N15O12 | 1087.65 | 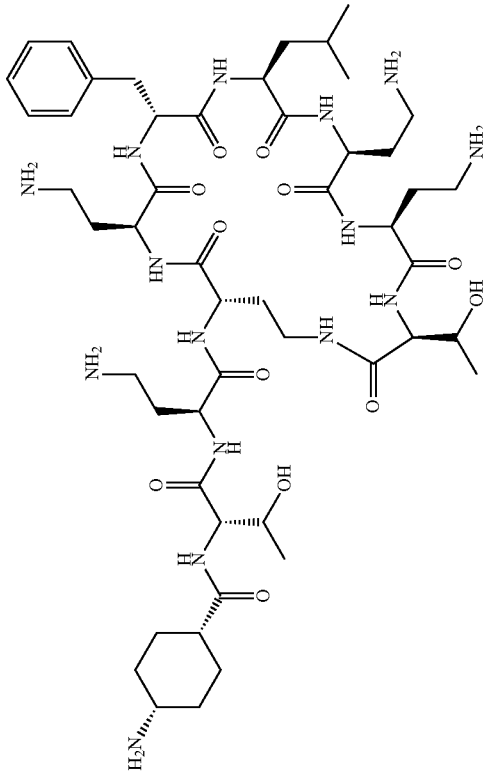 | 1 | Int. 2 | Cis-4-aminocyclohexane carbonyl polymyxin B nonapeptide | 5.27 | 1087.0 (M⁺) |
| 21 | C49H85N15O12 | 1075.65 | 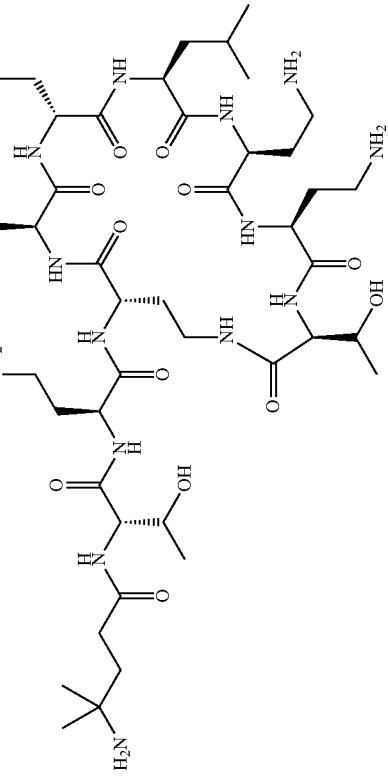 | 1 | Int. 2 | 4-Amino-4-methyl pentanoyl polymyxin B nonapeptide | 5.08 | 1076.3 (MH⁺) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 22 | C50H87N15O12 | 1089.67 | 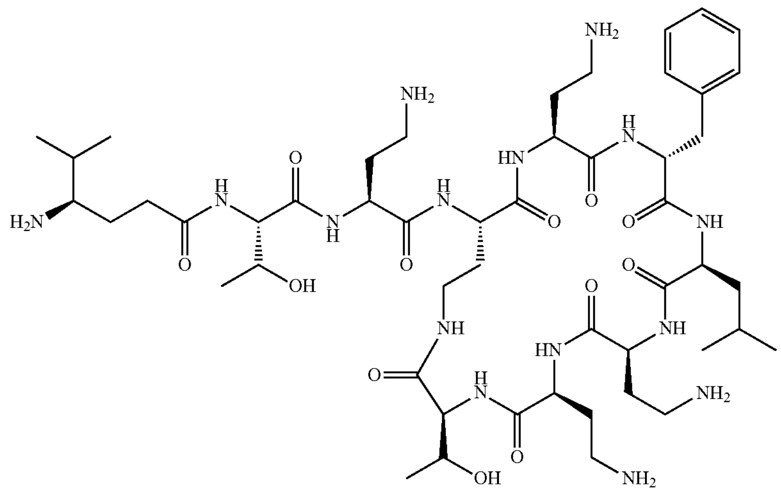 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CC[C@@H](N)C(C)C)C(C)O)CCNC(=O)[C@H](C(C)O)NC(=O)[C@H](CCN)NC(=O)[C@H](CCN)NC1=O] | 1 | Int. 2 | 4(R)-Amino-5-methylhexanoyl polymyxin B nonapeptide | 5.16 | 1089.6 (M⁺) |
| 23 | C50H85N15O12 | 1087.65 | 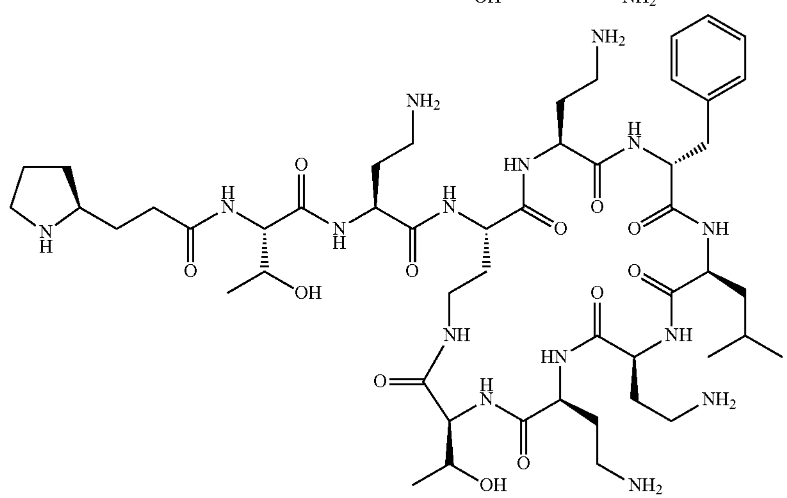 | 1 | Int. 2 | 3-(S)-(1-pyrrolidin-2-yl)-propionyl polymyxin B nonapeptide | 5.10 | 1087 (M⁺) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 24 | C48H83N15O12 | 1061.63 | 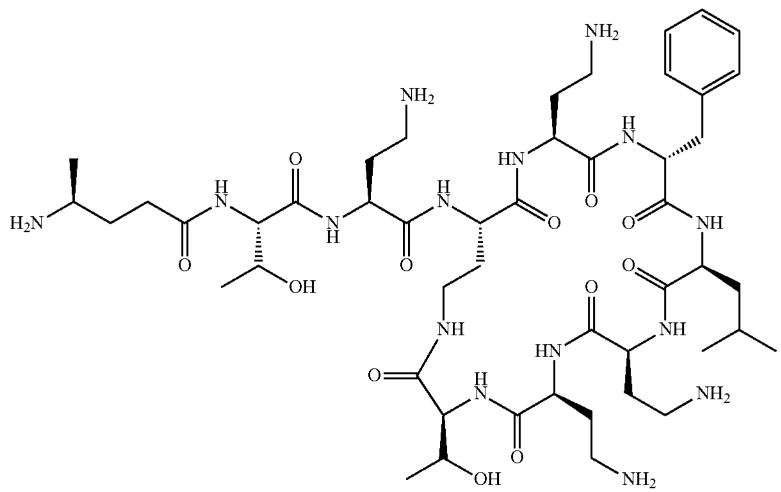 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CC[C@H](C)N)C(C)O)CCNC(=O)[C@H](C(C)O)NC(=O)[C@H](CCN)NC(=O)[C@H](CCN)NC1=O] | 1 | Int. 2 | 4S-aminopentanoyl polymyxin B nonapeptide | 5.07 | 1062.1 (MH+) |
| 25 | C50H84N14O13 | 1088.63 | 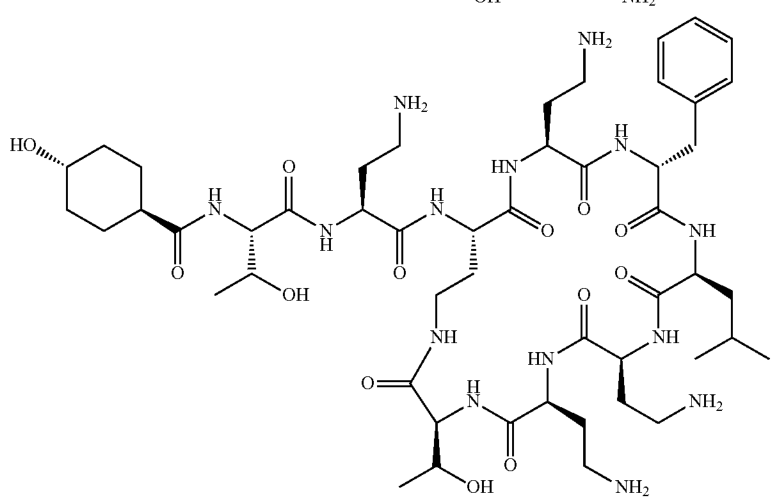 | 1 | Int. 2 | trans-4-hydroxycyclohexane carbonyl polymyxin B nonapeptide | 5.13 | 1088.7 (M+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 26 | C46H78N14O13 | 1034.59 | 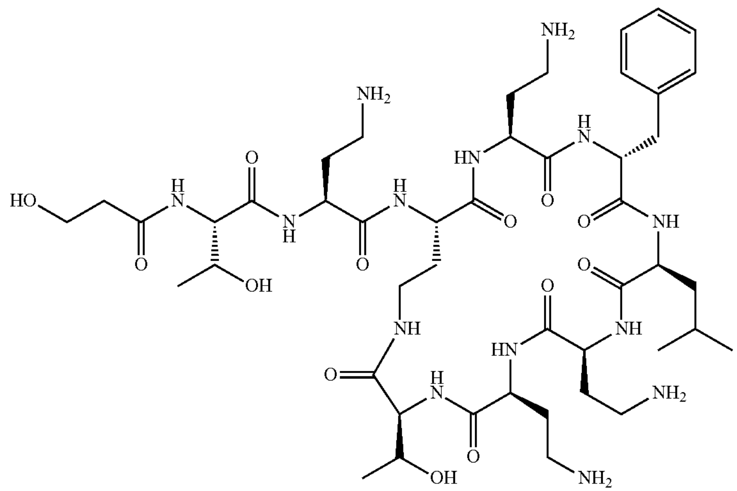 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CCO)C(C)O)CCNC(=O)[C@H](C(C)O)NC(=O)[C@H](CCN)NC(=O)[C@H](CCN)NC1=O] | 1 | Int. 2 | 3-Hydroxypropanoyl polymyxinB nonapeptide | 5.19 | 1034.3 (M+) |
| 27 | C51H86N14O13 | 1102.65 | 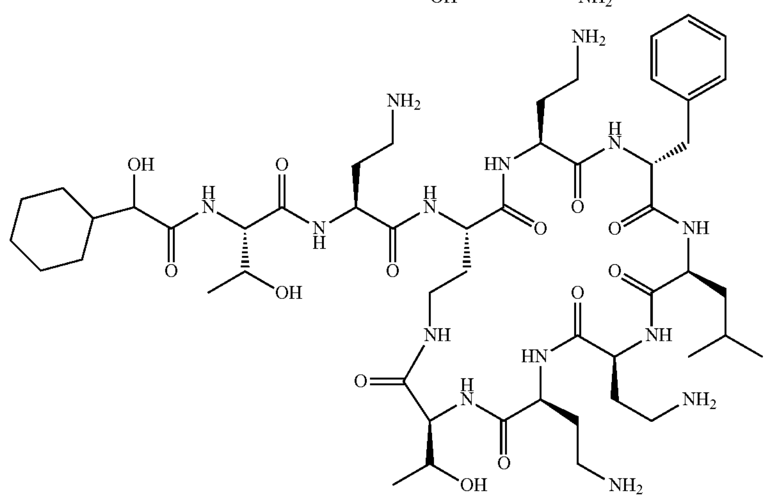 | 1 | Int. 2 | 2-(RS)-(2-Hydroxy-2-cyclohexyl)ethanoyl polymyxin B nonapeptide | 5.80, 6.01 | 1103.9 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 28 | C52H83N15O12 | 1109.63 | 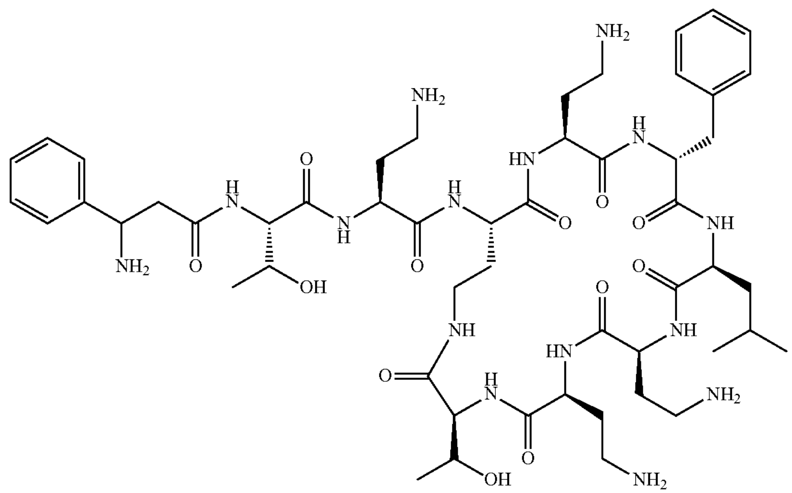 | 1 | Int. 2 | [3-(R,S)-3-Amino-3-phenylpropanoyl] Polymyxin B nonapeptide | 5.15, 5.27 | 1082.6 (MH+) |
| 29 | C49H83N15O12 | 1073.63 | 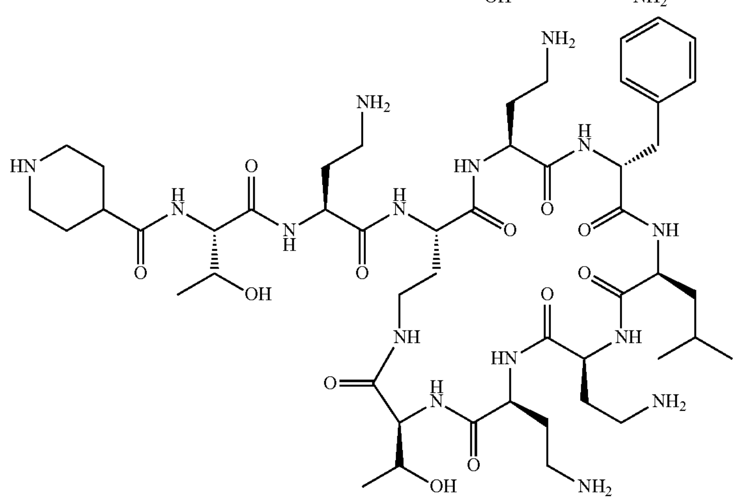 | 2 | Int. 2 | 4-piperidinecarbonyl polymyxin B nonapeptide, trifluoroacetate | 5.00 | 537.8 (M + 2H)$^{+2}$ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 30 | C49H91N15O12 | 1081.70 | 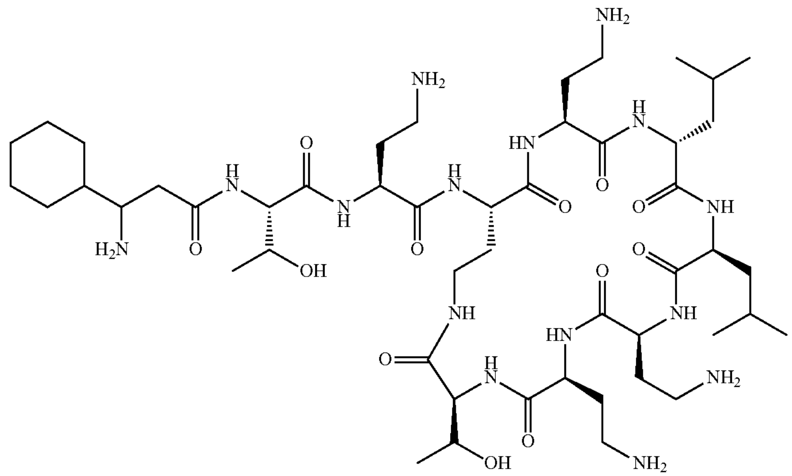 [SMILES: CC(C)C[C@@H]1NC(=O)[C@@H](CC(C)C)NC(=O)[C@H](CCN)NC(=O)[C@@H](NC(=O)[C@H](CCN)NC(=O)[C@@H](NC(=O)CC(N)C2CCCCC2)C(C)O)CCNC(=O)[C@H](C(C)O)NC(=O)[C@H](CCN)NC(=O)[C@H](CCN)NC1=O] | 2 | Int. 4 | 3(R,S)-3-Amino-3-cyclohexane-propanoyl]Polymyxin E nonapeptide, TFA salt | 5.15, 5.27 | 1082.6 (MH+) |
| 31 | C48H88N14O13 | 1068.67 | 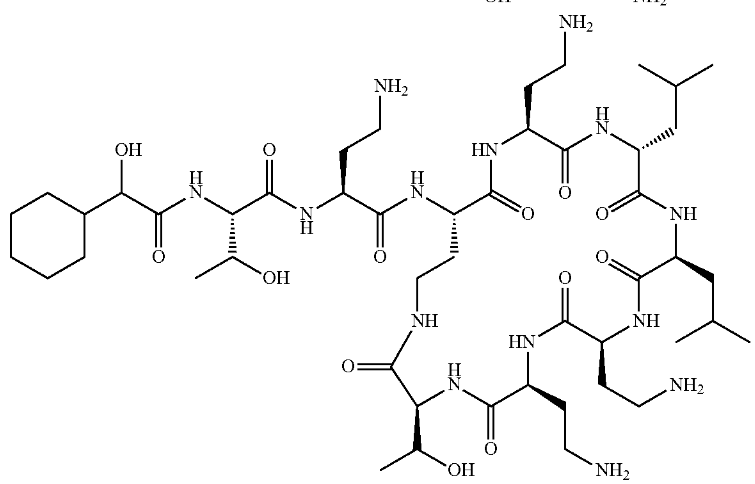 | 2 | Int. 4 | 2(RS)-(2-Hydroxy-2-cyclohexyl)ethanoyl polymyxin E nonapeptide, TFA salt. Isomer 1 | 5.89 | 1069.6 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 32 | C48H88N14O13 | 1068.67 | 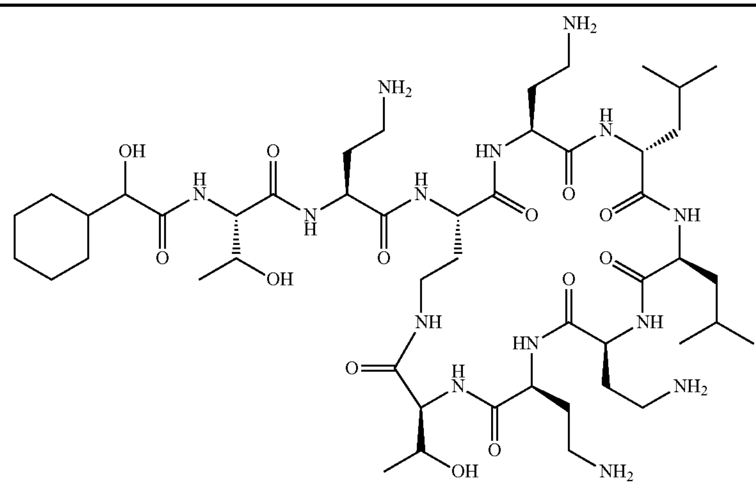 | 2 | Int. 4 | 2(RS)-(2-Hydroxy-2-cyclohexyl)ethanoyl polymyxin E nonapeptide, TFA salt. Isomer 2 | 5.67 | 1069.5 (MH+) |
| 33 | C50H85N15O12 | 1087.65 | 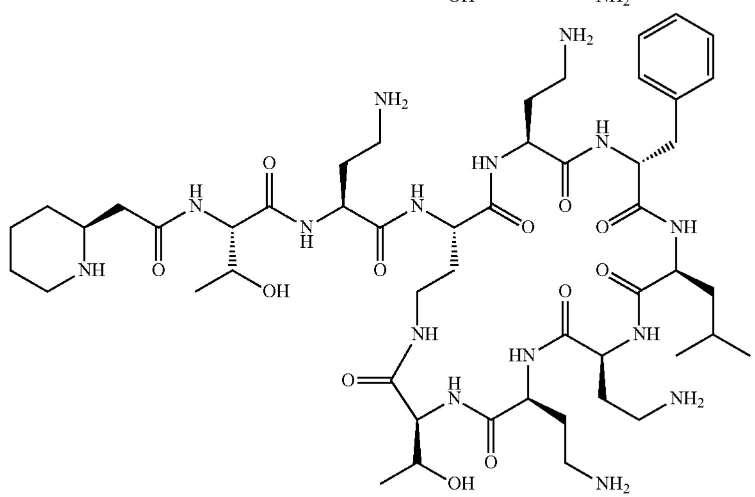 | 2 | Int. 2 | (2S)-piperidin-2-yl-ethanoyl polymyxin B nonapeptide, trifluoroacetate salt | 5.10 | 1088.5 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 34A | C49H83N15O12 | 1073.63 | 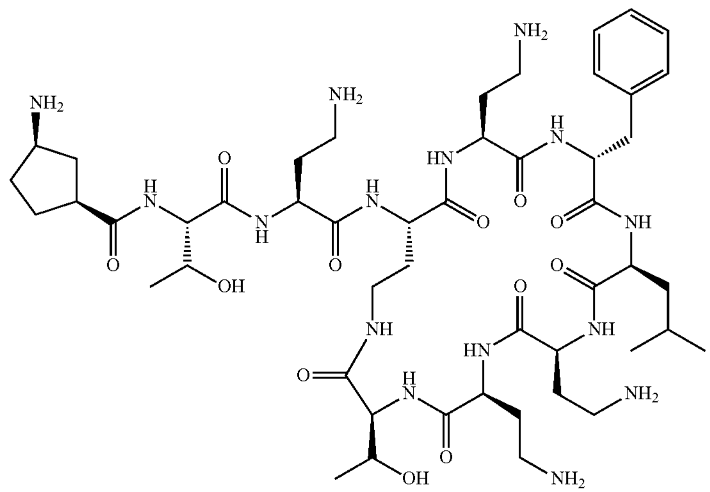 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)[C@H]2CC[C@@H](N)C2)C(C)O)CCNC(=O)[C@H](C(C)O)NC(=O)[C@H](CCN)NC(=O)[C@H](CCN)NC1=O] | 2 | Int. 2 | (1S,3R)-3-Aminocyclopentane carbonyl polymyxin B nonapeptide, trifluoroacetate salt | 5.25 | 1074.5, [MH]+ |
| 34B | C49H83N15O12 | 1073.63 | 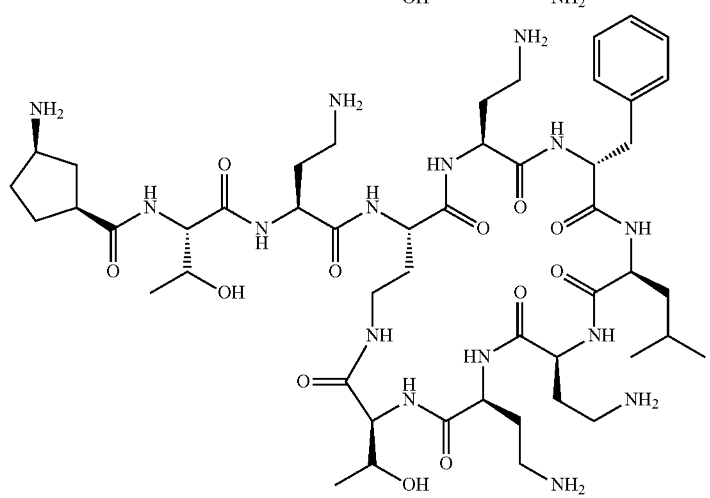 | 1 | Int. 2 | (1S,3R)-3-Aminocyclopentane carbonyl polymyxin B nonapeptide | 5.24 | 1074.6, [MH]+ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 35 | C48H81N15O13 | 1075.61 | 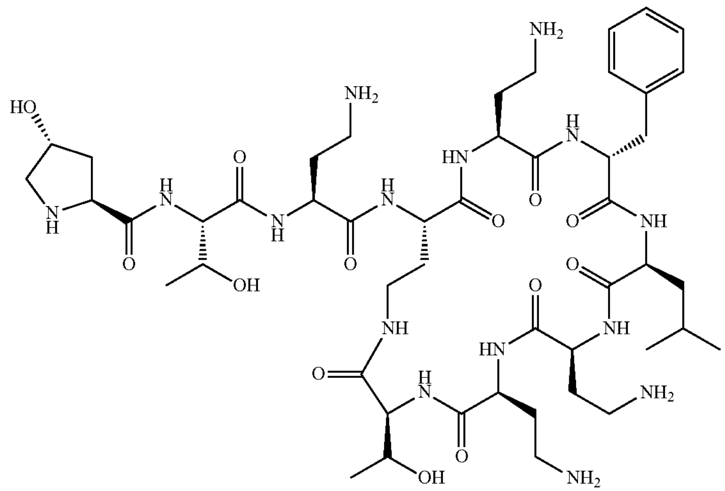 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)[C@@H]2C[C@@H](O)CN2)C(C)O)CCNC(=O)[C@H](C(C)O)NC(=O)[C@H](CCN)NC(=O)[C@H](CCN)NC1=O] | 2 | Int. 2 | (2S,4R)-4-Hydroxy-2-pyrrolidine carbonyl polymyxin B nonapeptide, trifluoroacetate salt | 5.22 | 1076, [MH]+ |
| 36 | C51H87N15O12 | 1101.67 | 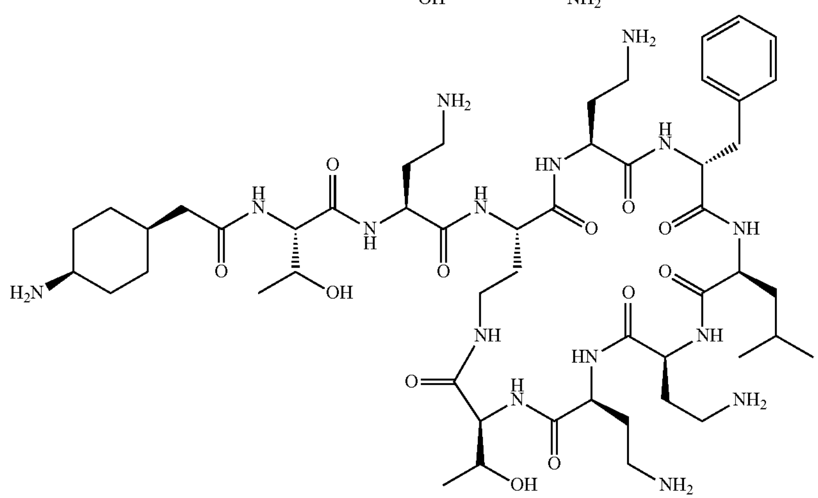 | 2 | Int. 2 | Cis-2-(4-aminocyclohexane) ethanoyl polymyxin B nonapeptide, trifluoroacetate salt | 4.98 | 1102 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 37 | C49H83N15O12 | 1073.63 | 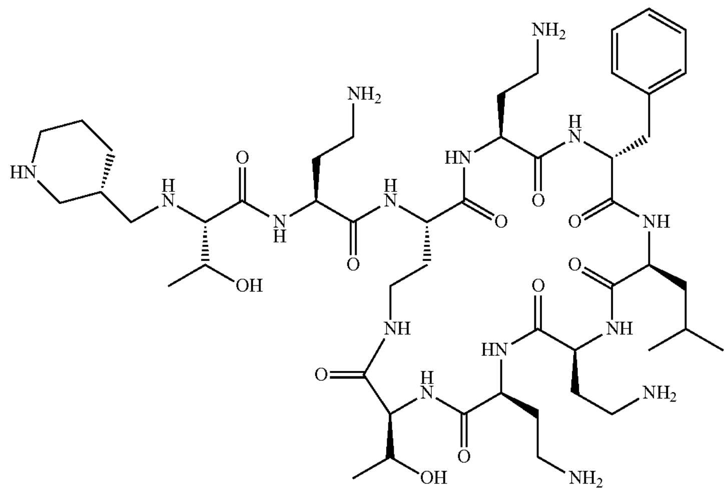 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC[C@H]2CCCNC2)C(C)O)CCNC(=O)[C@H](C(C)O)NC(=O)[C@H](CCN)NC(=O)[C@H](CCN)NC1=O] | 2 | Int. 2 | (S)-Piperidine-3-carbonyl polymyxin B nonapeptide, trifluoroacetate salt | 5.24 | 1074.5, [MH]+ |
| 38 | C56H85N15O12 | 1159.65 | 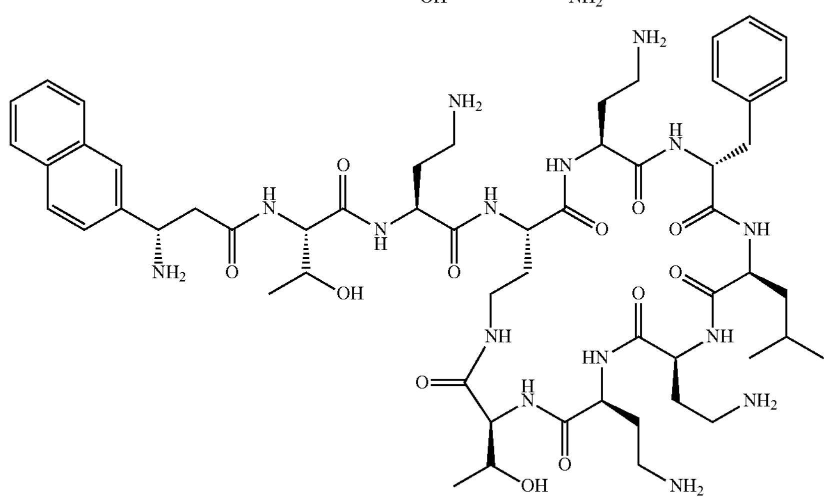 | 2 | Int. 2 | (S)-3-Amino-3-(naphthalene-2-yl)propanoyl polymyxin B nonapeptide, trifluoroacetate salt | 5.75 | 1160.5, [MH]+ |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| 39 | C56H97N17O13 | 1215.75 | 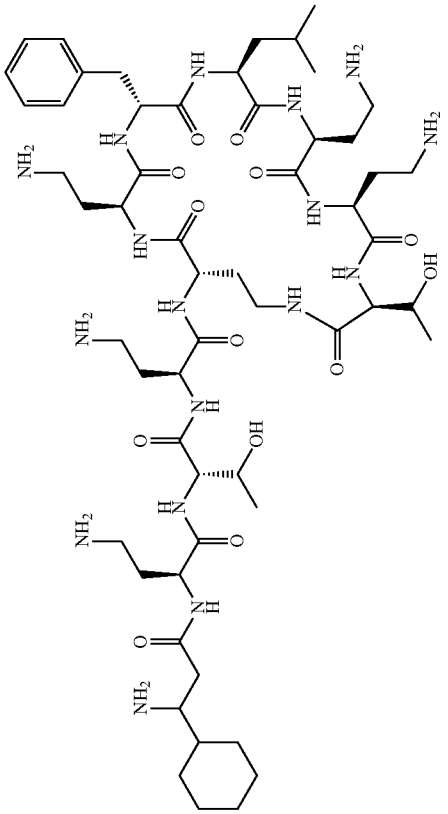 | 2 | Int. 6 | 3-(RS)-(3-Amino-3-cyclohexyl)propanoyl polymyxin B decapeptide, trifluoroacetate salt | 5.44 | 1216.4, [MH]+ |
| 40 | C51H87N15O12 | 1101.67 | 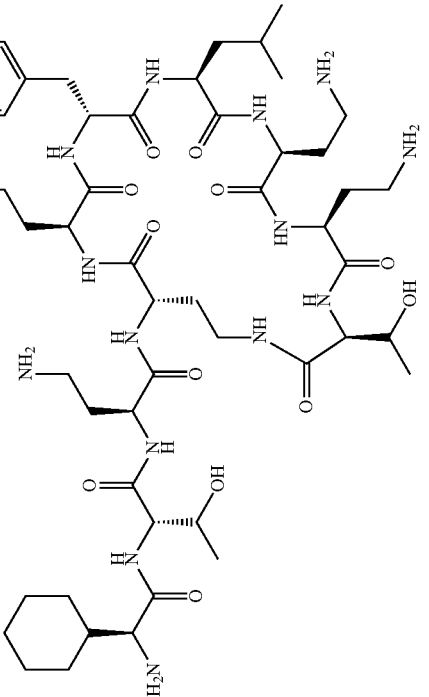 | 2 | Int. 2 | 2-(S)-(2-amino-2-cyclohexyl)ethanoyl polymyxin B nonapeptide, trifluoroacetate salt | 4.99 | 1102.6, [MH]+ |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 41 | C50H87N15O13 | 1105.66 | 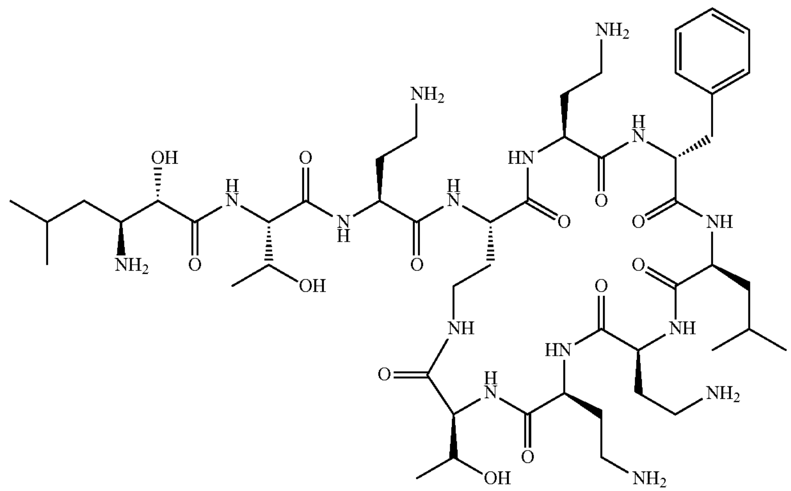 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)[C@@H](O)[C@@H](N)CC(C)C)C(C)O)CCNC(=O)[C@H](C(C)O)NC(=O)[C@H](CCN)NC(=O)[C@H](CCN)NC1=O] | 2 | Int. 2 | (2S,3S)-3-Amino-2-hydroxy-5-methylhexanoyl polymyxin B nonapeptide, trifluoroacetate salt | 5.19 | 1106.6, [MH]+ |
| 42 | C51H87N15O12 | 1101.67 | 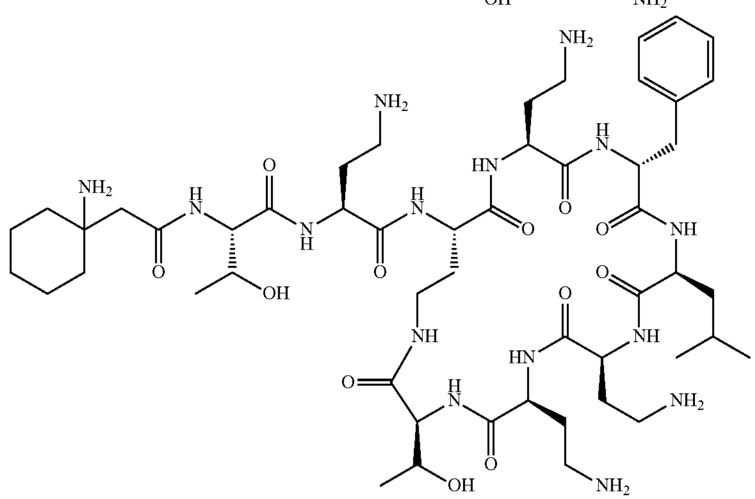 | 2 | Int. 2 | 2-(1-aminocyclohexyl) ethanoyl Polymyxin B nonapeptide TFA salt | 5.14 | 1102.5 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 43 | C48H81N15O12 | 1060.27 | 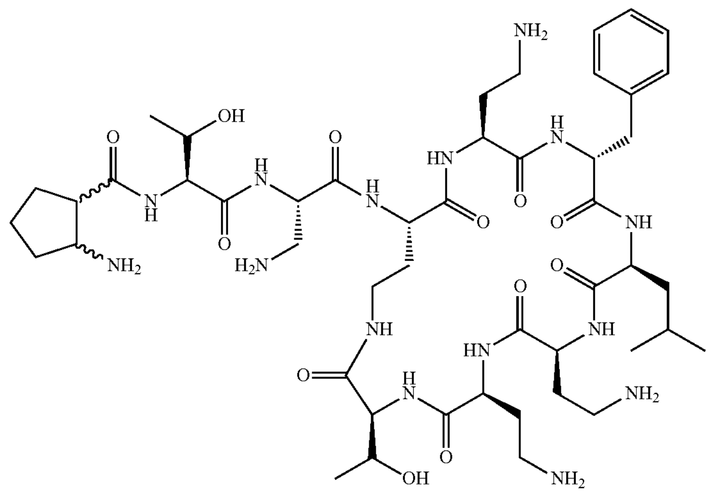 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)C2CCCC2N)C(C)O)CCNC(=O)[C@H](C(C)O)NC(=O)[C@H](CCN)NC(=O)[C@H](CCN)NC1=O] | 3 | Int. 5 | [2-Amino-cyclopentane-carbonyl]-L-Thr-L-Dap-polymyxin B heptapeptide, TFA salt | 4.96, 5.07 | 1061 531, ([M + 2H]$^{2+}$) |
| 44 | C48H80N14O13 | 1061.26 | 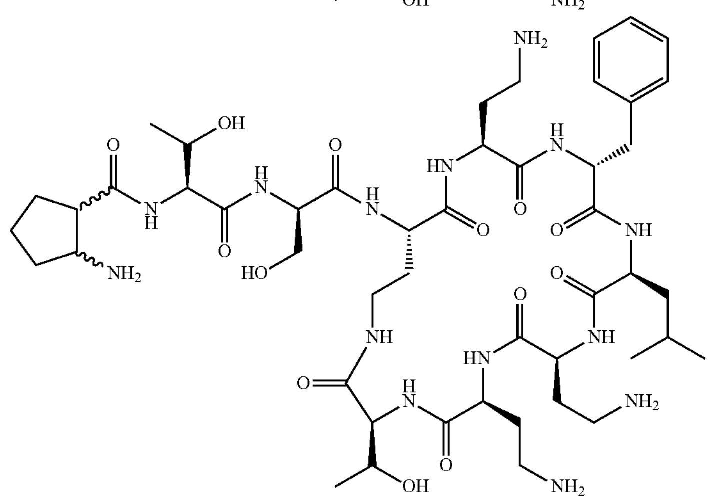 | 3 | Int. 5 | [2-Amino-cyclopentane-carbonyl]-L-Thr-D-Ser-polymyxin B heptapeptide, TFA salt | 5.05, 5.14 | 1062 531, ([M + 2H]$^{2+}$) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 45 | C50H84N14O13 | 1089.31 | 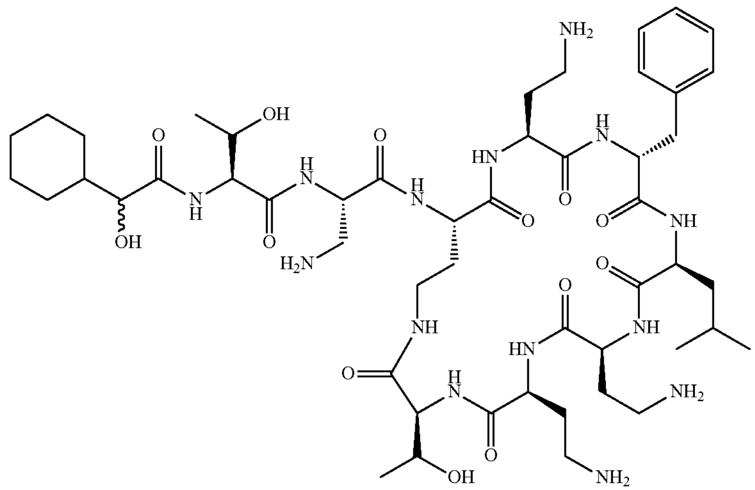 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)C(O)C2CCCCC2)C(C)O)CCNC(=O)[C@H](C(C)O)NC(=O)[C@H](CCN)NC(=O)[C@H](CCN)NC1=O] | 3 | Int. 5 | [2-cyclohexyl-2-hydroxyethanoyl]-L-Thr-L-Dap-polymyxin B heptapeptide, TFA salt | 5.91 | 1090 545, ([M + 2H]$^{2+}$) |
| 46 | C50H83N13O14 | 1090.3 | 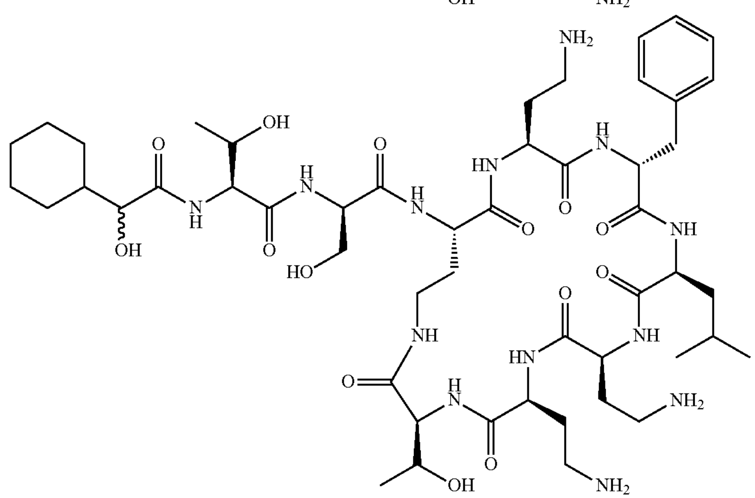 | 3 | Int. 5 | [2-cyclohexyl-2-hydroxyethanoyl]-L-Thr-D-Ser-polymyxin B heptapeptide, TFA salt | 5.81, 5.96 | 1091 546, ([M + 2H]$^{2+}$) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 47 | C51H87N15O12 | 1102.4 | 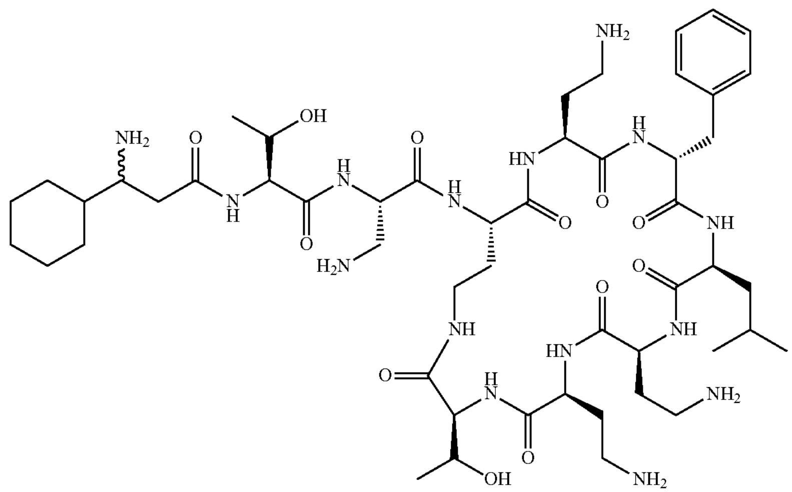 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)CC(N)C2CCCCC2)C(C)O)CCNC(=O)[C@H](C(C)O)NC(=O)[C@H](CCN)NC(=O)[C@H](CCN)NC1=O] | 3 | Int. 5 | [3-Amino-3-cyclohexyl-propionyl]-L-Thr-L-Dap-polymyxin B heptapeptide, TFA salt | 5.55 | 1103, 552, ([M + 2H]$^{2+}$) |
| 48 | C51H86N14O13 | 1103.3 | 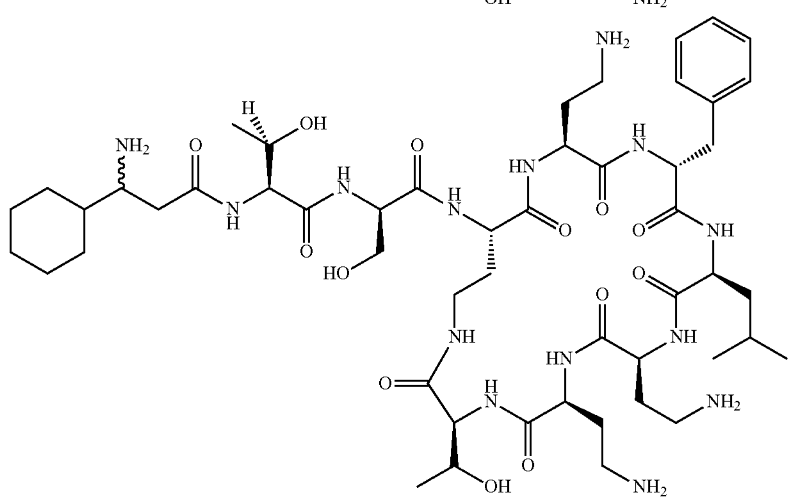 | 3 | Int. 5 | [3-Amino-3-cyclohexyl-propionyl]-L-Thr-D-Ser-polymyxin B heptapeptide, TFA salt | 5.68 | 1104, 552, ([M + 2H]$^{2+}$) |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| 51 | C51H87N15O12 | 1102.4 | 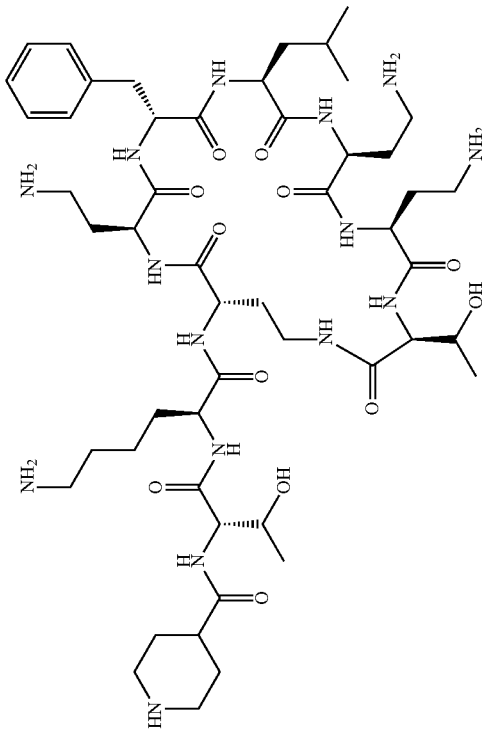 | 3A | Int. 5 | Piperidin-4-yl carbonyl-L-Thr-L-Lys-polymyxin B heptapeptide, TFA salt | 5.08 | 1103 (M + H)+ 552 (M + 2H)2+ |
| 52 | C49H84N16O12 | 1089.4 | 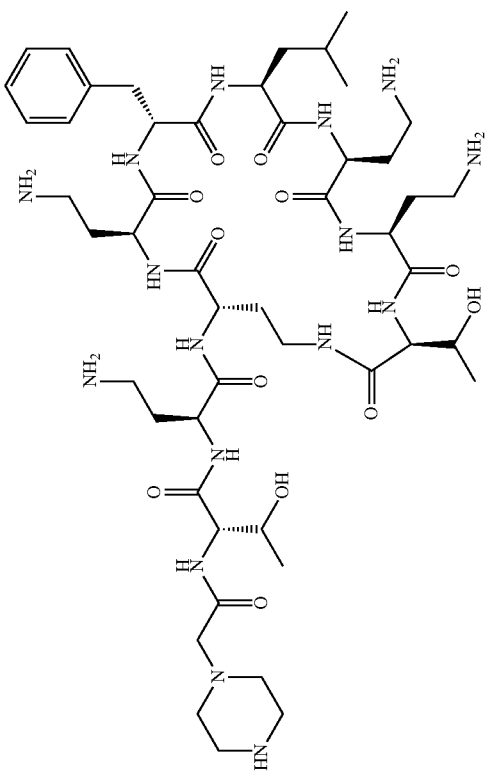 | 2 | Int 2 | (1-piperazine) ethanoyl polymyxin B nonapeptide, trifluoroacetate salt | 4.99 | 1090.6 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 53 | C53H91N17O13 | 1174.4 | 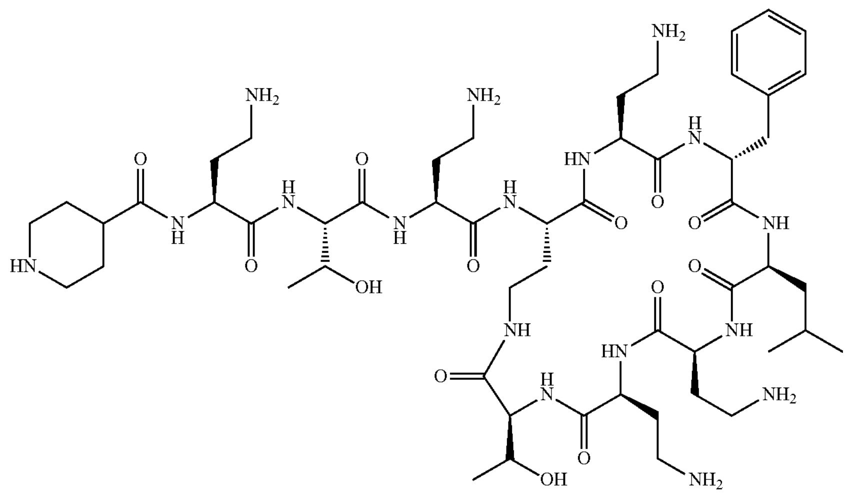 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)[C@H](CCN)NC(=O)C2CCNCC2)C(C)O)CCNC(=O)[C@H](C(C)O)NC(=O)[C@H](CCN)NC(=O)[C@H](CCN)NC1=O] | 3B | Int 2 | Piperidin-4-yl carbonyl-polymyxin B decapeptide, trifluoroacetate salt | 5.08 | 1175 (588) |
| 54 | C55H95N17O13 | 1202.5 | 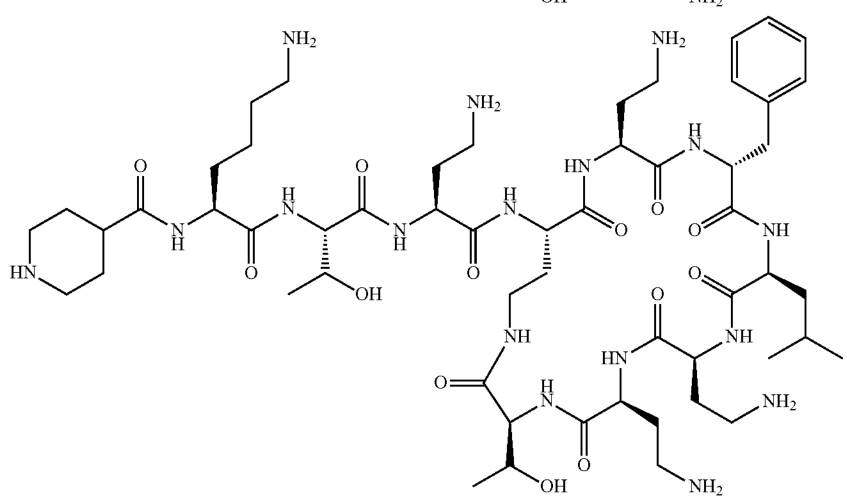 | 3B | Int 2 | Piperidin-4-yl carbonyl-L-Lys-polymyxin B nonapeptide, trifluoroacetate salt | 5.07 | 1203 (602) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| 55 | C55H88N16O12 | 1164.7 | 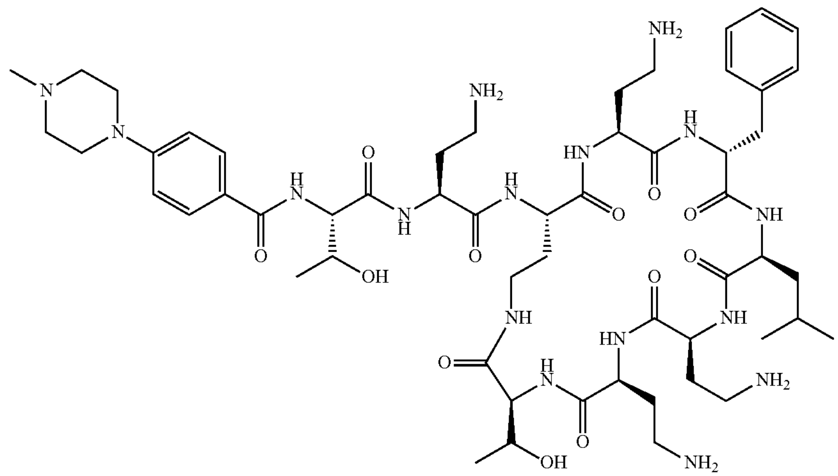 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)c2ccc(N3CCN(C)CC3)cc2)C(C)O)CCNC(=O)[C@H](C(C)O)NC(=O)[C@H](CCN)NC(=O)[C@H](CCN)NC1=O] | 1 | Int. 2 | 4-(4-Methyl-piperazin-1-yl)-benzoyl polymyxin B nonapeptide | 5.16 | |
| C1 | C50H85N13O13 | 1075.6 | 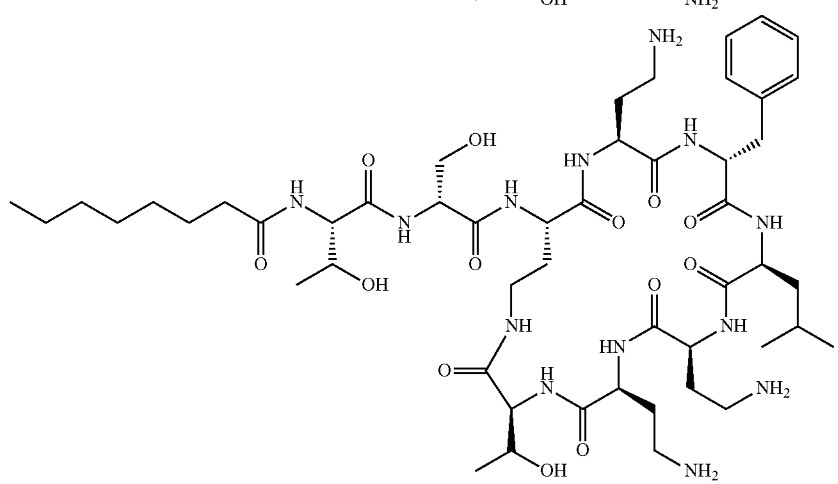 | 3 | Int. 5 | NAB-739 TFA salt | 6.40 | 1075.7 (M+) |

TABLE 4-continued
Example Compounds Isolated as Sulfate Salts
| Ex. | Formula | Mass | Structure | Method | Starting Material | Name | HPLC Retention time (min.) | m/z |
|---|---|---|---|---|---|---|---|---|
| C2 | C54H86ClN17O13 | 1215.6 | 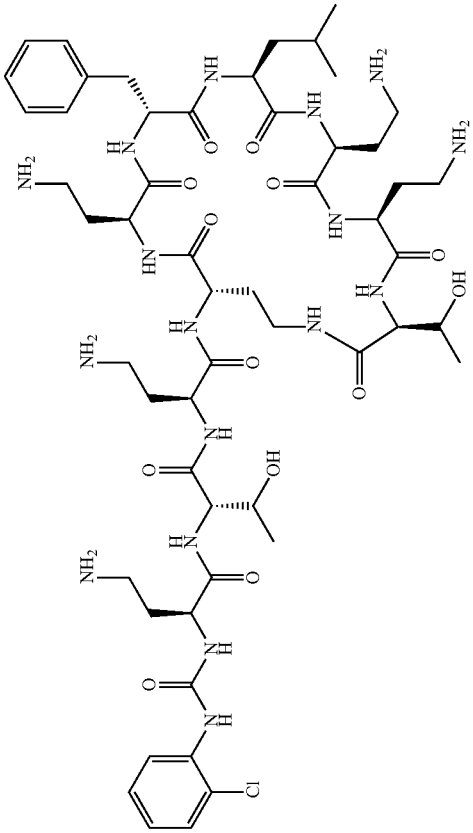 | — | Int 6 | CB-182, 804 sulphate salt | 5.66 | 1216.4 (MH+) |
| C3 | C50H78N14O12 | 1066.6 | 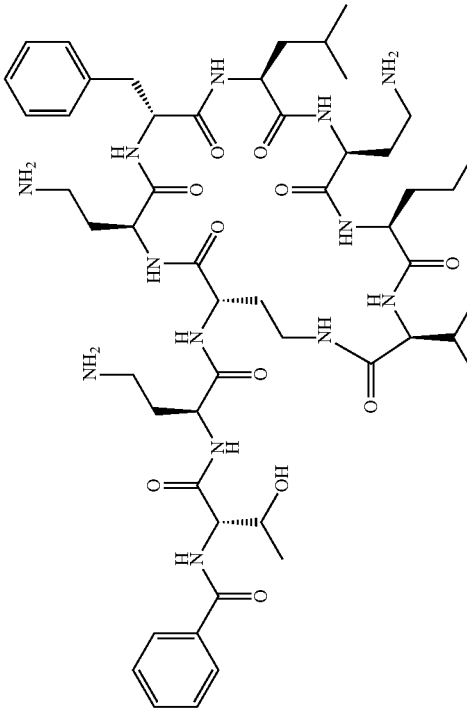 | 1 | Int. 2 | Benzoyl polymyxin B nonapeptide, sulphate salt | 5.68 | 1067.8 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| C4 | C51H86N14O12 | 1086.7 | 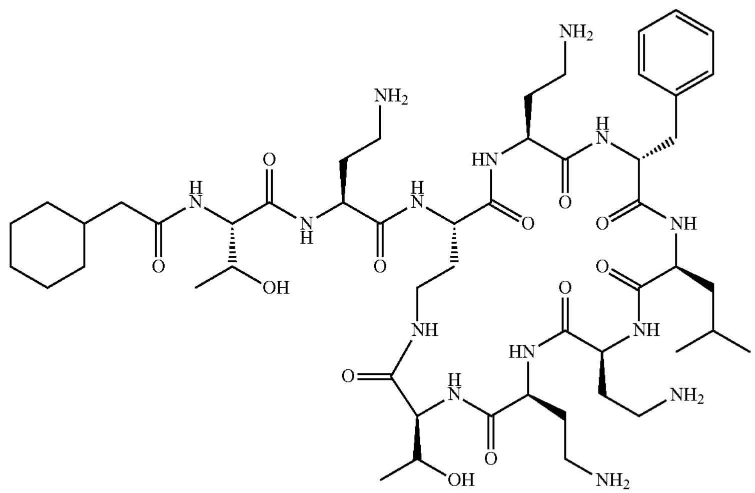 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)CC2CCCCC2)C(C)O)CCNC(=O)[C@H](C(C)O)NC(=O)[C@H](CCN)NC(=O)[C@H](CCN)NC1=O] | 2 | Int. 2 | Cyclohexyl ethanoyl polymyxin B nonapeptide, TFA salt | 6.28 | 1087.7 (MH+) |

TABLE 4-continued

Example Compounds Isolated as Sulfate Salts

| Ex. | Formula | Mass | Structure | Method | Starting Material | Name | HPLC Retention time (min.) | m/z |
|---|---|---|---|---|---|---|---|---|
| C5 | C50H79N15O12 | 1081.6 | 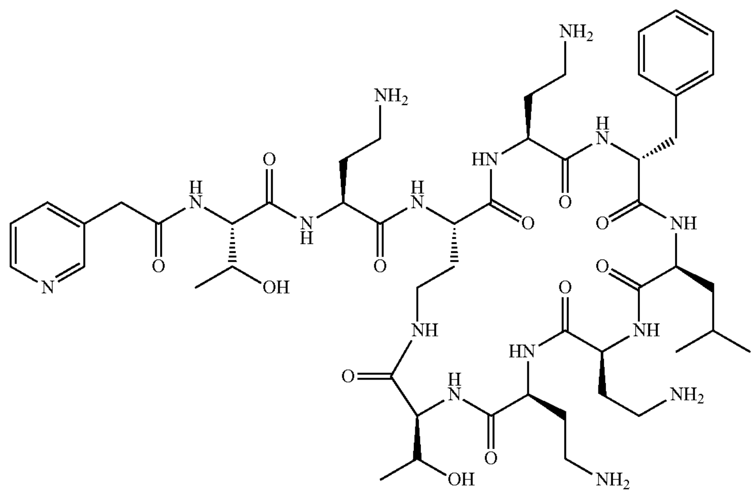 [SMILES: CC(C)C[C@@H]1NC(=O)[C@@H](Cc2ccccc2)NC(=O)[C@H](CCN)NC(=O)[C@@H](NC(=O)[C@H](CCN)NC(=O)[C@@H](NC(=O)Cc2cccnc2)C(C)O)CCNC(=O)[C@H](C(C)O)NC(=O)[C@H](CCN)NC(=O)[C@H](CCN)NC1=O] | 1 | Int. 2 | 3-pyridyl ethanoyl polymyxin B nonapeptide | 5.33 | 1082.5 (MH+) |

Example 49—N-[2-(1-aminocyclohexyl)ethyl] Polymyxin B nonapeptide

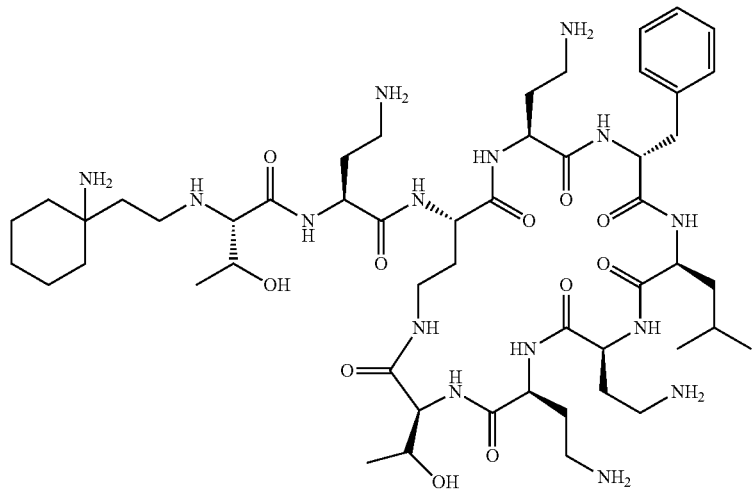

Chemical Formula: $C_{51}H_{89}N_{15}O_{11}$
Exact Mass: 1087.69
Molecular Weight: 1088.37

Step 1—To a solution of Intermediate 2 (100 mg, 0.073 mmol) in methanol (1.5 mL) and DCM (1.5 mL) was added N-Boc-1-aminocyclohexyl acetaldehyde (Squarix GmbH) (21 mg, 1.2 equiv.), and glacial acetic acid (0.15 mL). The mixture was stirred at room temperature for 30 minutes. (Polystyrylmethyl)trimethylammonium cyanoborohydride (4.0 mmol/g, 100 mg, Novabiochem) was added and the mixture stirred at room temperature overnight. The resin was removed by filtration and the filtrate evaporated to dryness. The residue was chromatographed on silica eluting with 0-20% (10% 880 ammonia in Methanol) in DCM. The least polar component from the column corresponded to the BOC-protected bis-alkylated product, which was obtained as a white solid (30 mg, 23%). m/z 1814 (MH+). The most polar component corresponded to the BOC-protected title compound, (85 mg, 74%). m/z 1589 (MH+).

Step 2—The most polar component from step 1 (31 mg, 0.019 mmol) was dissolved in DCM (2 mL) and treated with TFA (1 mL). The reaction mixture was stirred at room temperature for 1 hour. The solvent was evaporated and the residue azeotroped with toluene to afford a white solid. This was dissolved in water (5 mL), and the stirred with DCM (3 mL) for 5 min. The phases were separated and the aqueous phase was filtered through a 0.22 μm filter, then evaporated to low volume. The solution was lyophilised overnight to afford the title compound as a fluffy white solid as the TFA salt (20 mg, 62%). Retention time (HPLC), m/z 1088.6, MH+).

Example 50—3-Amino-3-cyclohexyl propanoyl-Thr-Dab-(cyclo)Dab*-Dab-DLeu-Thr-Dab-Dab-Thr*

[where * indicates cyclisation]

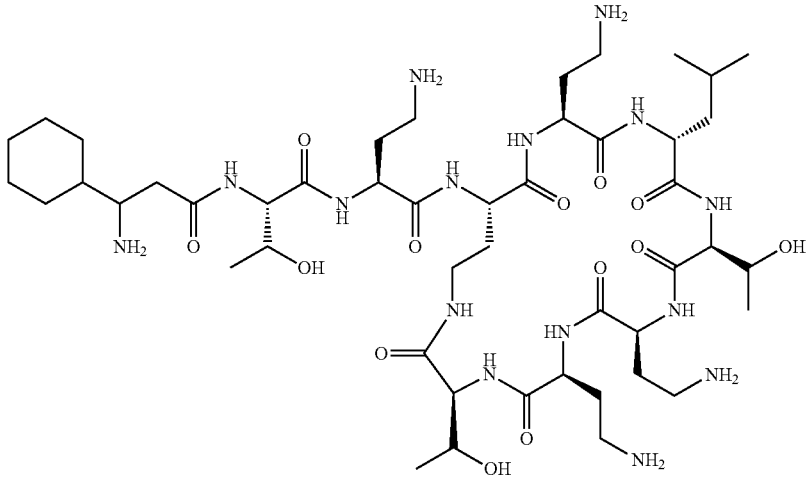

Chemical Formula: $C_{47}H_{87}N_{15}O_{13}$
Exact Mass: 1069.66
Molecular Weight: 1070.31

The title compound was prepared using conventional solid-phase chemistry using the standard FMOC protection strategy, starting with Fmoc-Thr(tBu)-PEG-PS resin, and using appropriately protected amino acids. The final peptide is partially deprotected at the cyclisation site and cleaved from the resin using TFA/TIS/H2O (96/2/2v/v) for 2 hrs. This material is cyclised using PyBop/HoBt/NMM in DCM. The benzyl groups which are still in place to prevent multi-site cyclisation are then removed using Pd/C in Acetic acid/MeOH/water (5/4/1v/v). The final target peptide is purified using C-18 Reverse phase column (10×250 mm), to afford the title compound as the trifluoroacetate salt, as a lyophilised solid. Retention time (HPLC) 4.52 min. m/z 1070.7 (MH+).

Comparator Compounds

The comparator compounds were Colistin (Polymyxin E), Polymyxin B (PMB), C1 (NAB-739), and C2 (CB-182,804).

CB-182,804 (C2) is a polymyxin decapeptide derivative with an aryl urea substituent at the N-terminus, which has been claimed to have lower toxicity than Polymyxin B (shown as compound 5 in WO 2010/075416), and was prepared by the present inventors. C1 was also prepared in-house, and corresponds to NAB-739 (as described by Vaara in, for example, WO 2008/01773.

Further compounds of the invention were prepared. All compounds were isolated as TFA salts unless otherwise stated. A1 and A3 were also prepared as sulfate salts according to the general method described herein. Comparator compound C6 was prepared using the general techniques described herein. The structures in the table depict the N-terminal group (—R) and side chain on the Polymyxin B heptapeptide scaffold (PMBH, below). Relative stereochemistry is depicted by heavy or dashed lines. Absolute stereochemistry is depicted by heavy or hashed wedged bonds.

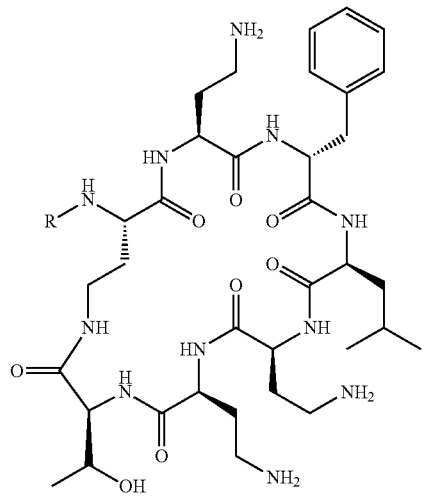

TABLE 4C

Further Example Compounds

| Ex. | —R | Formula | Mass | Method of Preparation | sm | Name | HPLC Retention time (min.) | m/z |
|---|---|---|---|---|---|---|---|---|
| A1 | | C52H83 N15O12 | 1109.6 | 2 | Int. 2 | 2-(3-(Aminomethyl)phenyl) ethanoyl polymyxin B nonapeptide | 5.22 | 1110.6 [MH+] |
| A2 | | C50H85 N15O12 | 1087.7 | 2 | Int. 2 | Piperidine-1-ylethanoyl polymyxin B nonapeptide | 5.33 | 1089 [MH+] |
| A3 | | C55H94 N16O14 | 1202.7 | 3B | Int. 7 | 2-(RS)-(2-Hydroxy-2-cyclohexyl)ethanoyl polymyxin B decapeptide | 5.48 | 1204 [MH+] 603 [M + 2H]$^{2+}$ |
| A4 | | C50H84 N14O13 | 1088.6 | 3A | Int. 5 | [2-(RS)-(2-Hydroxy-2-cyclohexyl)ethanoyl]-L-Thr-L-Dap-polymyxin B heptapeptide | 5.79 | 1090 [MH+] 545 [M + 2H]$^{2+}$ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A5 | 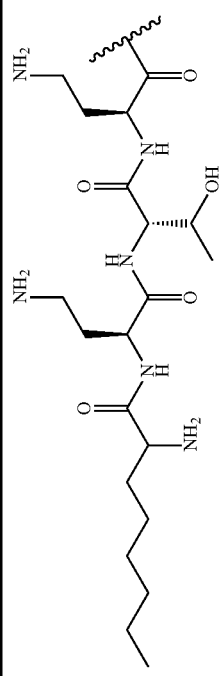 | C55H97 N17O13 | 1203.7 | 3B | Int. 7 | 2-(RS)-2-aminooctyl polymyxin B decapeptide | 5.29 | 1204 [MH+] 603 [M + 2H]²⁺ |
| A6 | 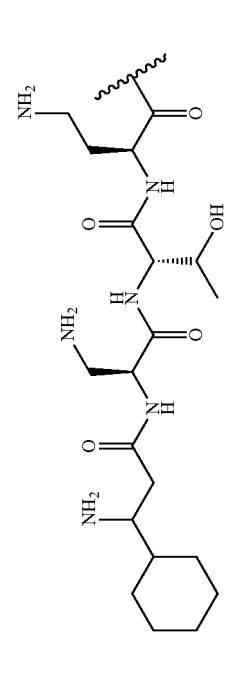 | C55H95 N17O13 | 1201.7 | 3B | Int. 7 | [3(R,S)-3-Amino-3-cyclohexanepropanoyl]-L-Dap- polymyxin B nonapeptide | 5.31 | 602 [M + 2H]²⁺ 402 [M + 3H]³⁺ |
| A7 | 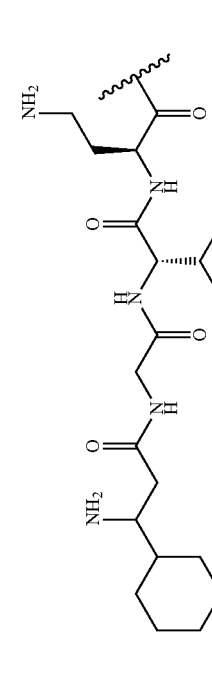 | C54H92 N16O13 | 1172.7 | 3B | Int. 7 | [3(R,S)-3-Amino-3-cyclohexanepropanoyl]-Gly-polymyxin B nonapeptide | 5.38 | 1173 [MH+] 587 [M + 2H]²⁺ |
| A8 | 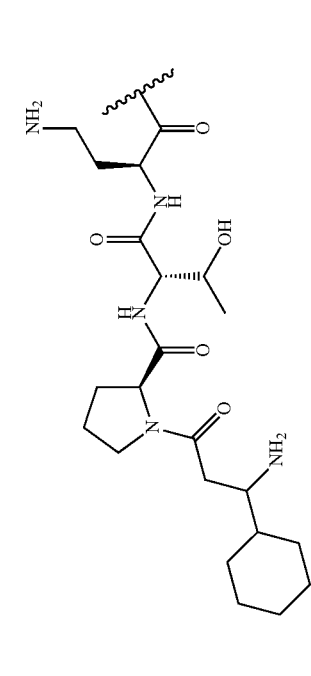 | C57H96 N16O13 | 1212.7 | 3B | Int. 7 | [3(R,S)-3-Amino-3-cyclohexanepropanoyl]-L-Pro- polymyxin B nonapeptide isomer 1 | 5.42 | 1213 [MH+] 607 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A9 | | C57H96N16O13 | 1212.7 | 3B | Int. 7 | [3(R,S)-3-Amino-3-cyclohexanepropanoyl]-L-Pro- polymyxin B nonapeptide isomer 2 | 5.54 | 1213 [MH+] 607 [M + 2H]²⁺ |
| A10 | | C55H95N17O13 | 1201.7 | 3A | Int. 5 | [3(R,S)-3-Amino-3-cyclohexanepropanoyl]-L-Dab-L-Thr-L-Dap polymyxin B heptapeptide | 5.29 | 1202 [MH+] |
| A11 | | C55H94N16O14 | 1202.7 | 3B | Int. 7 | [3(R,S)-3-Amino-3-cyclohexanepropanoyl]-L-Ser- polymyxin B nonapeptide | 5.37 | 1204 [MH+] 603 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A12 | | C57H96 N16O14 | 1228.7 | 3B | Int. 7 | [3(R,S)-3-Amino-3-cyclohexanepropanoyl]-[4R-4-hydroxy-L-Pro]-polymyxin B nonapeptide | 5.35 | 1230 [MH+] 616 [M + 2H]²⁺ |
| A13 | | C52H89 N17O13 | 1159.7 | 3A | Int. 5 | [(3S)-piperidine-3-carbonyl]-L-Dab-L-Thr-L-Dap polymyxin B heptapeptide | 5.04 | 1160 [MH+] 581 [M + 2H]²⁺ |
| A14 | | C54H85 N15O12 | 1135.7 | 2A | Int. 7 | (S)-2-((1,2,3,4)-tetrahydroisoquinolin-3-yl)ethanoyl polymyxin B nonapeptide | 5.42 | 1137 [MH+] 569 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A15 | 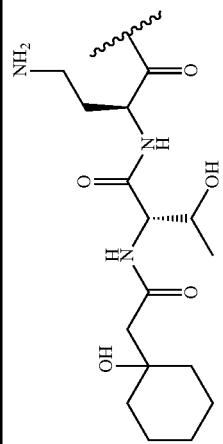 | C51H86 N14O13 | 1102.6 | 2A | Int. 7 | 2-(1-Hydroxycyclohexyl)ethanoyl polymyxin B nonapeptide | 5.53 | 1216[M + TFA]+ 1104 [MH+] 553 [M + 2H]$^{2+}$ |
| A16 | 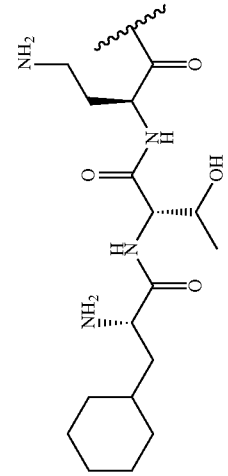 | C52H89 N15O12 | 1115.7 | 2A | Int. 7 | (2S)-2-Amino-3-cyclohexanepropanoyl polymyxin B nonapeptide | 5.36 | 1117 [MH+] 559 [M + 2H]$^{2+}$ |
| A17 | 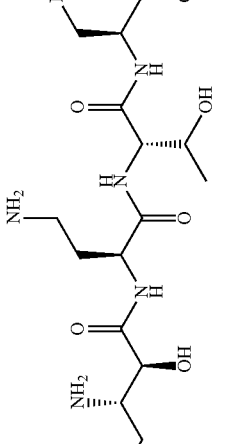 | C53H93 N17O14 | 1191.7 | 2A | Int. 5 | [(2S,3S)-3-Amino-2-hydroxy-5-methylhexanoyl]-L-Dab-L-Thr-L-Dap polymyxin B heptapeptide | 5.20 | 1192 [MH+] 597 [M + 2H]$^{2+}$ |
| A18 | 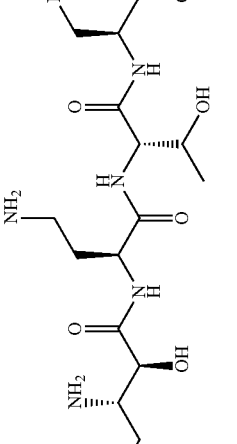 | C54H95 N17O14 | 1205.7 | 2A | Int. 8 | (2S,3S)-3-Amino-2-hydroxy-5-methylhexanoyl polymyxin B decapeptide | 5.10 | 1207 [MH+] 604 [M + 2H]$^{2+}$ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A19 | | C58H96 N18O13 | 1252.7 | 3B | Int. 7 | [3(R,S)-3-Amino-3-cyclohexanepropanoyl]-L-His- polymyxin B nonapeptide | 5.30 | 1253 [MH+] 628 [M + 2H]²⁺ |
| A20 | | C61H98 N16O13 | 1262.7 | 3B | Int. 7 | [3(R,S)-3-Amino-3-cyclohexanepropanoyl]-L-Phe- polymyxin B nonapeptide isomer 1 | 5.86 | 1264 [MH+] 632 [M + 2H]²⁺ |
| A21 | | C61H98 N16O13 | 1262.7 | 3B | Int. 7 | [3(R,S)-3-Amino-3-cyclohexanepropanoyl]-L-Phe- polymyxin B nonapeptide isomer 2 | 5.95 | 1264 [MH+] 632 [M + 2H]²⁺ |
| A22 | | C53H91 N17O13 | 1173.7 | 2A | Int. 8 | (S)-Piperidine-3-carbonyl polymyxin B decapeptide. | 5.02 | 1175 [MH+] 588 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A23 | | C58H101N19O13 | 1271.8 | 3B | Int. 7 | [3(R,S)-3-Amino-3-cyclohexanepropanoyl]-L-Arg- polymyxin B nonapeptide | 5.40 | 1273 [MH+] 637 [M + 2H]²⁺ |
| A24 | | C49H83N15O12 | 1073.6 | 2A | Int. 7 | (R)-Piperidine-3-carbonyl polymyxin B nonapeptide | 5.01 | 1074 [MH+] 538 [M + 2H]²⁺ |
| A25 | | C49H83N15O12 | 1073.6 | 2A | Int. 7 | Piperidine-2-carbonyl polymyxin B nonapeptide. Isomer 1 | 5.04 | 1075 [MH+] 538 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A26 | | C49H83 N15O12 | 1073.6 | 2A | Int. 7 | Piperidine-2-carbonyl polymyxin B nonapeptide. Isomer 2 | 5.10 | 1074 [MH+] 538 [M + 2H]$^{2+}$ |
| A27 | | C61H98 N16O14 | 1278.7 | 3B | Int. 7 | [3(R,S)-3-Amino-3-cyclohexanepropanoyl]-L-Tyr- polymyxin B nonapeptide | 5.54 | 1280 [MH+] 641 [M + 2H]$^{2+}$ |
| A28 | | C58H99 N17O13 | 1241.8 | 3B | Int. 7 | 4-[3(R,S)-3-Amino-3-cyclohexanepropanamido] piperidine-4-carbonyl polymyxin B nonapeptide | 5.31 | 1242.6 [MH+] |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A29 | 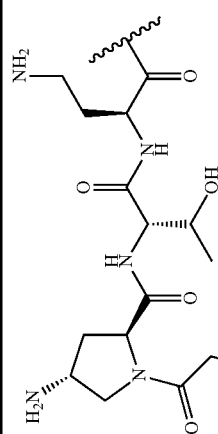 | C57H97 N17O13 | 1227.7 | 3B | Int. 7 | (2S,4R)-4-amino-1-(3-amino-3-cyclohexylpropanoyl)pyrrolidine-2-carbonyl polymyxin B nonapeptide | 5.21 | 1229 [MH+] 615 [M + 2H]²⁺ |
| A30 | 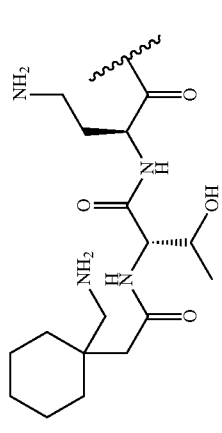 | C52H89 N15O12 | 1115.7 | 2A | Int. 7 | 2-(1-(Aminomethyl)cyclohexyl) ethanoyl Polymyxin B nonapeptide | 5.26 | 1116 [MH+] 558 [M + 2H]²⁺ |
| A31 | 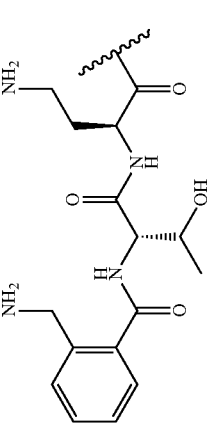 | C51H81 N15O12 | 1095.6 | 2A | Int. 7 | 2-Aminomethylbenzoyl polymyxin B nonapeptide | 5.08 | 1096 [MH+] 549 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A32 | | C51H89N15O12 | 1103.7 | 2A | Int. 7 | 3-(RS)-3-amino octanoyl polymyxin B nonapeptide. Isomer 1 | 5.34 | 1105 [MH+] 553 [M + 2H]²⁺ |
| A33 | | C51H89N15O12 | 1103.7 | 2A | Int. 7 | 3-(RS)-3-amino octanoyl polymyxin B nonapeptide. Isomer 2 | 5.43 | 1105 [MH+] 553 [M + 2H]²⁺ |
| A34 | | C51H87N15O12 | 1101.7 | 2A | Int. 7 | (1-aminomethylcyclohexane) carbonyl polymyxin B nonapeptide | 5.57 | 1102 [MH+] |
| A35 | | C52H83N15O12 | 1109.6 | 2A | Int. 7 | D-Phe polymyxin B nonapeptide | 5.43 | 1110 [MH+] 555 [M + 2H]²⁺ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A36 | | C48H81N15O12 | 1059.6 | 2A | Int. 7 | D-Pro polymyxin B nonapeptide | 5.01 | 1060 [MH+] |
| A37 | | C48H81N15O12 | 1059.6 | 2A | Int. 7 | L-Pro polymyxin B nonapeptide | 5.05 | 1060 [MH+] |
| A38 | | C51H87N15O12 | 1101.7 | 2A | Int. 7 | 2-(R)-(2-amino-2-cyclohexyl)ethanoyl polymyxin B nonapeptide | 5.24 | 1103 [MH+] |
| A39 | | C50H85N15O12 | 1087.7 | 2A | Int. 7 | 3-Methylpiperidine-3-carbonyl polymyxin B nonapeptide | 5.06 | 1089 [MH+] |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A40 | | C48H81 N15O13 | 1075.6 | 2A | Int. 7 | (2S)-Morpholine-2-carbonyl polymyxin B nonapeptide | 4.88 | 1076 [MH+] 539 [M + 2H]$^{2+}$ |
| A42 | | C49H85 N15O12 | 1075.7 | 2A | Int. 7 | D-Leu-polymyxin B nonapeptide | 5.13 | 1076 [MH+] 539 [M + 2H]$^{2+}$ |
| A43 | | C57H99 N15O12 | 1185.8 | 2A | Int. 7 | Cis-4-Octyl piperidine-2-carbonyl polymyxin B nonapeptide. Isomer 1 | 6.66 | 1187 [MH+] 594 [M + 2H]$^{2+}$ |
| A44 | | C57H99 N15O12 | 1185.8 | 2A | Int. 7 | Cis-4-Octyl piperidine-2-carbonyl polymyxin B nonapeptide. Isomer 2 | 7.07 | 1187 [MH+] 594 [M + 2H]$^{2+}$ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A45 | | C50H87 N15O12 | 1089.7 | 2A | Int. 7 | 3-(R)-3-Amino-5-methylhexanoyl polymyxin B nonapeptide | 5.22 | 1091 [MH+] |
| A46 | | C52H90 N16O12 | 1130.7 | 2A | Int. 7 | (R)-4-isobutylpiperazine-2-carbonyl polymyxin B nonapeptide | 5.25 | 1132 [MH+] 567 [M + 2H]$^{2+}$ |
| A47 | | C53H90 N16O13 | 1158.7 | 2A | Int. 7 | (S)-1-(3-methylbutanoyl) piperazine-2-carbonyl polymyxin B nonapeptide. | 5.30 | 1159 [MH+] 580 [M + 2H]$^{2+}$ |
| A48 | | C53H91 N15O12 | 1129.69 7048 | 2A | Int. 7 | (S)-1-(2-methylpropyl)-piperidine-3-carbonyl polymyxin B nonapeptide | 5.27 | 1130 [MH+] 566 [M + 2H]$^{2+}$ |

TABLE 4C-continued

Further Example Compounds

| Ex. | —R | Formula | Mass | Method of Preparation | sm | Name | HPLC Retention time (min.) | m/z |
|---|---|---|---|---|---|---|---|---|
| A49 | | C48H82N16O12 | 1074.629692 | 2A | Int. 7 | (2S)-piperazine-2-carbonyl polymyxin B nonapeptide | 4.99 | 1075 [MH+] 538 [M + 2H]$^{2+}$ |
| A50 | | C49H83N15O13 | 1089.6 | 2A | Int. 7 | 5-Hydroxypiperidine-3-carbonyl polymyxin B nonapeptide | 5.10 | 1090.6 [MH+] |
| C6 | | C51H88N14O12 | 1088.7 | 1 | Int. 2 | Octanoyl polymyxin B nonapeptide, sulfate salt | 6.29 | 1089.6 [MH+] |

BiOLOGICAL ACTIVITY

To evaluate the potency and spectrum of the compounds both alone and in combination with another agent, susceptibility testing was performed against up to four strains of each of the four Gram negative pathogens, *Escherichia coli, Pseudomonas aeruginosa, Klebsiella pneumoniae* and *Acinetobacter baumannii*.

Ratios of components in a combination, such as 1:1, refers to a weight to weight ratio. The minimum inhibitory concentration (MIC) refers to the total drug concentration (e.g. test compound plus second agent, such as Rifampicin).

Combination Activity

The inoculum was prepared by making a direct suspension of isolated colonies (selected from an 18-24 hour Mueller-Hinton agar plate) adjusted to the 0.5 McFarland standard.

MIC testing was performed by two-fold serial antibiotic dilutions in cation-adjusted Mueller-Hinton Broth in sterile 96-well microtitre plates in a total volume of 170 μL (150 μL broth containing the antimicrobial agent, 20 μL inoculum). The assays were performed in duplicate. Plates were incubated aerobically without shaking for 18-20 hours at 35° C. with the MIC defined as the lowest concentration of drug that prevented visible growth.

In cases where the duplicate values varied by less than 2-fold, the lower of the two values is reported. If a variation of greater than 2-fold was observed, the assay was considered non-valid. Several of the compounds were subjected to multiple tests, and where this is the case, the MIC reflects the modal value obtained.

Table 5 shows the MIC values (micrograms/mL) recorded for compounds of Examples 1 to 55 in a 1:1 (wt:wt) combination with Rifampicin. Comparator compounds, all tested as a 1:1 mixture with Rifampicin are: Colistin (Polymyxin E), Polymyxin B (PMB), Polymyxin B nonapeptide (PMBN), C2 (CB-182,804), and C1 (NAB-739).

CB-182,804 is a polymyxin decapeptide derivative with an aryl urea substituent at the N-terminus, which has been claimed to have lower toxicity than Polymyxin B (shown as compound 5 in WO 2010/075416), and was prepared by the present inventors. C1 was also prepared in-house, and corresponds to NAB-739 (as described by Vaara in, for example, WO 2008/017734.

Table 5A sets out the MIC values (micrograms/mL) for certain Example Compounds in comparison with reference examples compounds C3 to C5, in a 1:1 (wt:wt) combination with Rifampicin. The results show that compounds containing hydroxyl and/or amino groups (such as —NR$^6$R$^7$) provide greater potentiating effects over those compounds that do not contain hydroxyl and/or amino groups.

Comparison of Reference Example C3 (benzoyl side chain) with the corresponding aniline counterpart (Example Compound 5) demonstrates an improvement in MIC against strains of *Klebsiella* and *Pseudomonas* for the aniline compound over C3 when both are combined with Rifampicin. Likewise, introduction of the piperidine onto the benzoyl group (Example 55) similarly improves the activity against these organisms.

Replacement of the cyclohexyl ring in Example C4 by a piperidine, as in Example 33, also shows a significant improvement in activity against strains of all the organisms tested. Other piperidine analogues also show good levels of activity (Example Compounds 29 and 37). The basicity at this position is important, however, as an analogous pyridyl derivative (Reference Example C5) does not show the enhanced level of activity in combination with Rifampicin.

Table 5B shows the effect of altering the ratio of the compound to rifampicin in the combination.

The minimum inhibitory concentration refers to the total drug concentration (e.g. test compound plus Rifampicin). The compounds are used at equal mass within the combination. The weight refers to the mass of compound as used, for example the Example Compounds are used in their TFA or sulphate salt forms.

The stoichiometry of the example compounds in salt form was believed to be approximately 1:5 compound:acid for TFA and 1:2.5 for sulphate, for example where five amino groups are present in the example compound.

The second agents used were as follows: Vancomycin Hydrochloride, Meropenem Trihydrate, Tigecycline hydrate, Ciprofloxacin free acid, Fusidic acid sodium salt, Azithromycin dihydrate, Aztreonam free acid, Oxacillin, sodium salt and Novobiocin sodium salt.

TABLE 5

MIC Values (micrograms/mL) for Example Compounds in 1:1 combination with Rifampicin

| Example | E. coli ATCC25922 | E. coli NCTC9001 | K. pneumoniae ATCC-BAA-2146 | K. pneumoniae CCUG-59348 | K. pneumoniae NCTC 13438 | K. pneumoniae ATCC 4352 | P. aeruginosa ATCC-47 | P. aeruginosa CCUG 59626 | P. aeruginosa ATCC 27853 | P. aeruginosa ATCC CRM-9027 | A. baumannii NCTC 13424 | A. baumannii CCUG57249 | A. baumannii ATCC BAA-747 | A. baumannii NCTC 13423 |
|---|---|---|---|---|---|---|---|---|---|---|---|---|---|---|
| Rifampicin | 4 | 4 | 16 | 32 | 16 | 8 | 16 | 16 | 16 | 16 | 1 | 2 | 2 | 1 |
| Colistin | 0.25 | 0.25 | 1 | 1 | 0.5 | 0.5 | 2 | 0.5 | 0.25 | 1 | 0.25 | 0.25 | 0.25 | 0.125 |
| PMB | 0.5 | 0.5 | 1 | 1 | 1 | ND | 0.5 | 0.5 | 0.5 | 0.125 | 0.5 | 1 | 0.25 | 0.125 |
| PMBN | 0.5 | 1 | 1 | 4 | ND | 0.25 | 0.25 | 0.125 | 0.125 | 2 | 0.5 | 0.5 | 0.5 | 0.5 |
| C1 | 0.5 | 0.25 | 2 | 4 | ND | 0.5 | 4 | 2 | 2 | 2 | 0.5 | 0.5 | 0.5 | 0.5 |
| C2 | 0.125 | 0.25 | 0.5 | 2 | ND | 0.25 | 0.25 | 0.125 | 0.5 | 0.5 | ND | 0.25 | 0.25 | 0.25 |
| 1 | ND | 0.5 | 2 | 2 | 1 | 1 | 1 | 1 | 0.5 | ND | 0.25 | ND | ND | ND |
| 2 | 0.125 | 0.25 | 0.5 | 2 | 0.5 | ND | 0.25 | 0.125 | ND | 0.25 | ≤0.06 | ≤0.06 | ≤0.06 | ≤0.06 |
| 3 | ND | ND | 0.5 | 4 | ND | ND | ND | ND | ND | ND | ND | ND | ND | ND |
| 4 | ND | ND | 1 | 8 | 2 | ND | ND | ND | ND | ND | ND | ND | ND | ND |
| 5 | ND | 0.25 | 2 | 16 | 0.5 | ND | ND | ND | ND | ND | ND | ND | ND | ND |
| 6 | ≤0.06 | ND | 1 | 2 | ND | ≤0.06 | 0.25 | ≤0.06 | ND | ND | ≤0.06 | ≤0.06 | ≤0.06 | ≤0.06 |
| 7 | ND | 0.25 | ND | 4 | ND | ND | ND | 0.125 | ND | ND | ND | ND | ND | ND |
| 8 | 0.125 | ND | 0.25 | 4 | 0.5 | ND | 0.25 | 0.125 | ND | 0.25 | 0.125 | ≤0.06 | ≤0.06 | ≤0.06 |
| 9 | ND | ND | 2 | 8 | ND | ND | ND | 0.25 | ND | ND | 0.5 | ND | ND | ND |
| 10 | 0.125 | 0.125 | 0.5 | 1 | 0.5 | ≤0.06 | 0.25 | 0.125 | 1 | ND | 0.125 | 0.125 | 0.25 | 0.125 |
| 11 | ND | 1 | 0.5 | 4 | 1 | ND | ND | 0.25 | ND | ND | 0.125 | ≤0.06 | ND | ND |
| 12 | 0.125 | ND | 4 | 16 | 4 | ND | 0.125 | 0.5 | ND | ND | ND | ≤0.06 | ND | ND |
| 13 | 0.125 | 0.5 | 0.5 | 4 | 1 | 0.125 | ND | ND | ND | ND | ≤0.06 | 0.125 | ≤0.06 | ≤0.06 |
| 14 | ND | ND | 2 | 16 | 0.5 | ND | ND | ND | ND | ND | ND | ND | ND | ND |
| 15 | ND | ND | 4 | 16 | ND | ND | ND | 0.5 | ND | ND | 0.125 | ND | 0.125 | ND |
| 16 | ≤0.06 | 0.125 | 0.5 | ND | 0.5 | ND | ND | 0.125 | ND | ND | ≤0.06 | ≤0.06 | ≤0.06 | ≤0.06 |
| 17 | ≤0.06 | ND | 0.125 | 2 | 0.5 | 0.125 | 0.25 | 0.125 | 0.25 | 0.125 | <0.06 | <0.06 | 0.125 | ≤0.06 |
| 18 | 0.125 | 0.125 | 0.5 | 4 | 0.25 | ND | ND | 0.125 | 0.25 | 0.125 | 0.125 | ≤0.06 | ND | 0.125 |
| 19 | ND | 1 | 0.5 | 2 | 0.5 | ND | 0.5 | 0.25 | 1 | 1 | 0.125 | 0.125 | ND | ND |
| 20 | ND | ND | 2 | 4 | 0.25 | ND | ND | 0.125 | ND | ND | <0.06 | ≤0.06 | ND | ND |
| 21 | 0.125 | 0.125 | 0.25 | 8 | 0.5 | ND | 0.125 | 0.125 | ND | ND | ≤0.06 | ND | ND | ND |
| 22 | ND | ND | 0.25 | 4 | 0.5 | ND | ND | ND | ND | ND | ND | ND | ND | ND |
| 23 | ND | 0.25 | 1 | 8 | 0.5 | ND | ND | 0.5 | ND | ND | 0.5 | ND | ND | ND |
| 24 | ND | ND | 0.5 | 8 | 1 | ND | ND | 0.25 | ND | ND | 0.5 | ND | ND | ND |
| 25 | ≤0.06 | ND | 1 | 8 | 2 | ND | ND | 0.25 | ND | ND | 0.5 | ND | ND | ND |
| 26 | ND | ND | 2 | 8 | 2 | ND | ND | 0.5 | ND | ND | 0.5 | ND | ND | ND |
| 27 | 0.25 | 0.25 | 0.5 | 2 | 0.5 | 0.125 | 0.5 | 0.5 | 0.25 | 0.5 | 0.5 | 0.5 | ND | ND |
| 28 | 0.125 | 0.125 | 0.5 | 2 | 0.25 | ND | 0.25 | 0.25 | 0.125 | 0.125 | 0.125 | 0.125 | 0.125 | ≤0.06 |
| 29 | 0.125 | 0.125 | 0.25 | 4 | 0.5 | ≤0.06 | 0.25 | 0.125 | 0.125 | 0.125 | 0.125 | 0.125 | ≤0.06 | ≤0.06 |
| 30 | 0.25 | 0.125 | 0.25 | 2 | 0.5 | ND | 0.125 | 0.25 | 0.25 | 0.25 | <0.06 | 0.125 | ≤0.06 | ≤0.06 |
| 31 | 0.25 | 0.5 | 2 | 4 | 1 | ND | 0.5 | 0.5 | 0.5 | 0.5 | 0.5 | 0.25 | 0.25 | 0.25 |
| 32 | 0.5 | 1 | 1 | 2 | 1 | ND | ND | ND | ND | ND | ND | ND | ND | ND |
| 33 | ≤0.06 | 0.125 | 0.125 | 2 | 0.125 | ND | ≤0.06 | ≤0.06 | ≤0.06 | ≤0.06 | ≤0.06 | ≤0.06 | ≤0.06 | ≤0.06 |
| 34A | ≤0.06 | 0.125 | 0.125 | 2 | 0.25 | ND | 0.125 | 0.125 | 0.125 | 0.125 | ≤0.06 | ≤0.06 | ≤0.06 | ≤0.06 |
| 34B | <0.06 | 0.125 | ND | 4 | ND | ND | 0.125 | ND | 0.125 | 0.25 | <0.06 | ≤0.06 | ≤0.06 | ≤0.06 |
| 35 | ND | ND | 4 | 16 | 4 | ND | 0.125 | 0.5 | 0.125 | 0.25 | 0.5 | ≤0.06 | ≤0.06 | ≤0.06 |
| 36 | 0.25 | 0.125 | 0.5 | 4 | 1 | ND | 0.125 | 0.25 | 0.25 | 0.125 | 0.5 | 0.25 | 0.125 | 0.125 |
| 37 | 0.125 | ≤0.06 | 0.125 | 2 | 0.125 | ND | ≤0.06 | ≤0.06 | ≤0.06 | 0.125 | ≤0.06 | ≤0.06 | ≤0.06 | ≤0.06 |

TABLE 5-continued

MIC Values (micrograms/mL) for Example Compounds in 1:1 combination with Rifampicin

| Example | E. coli ATCC25922 | E. coli NCTC9001 | K. pneumoniae ATCC-BAA-2146 | K. pneumoniae CCUG-59348 | K. pneumoniae NCTC 13438 | K. pneumoniae ATCC 4352 | P. aeruginosa ATCC-47 | P. aeruginosa CCUG 59626 | P. aeruginosa ATCC 27853 | P. aeruginosa ATCC CRM-9027 | A. baumannii NCTC 13424 | A. baumannii CCUG57249 | A. baumannii ATCC BAA-747 | A. baumannii NCTC 13423 |
|---|---|---|---|---|---|---|---|---|---|---|---|---|---|---|
| 38 | 0.5 | ND | 0.5 | 2 | ND | ND | 0.25 | 0.5 | 0.25 | 0.5 | 0.25 | 0.25 | 0.25 | ND |
| 39 | ≤0.06 | 0.125 | ND | 1 | ND | ND | 0.125 | 0.125 | 0.125 | 0.25 | 0.125 | ≤0.06 | 0.125 | ≤0.06 |
| 40 | ND | ND | 2 | 8 | ND | ND | ND | 0.5 | ND | ND | ND | ND | ND | ND |
| 41 | ≤0.06 | 0.125 | ND | 2 | ND | ND | ≤0.06 | 0.125 | 0.125 | 0.25 | ≤0.06 | ≤0.06 | ≤0.06 | ≤0.06 |
| 42 | ≤0.06 | 0.125 | 0.125 | 4 | ND | ND | ≤0.06 | 0.125 | 0.125 | 0.25 | 0.125 | ≤0.06 | 0.125 | ≤0.06 |
| 43 | 0.125 | 0.125 | 0.25 | 2 | ND | ND | 0.125 | 0.125 | 0.125 | 0.125 | 0.125 | ≤0.06 | 0.125 | ≤0.06 |
| 44 | 0.125 | 0.5 | 1 | 4 | ND | 0.125 | 1 | 0.5 | 0.5 | 0.5 | 0.125 | 0.125 | 0.25 | 0.125 |
| 45 | ≤0.06 | ND | 0.5 | 1 | ND | 0.25 | 0.25 | 0.25 | 0.5 | 0.5 | 0.125 | 0.25 | ND | 0.125 |
| 46 | 0.125 | 0.25 | 1 | 2 | ND | 0.125 | 2 | 1 | 1 | 1 | ≤0.06 | ≤0.06 | ≤0.06 | 0.125 |
| 47 | ≤0.06 | 0.125 | 0.25 | ND | ND | 0.125 | 2 | 1 | 1 | 1 | 0.125 | 0.125 | 0.125 | 0.125 |
| 48 | 0.25 | 0.5 | 2 | 2 | ND | 0.25 | 2 | 0.25 | ND | 0.125 | ≤0.06 | ≤0.06 | ≤0.06 | ND |
| 49 | ND | ND | 2 | 8 | ND | ND | ND | 0.25 | ND | ND | 0.125 | 0.125 | 0.125 | 0.125 |
| 50 | ≤0.06 | 0.125 | 0.25 | 8 | ND | ≤0.06 | 0.25 | 0.25 | 0.125 | 0.125 | ≤0.06 | ≤0.06 | ≤0.06 | 0.125 |
| 51 | 0.125 | 0.5 | 1 | 4 | ND | 0.125 | 0.5 | 0.5 | 0.25 | 0.25 | 0.125 | 0.125 | 0.125 | 0.125 |
| 52 | ≤0.06 | ND | 1 | 8 | ND | 0.125 | ND | 0.125 | 0.125 | ND | ND | ND | ≤0.06 | ND |
| 53 | 0.125 | ND | 1 | 4 | ND | ≤0.06 | ND | ≤0.06 | ≤0.06 | ND | ND | ND | ND | ND |
| 54 | 0.25 | ND | 1 | 4 | ND | 0.125 | ND | 0.25 | 0.25 | ND | ND | ND | ND | ND |
| 55 | 0.125 | ND | 1 | 4 | ND | ND | ND | 0.25 | ND | ND | ND | ND | ND | ND |
| A1 | 0.125 | 0.125 | 0.25 | 2 | 0.5 | 0.125 | ≤0.06 | 0.125 | 0.125 | ND | ≤0.06 | ≤0.06 | ≤0.06 | ≤0.06 |

TABLE 5A

MIC Values (micrograms/mL) for Example and Reference Compounds in 1:1 combination with Rifampicin

| Example | E. coli ATCC25922 | E. coli NCTC9001 | K. pneumoniae ATCC-BAA-2146 | K. pneumoniae CCUG-59348 | K. pneumoniae NCTC 13438 | P. aeruginosa ATCC-47 | P. aeruginosa CCUG 59626 |
|---|---|---|---|---|---|---|---|
| C3 | ND | ND | 2 | 8 | 2 | ND | 1 |
| 5 | ND | ND | 1 | 2 | 1 | ND | 0.25 |
| 55 | 0.125 | ND | 1 | 4 | ND | ND | 0.25 |
| C4 | 0.25 | 0.5 | 1 | 2 | 0.5 | 1 | 0.25 |
| 33 | ≤0.06 | 0.125 | 0.125 | 2 | 0.125 | ≤0.06 | ≤0.06 |
| 29 | 0.125 | 0.25 | 0.25 | 4 | 0.5 | 0.25 | 0.125 |
| 37 | 0.125 | ≤0.06 | 0.125 | 2 | 0.125 | ≤0.06 | ≤0.06 |
| C5 | ND | ND | 1 | 4 | 2 | ND | 0.25 |

| Example | P. aeruginosa ATCC 27853 | P. aeruginosa ATCC CRM-9027 | A. baumannii NCTC 13424 | A. baumannii CCUG57249 | A. baumannii ATCC BAA-747 | A. baumannii NCTC 13423 |
|---|---|---|---|---|---|---|
| C3 | ND | ND | ND | ND | ND | ND |
| 5 | ND | ND | ND | ND | ND | ND |
| 55 | 0.25 | ND | ND | ND | ND | ND |
| C4 | 0.5 | 0.5 | 0.25 | 0.25 | 0.25 | 0.125 |
| 33 | ≤0.06 | ≤0.06 | ≤0.06 | ≤0.06 | ≤0.06 | ≤0.06 |
| 29 | 0.125 | 0.125 | 0.125 | 0.125 | ≤0.06 | ≤0.06 |
| 37 | ≤0.06 | 0.125 | ≤0.06 | ≤0.06 | ≤0.06 | ≤0.06 |
| C5 | ND | ND | ND | ND | ND | ND |

Table 5B shows the effect of altering the ratio of the compound to rifampicin in the combination. Combinations with rifampicin, Colistin, Polymyxin B nonapeptide and Example Compound 10 were examined as 1:3, 1:1 and 3:1 ratios. MIC values (microgram/mL) refer to the total drug concentration (i.e. test agent plus Rifampicin). The values obtained were within the 2-fold variation seen in the MIC test.

TABLE 5B

MIC Values (micrograms/mL) for Example Compounds with Altered Rifampicin Ratios

| Compound | Ratio of Compound to Rifampicin | K. pneumoniae ATCC-BAA-2146 | K. pneumoniae CCUG-59348 | K. pneumoniae NCTC 13438 |
|---|---|---|---|---|
| PMBN | 1:1 | 2 | 4 | 2 |
| PMBN | 1:3 | 2 | 4 | 2 |
| PMBN | 3:1 | 2 | 8 | 2 |
| Colistin | 1:1 | 1 | 2 | 2 |
| Colistin | 1:3 | 4 | 4 | 2 |
| Colistin | 3:1 | 1 | 1 | 1 |
| 10 | 1:3 | 0.5 | 1 | 0.5 |
| 10 | 1:1 | 0.5 | 1 | 0.5 |

Sole Activity

Table 6 below shows the activity, shown by way of MIC values, of Example Compounds in the absence of Rifampicin.

TABLE 6

MIC Values (micrograms/mL) for Example Compounds in the absence of Rifampicin

| Example | E. coli ATCC25922 | E. coli NCTC9001 | K. pneumoniae ATCC-BAA2146 | K. pneumoniae CCUG-59348 | K. pneumoniae NCTC-13438 | K. pneumoniae ATCC 4352 | P. aeruginosa ATCC-47 | P. aeruginosa CCUG 59626 | P. aeruginosa ATCC27853 | P. aeruginosa ATCCCRM-9027 | A. baumannii ATCC13424 | A. baumannii CCUG 57249 | A. baumannii ATCCBAA-747 | A. baumannii NCTC13423 |
|---|---|---|---|---|---|---|---|---|---|---|---|---|---|---|
| PMB | 1 | 1 | 2 | 16 | 1 | 1 | 2 | 0.5 | 0.5 | 0.25 | 1 | 1 | 0.5 | 0.5 |
| 1 | 2 | 2 | ND | >32 | ND | 1 | ND | 2 | 0.5 | 0.25 | ND | ND | 2 | 1 |
| 2 | 2 | 8 | ND | ND | ND | 0.5 | ND | ND | 0.5 | 0.25 | ND | ND | 8 | 0.5 |
| 3 | 2 | ND | >32 | >32 | >32 | 0.125 | ND | ND | 0.25 | 0.25 | ND | ND | 1 | 1 |
| 4 | 2 | 8 | >32 | >32 | >32 | 1 | ND | ND | 0.25 | 0.125 | ND | ND | ND | ND |
| 6 | 2 | 2 | ND | ND | ND | 0.5 | ND | ND | 0.125 | 0.125 | ND | ND | 8 | 4 |
| 7 | ND | ND | ND | >32 | ND | 0.5 | ND | ND | 0.125 | 0.125 | ND | ND | 1 | 1 |
| 8 | 32 | 4 | ND | ND | ND | 8 | 1 | ND | ND | ND | ND | 2 | ND | ND |
| 9 | 0.5 | ND | 32 | >32 | ND | 0.5 | ND | ND | ND | 2 | ND | 2 | 4 | 2 |
| 10 | 2 | 4 | ND | ND | >32 | 1 | 1 | ND | 2 | 0.25 | ND | 0.5 | 0.5 | 0.125 |
| 11 | 0.5 | ND | ND | ND | ND | 0.5 | ND | ND | 0.125 | ND | 1 | ND | 16 | 4 |
| 13 | 1 | ND | ND | ND | ND | >32 | ND | ND | 0.25 | 2 | ND | ND | ND | ND |
| 14 | 4 | ND | ND | ND | ND | 2 | ND | ND | 1 | ND | ND | ND | ND | ND |
| 15 | 4 | ND | ND | ND | ND | 8 | ND | ND | 0.5 | ND | ND | ND | ND | ND |
| 16 | 0.5 | ND | ND | ND | ND | 0.5 | ND | ND | 0.25 | ND | ND | ND | ND | ND |
| 17 | 2 | 16 | 8 | >32 | 32 | 0.125 | ND | 0.25 | 0.125 | ND | ND | ND | ND | ND |
| 19 | 8 | ND | ND | ND | ND | 8 | ND | ND | 4 | ND | ND | ND | ND | ND |
| 20 | 2 | >32 | ND | ND | ND | 0.125 | ND | ND | <0.06 | ND | ND | ND | ND | ND |
| 21 | 4 | >32 | >32 | >32 | >32 | 0.25 | ND | ND | 0.125 | ND | ND | ND | ND | ND |
| 22 | 8 | >32 | >32 | >32 | >32 | 0.5 | ND | ND | 0.125 | 0.5 | ND | ND | 1 | 0.5 |
| 23 | 16 | ND | ND | ND | ND | 1 | ND | ND | 0.25 | ND | ND | ND | ND | ND |
| 24 | >32 | ND | ND | >32 | >32 | 0.5 | ND | ND | 0.125 | ND | ND | ND | ND | ND |
| 25 | 8 | ND | ND | ND | ND | 4 | ND | ND | 0.5 | ND | ND | ND | ND | ND |
| 26 | >32 | ND | ND | ND | ND | 4 | ND | ND | 0.125 | ND | ND | ND | ND | ND |
| 27 | 2 | ND | ND | >8 | >8 | 2 | 2 | 0.25 | 0.125 | ND | 4 | 4 | ND | ND |
| 28 | ND | 32 | 32 | >32 | 32 | ND | 1 | 0.5 | ND | ND | 1 | 1 | ND | ND |
| 29 | ND | ND | >32 | >32 | ND | ND | 2 | 0.125 | ND | ND | 2 | ND | ND | ND |
| 38 | 4 | 8 | 8 | >32 | ND | ND | 0.25 | 0.125 | 0.25 | 0.25 | 1 | 4 | 0.5 | 0.25 |
| 39 | 2 | 4 | 32 | >32 | ND | 1 | 1 | ≤0.06 | 0.125 | 0.125 | 0.125 | 0.5 | 1 | 0.125 |
| 43 | 2 | 16 | 4 | 32 | ND | 0.5 | 1 | ≤0.06 | 0.125 | 0.125 | 0.25 | 2 | 2 | 1 |
| 45 | ND | 16 | 2 | 32 | ND | 0.25 | 0.25 | 0.125 | 0.25 | ≤0.06 | 1 | 0.25 | 0.5 | 0.5 |
| 47 | 4 | 4 | 0.5 | >32 | ND | 0.5 | 8 | 1 | 4 | 0.5 | ND | ND | 0.25 | 0.25 |
| 48 | ND | ND | 4 | >32 | ND | 4 | 32 | 2 | 32 | 0.5 | 4 | 4 | 4 | 2 |
| 50 | >32 | >32 | 16 | >32 | ND | 2 | 32 | 0.25 | ND | 0.125 | 4 | 4 | 4 | 8 |
| 51 | >32 | >32 | >32 | >32 | ND | 2 | 32 | 0.25 | ND | 0.5 | 4 | 4 | 4 | 0.25 |
| A1 | 0.5 | 8 | ND | ND | ND | 1 | 0.25 | ≤0.06 | 0.125 | 0.5 | 2 | 2 | 1 | 0.25 |

Combination Activity

Tables 7A to 7I show selected example compounds in 1:1 ratio with other antibacterial agents. MICs refer to the total drug concentration. Thus, where a 1:1 combination is used, this is the amount of the test compound plus the second agent. For comparison, the MIC values for the second agent alone are also given.

TABLE 7A

MIC Values (microgram/mL) for Example Compounds in 1:1 combination with Vancomycin

| Example | Second Agent | *E. coli* NCTC9001 | *K. pneumoniae* CCUG 59348 | *K. pneumoniae* NCTC 13442 | *K. pneumoniae* CCUG 59626 |
|---|---|---|---|---|---|
| Vancomycin | none | >32 | >32 | >32 | >32 |
| Colistin | none | 1 | 32 | 2 | 0.5 |
| 1 | none | 4 | >32 | 8 | 2 |
| 10 | none | 4 | >32 | >32 | 0.25 |
| 17 | none | ND | >32 | >32 | 0.25 |
| Colistin | Vancomycin | 4 | >32 | 8 | 2 |
| 1 | Vancomycin | 4 | >32 | 8 | 2 |
| 10 | Vancomycin | 16 | >32 | 4 | ND |
| 17 | Vancomycin | 16 | >32 | 32 | 0.25 |

TABLE 7B

MIC Values (micrograms/mL) for Example Compounds with in 1:1 combination with Ciprofloxacin

| Example | Second Agent | *E. coli* CCUG 59342 | *E. coli* ATCC25922 | *E. coli* (NCTC9001) | *K. pneumoniae* CCUG 59348 | *K. pneumoniae* NCTC 13442 |
|---|---|---|---|---|---|---|
| Ciprofloxacin | none | 16 | ≤0.06 | ≤0.06 | >32 | 2 |
| Colistin | none | 0.5 | 1 | 2 | 32 | 2 |
| 1 | none | 1 | 4 | 8 | >32 | 8 |
| 10 | none | 0.5 | 4 | 8 | >32 | >32 |
| 17 | none | 0.25 | ND | 16 | >32 | >32 |
| Colistin | Ciprofloxacin | 1 | ≤0.06 | ≤0.06 | 32 | 1 |
| 1 | Ciprofloxacin | 2 | ≤0.06 | ≤0.06 | 32 | 1 |
| 10 | Ciprofloxacin | 1 | ≤0.06 | ≤0.06 | 32 | 1 |
| 17 | Ciprofloxacin | 0.5 | ≤0.06 | ≤0.06 | >32 | 1 |

| Example | *K. pneumoniae* (ATCC4352) | *K. pneumoniae* ATCC BAA-1706 | *P. aeruginosa* CCUG 59626 | *P. aeruginosa* ATCC 27853 | *A. baumannii* (NCTC 13424) |
|---|---|---|---|---|---|
| Ciprofloxacin | ≤0.06 | 4 | 0.5 | 0.125 | 1 |
| Colistin | 0.5 | 2 | 0.5 | 0.25 | 0.5 |
| 1 | 1 | 4 | 2 | 0.5 | 4 |
| 10 | 0.5 | 0.5 | 0.25 | 0.25 | 2 |
| 17 | 0.125 | ND | 0.25 | 0.125 | 4 |
| Colistin | ≤0.06 | 1 | 1 | 0.125 | 0.5 |
| 1 | ≤0.06 | 0.5 | 1 | 0.125 | 0.5 |
| 10 | ≤0.06 | 0.25 | 0.5 | 0.125 | 0.5 |
| 17 | ≤0.06 | ND | 0.5 | ≤0.06 | 0.5 |

TABLE 7C

MIC Values (micrograms/mL) for Example Compounds in 1:1 combination with Tigecycline

| Example | Second Agent | *E. coli* (NCTC9001) | *K. pneumoniae* CCUG 59348 | *K. pneumoniae* NCTC 13442 | *P. aeruginosa* CCUG 59626 |
|---|---|---|---|---|---|
| Tigecycline | none | 0.125 | 2 | 2 | 16 |
| Colistin | none | 1 | 32 | 2 | 0.5 |
| 1 | none | 4 | >32 | 8 | 2 |
| 10 | none | 4 | >32 | >32 | 0.25 |
| 17 | none | ND | >32 | >32 | 0.25 |
| Colistin | Tigecycline | 4 | >32 | 4 | 1 |
| 1 | Tigecycline | 4 | >32 | 16 | 2 |
| 10 | Tigecycline | 8 | >32 | 16 | 1 |
| 17 | Tigecycline | 16 | >32 | 16 | 0.25 |

TABLE 7D

MIC Values (micrograms/mL) for Example Compounds in 1:1 combination with Meropenem

| Example | Second Agent | E. coli (NCTC9001) | K. pneumoniae CCUG 59348 | K. pneumoniae NCTC 13442 | K. pneumoniae ATCC BAA-1706 | P. aeruginosa CCUG 59626 |
|---|---|---|---|---|---|---|
| Meropenem | none | 0.125 | >32 | 16 | 16 | 16 |
| Colistin | none | 1 | 32 | 2 | 2 | 0.5 |
| 1 | none | 4 | >32 | 8 | 4 | 2 |
| 10 | none | 4 | >32 | >32 | 0.5 | 0.25 |
| 17 | none | ND | >32 | >32 | ND | 0.25 |
| Colistin | Meropenem | 0.25 | >32 | 4 | 4 | 1 |
| 1 | Meropenem | 0.25 | >32 | 8 | 4 | 2 |
| 10 | Meropenem | 0.5 | >32 | 16 | 4 | ND |
| 17 | Meropenem | 0.25 | >32 | 16 | 4 | 0.5 |

TABLE 7E

MIC Values (micrograms/mL) for Example Compounds in 1:1 combination with Aztreonam

| Example | Second Agent | E. coli ATCC25922 | E. coli NCTC 13441 | K. pneumoniae ATCC4352 | K. pneumoniae CCUG 59349 | P. aeruginosa ATCC 10145 | A. baumannii NCTC 13424 |
|---|---|---|---|---|---|---|---|
| Aztreonam | none | ≤0.06 | >32 | ≤0.06 | >32 | 4 | 8 |
| PMB | none | 0.5 | 1 | ND | 0.5 | 0.5 | 0.125 |
| 10 | none | 8 | 8 | 1 | 8 | 0.25 | 0.5 |
| A1 | none | 32 | 16 | 0.5 | 16 | 0.25 | 4 |
| PMB | Aztreonam | 0.125 | 1 | ≤0.06 | 2 | 1 | 1 |
| 10 | Aztreonam | 0.125 | 2 | ≤0.06 | 4 | 1 | 1 |
| A1 | Aztreonam | ≤0.06 | 2 | ≤0.06 | 8 | 0.5 | 4 |

TABLE 7F

MIC Values (micrograms/mL) for Example Compounds in 1:1 combination with Azithromycin

| Example | Second Agent | E. coli ATCC25922 | E. coli NCTC 13441 | K. pneumoniae ATCC4352 | K. pneumoniae CCUG 59349 | P. aeruginosa ATCC 10145 | A. baumannii NCTC 13424 |
|---|---|---|---|---|---|---|---|
| Azithromycin | none | 1 | >32 | 0.25 | >32 | 32 | 8 |
| PMB | none | 0.5 | 1 | ND | 0.5 | 0.5 | 0.125 |
| 10 | none | 8 | 8 | 1 | 8 | 0.25 | 0.5 |
| A1 | none | 32 | 16 | 0.5 | 16 | 0.25 | 4 |
| PMB | Azithromycin | 0.25 | 1 | 0.25 | 2 | 1 | 1 |
| 10 | Azithromycin | 0.125 | 2 | 0.125 | 4 | 1 | 1 |
| A1 | Azithromycin | 0.125 | 2 | 0.125 | 8 | 0.5 | 4 |

MIC values for further examples compounds were obtained and compared against the comparative compounds PMB and oxacillin.

TABLE 7G

MIC Values (micrograms/mL) for Example Compounds in 1:1 combination with with Oxacillin

| Example | Second Agent | E. coli (ATCC25922) | K. pneumoniae (ATCC4352) |
|---|---|---|---|
| Oxacillin | NA | >32 | 16 |
| PMB | none | 0.5 | ND |
| 10 | none | 8 | 1 |
| A1 | none | 32 | 0.5 |
| PMB | Oxacillin | 2 | 4 |
| 10 | Oxacillin | 8 | ND |
| A1 | Oxacillin | 32 | ND |

TABLE 7H

MIC Values (micrograms/mL) for Example Compounds in 1:1 combination with with Novobiocin

| Example | Second Agent | E. coli ATCC25922 | E. coli NCTC 13441 | K. pneumoniae ATCC4352 | K. pneumoniae CCUG 59349 | P. aeruginosa ATCC 10145 | A. baumannii NCTC 13424 |
|---|---|---|---|---|---|---|---|
| Novobiocin | none | 16 | >32 | 0.25 | >32 | >32 | 4 |
| PMB | none | 0.5 | 1 | ND | 0.5 | 0.5 | 0.125 |

TABLE 7H-continued

MIC Values (micrograms/mL) for Example Compounds in 1:1 combination with with Novobiocin

| Example | Second Agent | E. coli ATCC25922 | E. coli NCTC 13441 | K. pneumoniae ATCC4352 | K. pneumoniae CCUG 59349 | P. aeruginosa ATCC 10145 | A. baumannii NCTC 13424 |
|---|---|---|---|---|---|---|---|
| 10 | none | 8 | 8 | 1 | 8 | 0.25 | 0.5 |
| A1 | none | 32 | 16 | 0.5 | 16 | 0.25 | 4 |
| PMB | Novobiocin | 0.5 | 1 | 0.25 | 1 | 1 | 0.125 |
| 10 | Novobiocin | 0.5 | 0.5 | 0.125 | 1 | 0.5 | 0.125, 0.5 |
| A1 | Novobiocin | 1 | 1 | 0.125 | 1 | 0.5 | 0.5 |

TABLE 7I

MIC Values (micrograms/mL) for Example Compounds in 1:1 combination with Fusidic acid

| Example | Second Agent | E. coli (ATCC25922) | K. pneumoniae (ATCC4352) |
|---|---|---|---|
| Fusidic acid | none | >32 | 16 |
| PMB | none | 0.5 | ND |
| 10 | none | 8 | 1 |
| A1 | none | 32 | 0.5 |
| PMB | Fusidic acid | 2 | 1 |
| 10 | Fusidic acid | 1 | 0.5 |
| A1 | Fusidic acid | 4 | 0.5 |

In Vitro Renal Cell Toxicity Assay

The renal cell toxicity of the compounds was assessed in an in vitro assay using the HK-2 cell line, an immortalized proximal tubule cell line derived from a normal human kidney. The endpoint to describe the toxicity of the compounds was the reduction of resazurin correlating with the metabolic activity of the cells. Cells were cultured in 150 cm$^2$ flasks in 25 mL supplemented KSF (with 5 ng/mL EGF and 50 μg/mL BPE). Cells were maintained at 70% confluence with a maximum of 25 passages.

Day 1: Media was removed and cells were washed with 10 ml DPBS. Six ml of a 0.25% trypsin solution with EDTA was then added to the flask and the cells returned to the incubator. After 1 to 2 minutes incubation, 14 mL media was added to the flask to inactivate the trypsin. The cell suspension was transferred to a centrifuge tube and the cells pelleted at 1000 rpm for 6 minutes. The cell pellet was then resuspended in fresh media supplemented with EGF and BPE. The cell number was counted and cells were diluted to 46875 cells/mL in fresh medium supplemented with EGF and BPE. 7500 cells were dispensed in each well in a volume of 160 μl and incubated at 37° C. for 24 h.

Day 2: Test compounds were prepared directly into the media, or from stock solutions to result in no more than 0.5% DMSO, or 5% water in the final assay. Nine point concentrations were prepared from 1000 μg/mL to 1.95 μg/mL in two-fold dilutions in fresh medium. The microtiter plates were removed from the incubator and the media replaced with 100 μL of the dilutions of the compound solution. Every set of concentration was done in triplicate, and positive and negative controls were added to each plate. The plates were then incubated for 24 h at 37° C. with 5% CO$_2$ in a humidified atmosphere.

Day 3: The reagent containing the resazurin (CellTiter-Blue, Promega) was diluted in PBS (1:4) and added at 20% (v/v) to each well. The plates were then incubated at 37° C. for 2 h before the fluorescent reduction product was detected.

Media only background values were subtracted before the data was analysed using GraphPad Prism. Compound concentration values were plotted as log values to enable a dose-response curve to be fitted and IC$_{50}$ values determined (Tables 8A and 8B).

TABLE 8A

IC$_{50}$ Data for Example Compounds

| Example | IC$_{50}$ HK-2 cells μg/mL[a] |
|---|---|
| Polymyxin B | 11[b] |
| Colistin | 28 |
| CB-182,804 | 22 |
| 1 | 87 |
| 2 | 138 |
| 3 | 82 |
| 4 | 154 |
| 5 | 302 |
| 6 | 133 |
| 7 | 310 |
| 8 | 1000[c] |
| 9 | 158 |
| 10 | 60 |
| 11 | >500 |
| 12 | >500 |
| 13 | 157[c] |
| 15 | 500[c] |
| 16 | 173 |
| 17 | 101 |
| 18 | 47 |
| 19 | 128 |
| 20 | 118 |
| 21 | 108 |
| 22 | 82 |
| 23 | 133 |
| 24 | 93 |
| 25 | 500 |
| 26 | 1000[c] |
| 27 | 86 |
| 30 | 134 |
| 34 | 88 |
| 37 | 189 |
| 39 | 14 |
| 41 | 104 |
| 43 | 245 |
| 44 | >500 |
| 45 | 231 |
| 46 | 231 |

[a]Mean values of up to 6 independent studies
[b]Mean value of 16 independent studies
[c]Solubility issues noted at top concentration

TABLE 8B

HK-2 cell IC$_{50}$ Data for Example Compounds in the Presence of Rifampicin

| Example | Second Agent | IC$_{50}$ HK-2 cells μg/mL |
|---|---|---|
| Polymyxin B | Rifampicin | 7.2 |
| 10 | Rifampicin | 24 |

TABLE 8B-continued

HK-2 cell IC$_{50}$ Data for Example Compounds in the Presence of Rifampicin

| Example | Second Agent | IC$_{50}$ HK-2 cells µg/mL |
|---|---|---|
| 17 | Rifampicin | 26 |
| 27 | Rifampicin | 28 |

IC$_{50}$ refers to the total drug concentration (test agent plus rifampicin). The ratio of compound to rifampicin was 1:1 (wt:wt).

Sole Activity—Additional Data

Table 6A below shows the activity, shown by way of MIC values, of Example Compounds in the absence of a second agent together with the toxicity against the HK-2 cell line (measured in relation to IC$_{50}$ values and expressed relative to the value for polymyxin B)

MICs were determined as described herein, except that a different supplier of Cation-adjusted MHB was used. Examples 37 and 39 were re-tested for direct comparison. HK-2 cell IC$_{50}$ values were determined as described herein. Values are reported relative to Polymyxin B.

TABLE 6A

MIC Values (micrograms/mL) for Example Compounds in the absence of Rifampicin and HK-2 cell toxicity for Example Compounds expressed as IC$_{50}$ values relative to the value for polymyxin B

| Ex. | E. coli NCTC 13441 | E. coli ATCC 25922 | K. pneumoniae BAA-2146 | K. pneumoniae ATCC 4352 | P. aeruginosa CCUG 59347 | P. aeruginosa ATCC 27853 | A. baumannii NCTC 13424 | A. baumannii ATCC BAA-747 | HK-2 IC$_{50}$ rel to PMB |
|---|---|---|---|---|---|---|---|---|---|
| PMB | 0.25 | 0.25 | 0.5 | 0.25 | 0.5 | 0.5 | 0.5 | 0.25 | 1 |
| 37 | 0.5 | 0.5 | 0.25 | 0.25 | 2 | 0.5 | 1 | 2 | 21 |
| 39 | 2 | 2 | 2 | 1 | 0.5 | 0.25 | 2 | 1 | 1.5-2 |
| A1 | 2 | 4 | ND | ND | ND | ND | ND | ND | 8 |
| A2 | >8 | 4 | ND | 8 | 4 | 2 | >8 | >8 | ND |
| A3 | 0.25 | 0.25 | 0.25 | 0.25 | 1 | 0.5 | 1 | 2 | 4 |
| A4 | 4 | 1 | ND | 2 | 2 | 2 | >8 | >8 | ND |
| A5 | ND | 0.5 | 0.5 | 0.5 | 0.5 | 0.25 | 2 | 1 | ND |
| A6 | 2 | 4 | ND | 4 | 0.5 | 0.25 | 4 | 2 | 3 |
| A7 | >8 | >8 | ND | >8 | >8 | 1 | 8 | 4 | 4.8 |
| A8 | >8 | >8 | ND | >8 | 4 | 2 | >8 | >8 | ND |
| A9 | >8 | >8 | ND | >8 | >8 | 2 | >8 | >8 | ND |
| A10 | 1 | 1 | ND | 0.5 | 0.25 | 0.25 | 2 | 2 | 3.7 |
| A11 | 8 | >8 | ND | 8 | 2 | 1 | 4 | 4 | ND |
| A12 | >8 | >8 | ND | >8 | 4 | 2 | 8 | 8 | ND |
| A13 | 8 | >8 | >8 | >8 | 1 | 0.5 | 8 | 8 | 10 |
| A14 | 2 | 2 | ND | 1 | 1 | 1 | 8 | 8 | 5.3 |
| A15 | 8 | 8 | ND | 4 | 8 | 4 | >8 | >8 | ND |
| A16 | >8 | >8 | >8 | >8 | >8 | 1 | >8 | >8 | ND |
| A17 | 4 | 8 | 4 | 4 | 0.5 | 0.25 | 8 | 8 | 5.5 |
| A18 | 4 | 8 | 4 | 4 | 1 | 0.5 | 8 | 4 | 3.2 |
| A19 | 4 | 8 | 8 | 8 | 2 | 1 | 4 | 4 | ND |
| A20 | >8 | >8 | >8 | >8 | >8 | >8 | >8 | >8 | ND |
| A21 | >8 | >8 | >8 | >8 | >8 | >8 | >8 | >8 | ND |
| A22 | >8 | >8 | >8 | >8 | 2 | 1 | 8 | 8 | 7.4 |
| A23 | >8 | >8 | >8 | >8 | >8 | 8 | 4 | 2 | ND |
| A24 | >8 | >8 | >8 | 8 | 2 | 1 | >8 | >8 | ND |
| A25 | >8 | >8 | >8 | 8 | 4 | 2 | >8 | >8 | ND |
| A26 | 2 | 2 | 1 | 0.5 | 2 | 1 | 1 | 2 | ND |
| A27 | >8 | >8 | >8 | >8 | 4 | ND | >8 | 8 | ND |
| A28 | >8 | >8 | >8 | >8 | 4 | 2 | >8 | >8 | ND |
| A29 | >8 | >8 | >8 | >8 | >8 | 0.25 | 4 | 2 | ND |
| A30 | 1 | ND | 1 | 0.5 | 1 | 0.5 | 8 | 8 | ND |
| A31 | 2 | 8 | >8 | 2 | 2 | 0.5 | >8 | >8 | ND |
| A32 | 0.5 | 0.5 | 0.25 | 0.5 | 1 | 0.5 | 2 | 2 | ND |
| A33 | 0.5 | 0.25 | 0.5 | 0.5 | 0.5 | 0.25 | 1 | 2 | 9.7 |
| A34 | >8 | 8 | >8 | 8 | 2 | 0.5 | >8 | >8 | ND |
| A35 | 2 | 1 | 2 | 2 | 1 | 0.25 | 8 | 8 | ND |
| A36 | 2 | 2 | 8 | 1 | 4 | 1 | 8 | 8 | ND |
| A37 | >8 | >8 | >8 | >8 | >8 | 2 | >8 | >8 | ND |
| A38 | 2 | 0.5 | 2 | 0.5 | 1 | 0.5 | 2 | 1 | ND |
| A39 | 8 | >8 | >8 | 8 | 4 | 2 | >8 | >8 | ND |
| A40 | 4 | 8 | 8 | 4 | 4 | 2 | >8 | >8 | ND |
| A41 | 4 | 4 | 4 | 4 | 2 | 2 | >8 | >8 | ND |
| A42 | 1 | 2 | 1 | 2 | 2 | 0.5 | 4 | 4 | ND |
| A43 | >8 | 8 | ND | >8 | 8 | 4 | >8 | >8 | ND |
| A44 | 2 | 2 | ND | 2 | 2 | 1 | 4 | 2 | ND |
| A45 | 2 | 2 | ND | 1 | 1 | 0.5 | >8 | >8 | ND |
| A46 | 2 | 2 | 2 | 2 | 2 | 1 | 2 | 8 | ND |
| A47 | 8 | >8 | 8 | >8 | 8 | 2 | 4 | 8 | ND |
| A48 | 1 | 1 | 2 | 0.5 | 4 | 1 | 2 | 4 | ND |

TABLE 6A-continued

MIC Values (micrograms/mL) for Example Compounds in the
absence of Rifampicin and HK-2 cell toxicity for Example Compounds
expressed as $IC_{50}$ values relative to the value for polymyxin B

|     | E. coli NCTC 13441 | K. pneumoniae ATCC 25922 | BAA-2146 | ATCC 4352 | P. aeruginosa CCUG 59347 | ATCC 27853 | A. baumannii NCTC 13424 | ATCC BAA-747 | HK-2 $IC_{50}$ rel to PMB |
|-----|------|------|------|------|------|------|------|------|------|
| Ex. |      |      |      |      |      |      |      |      |      |
| A49 | 4    | 4    | >8   | 2    | 4    | 2    | >8   | >8   | ND   |
| A50 | 2    | 1    | 2    | 0.25 | 2    | 1    | 2    | ND   | ND   |

The MIC values were compared to compounds known from the literature. The data is in table 6B. C2 (CB-182,804) is a polymyxin decapeptide derivative described by Cubist (shown as compound 5 in WO 2010/075416), C1 is NAB-739 (as described by Vaara in, for example, WO 2008/01773).

In Vivo Efficacy Against *E. coli* Thigh Infection in Mice—Combination with Rifampicin The in vivo efficacy of two example compounds (Example Compounds 10 and A1) in 1:1 combination with rifampicin was evaluated in a mouse thigh infection model of *E. coli*. The results are summarized in Table 9.

Groups of 4 male specific-pathogen-free CD-1 mice were used. Mice were rendered temporarily neutropenic by immunosuppression with cyclophosphamide at 150 mg/kg 4 days before infection and 100 mg/kg 1 day before infection by intraperitoneal injection. At 24 hours post the second round of immunosuppression, mice were infected with *E. coli* ATCC25922 intramuscularly into both lateral thigh muscles under inhaled anaesthesia using ~6.5×10$^5$ CFU/mouse thigh.

Test compounds and Polymyxin B were administered at doses of 0.0625, 0.25 and 2.5 mg/kg in conjunction with Rifampicin at the equivalent dose. This gave combined dose levels of 0.125, 0.5 and 5 mg/kg for each combination (Table 9). In addition, Polymyxin B was administered in monotherapy at doses of 0.125, 0.5 and 5 mg/kg. Compounds were administered in solution by intravenous (IV) injection into the lateral tail vein. This was performed three times at 1, 3.5 and 6 hours post infection at a dose volume of 10 mL/kg (0.25 mL/25 g mouse). The vehicle control group was treated with vehicle (0.9% saline for injection) also at 10 mL/kg IV thrice at 1, 3.5 and 6 hours post infection.

At 1 hour post infection, 4 animals were humanely euthanized using pentabarbitone overdose to provide a pre-treatment control group. At 9 hours post infection, the clinical condition of all animals was assessed prior to them being humanely euthanized by pentabarbitone overdose. Animal weight was determined before both thighs were removed and weighed individually. Individual thigh tissue samples were homogenized in ice cold sterile phosphate buffered saline. Thigh homogenates were then quantitatively cultured onto CLED agar and incubated at 37° C. for 24 hours before colonies were counted.

The example compounds 10 and A1 in 1:1 combination with rifampicin at a total concentration of 5 mg/kg/dose demonstrated an efficacy superior to Polymyxin B alone, and comparable to that of polymyxin B 1:1 with rifampicin, with over 4 $\log_{10}$ reduction in bacterial counts.

TABLE 9

In vivo efficacy versus *E. coli* ATCC25922
Thigh Infection in Neutropenic Mice

| Treatment | Dose mg/kg | Log reduction from vehicle CFU/g |
|-----------|------------|----------------------------------|
| Pre-treatment | NA | 2.03 |
| Vehicle | NA | 0.00 |
| Polymyxin B | 0.125 | −0.36 |
|  | 0.5 | 1.93 |
|  | 4.7 | 3.17 |
| Polymyxin B/ | 0.0625/0.0625 | −0.47 |
| Rifampicin | (0.125) |  |
|  | 0.25/0.25 | 0.74 |
|  | (0.5) |  |
|  | 2.5/2.5 | 4.95 |
|  | (5) |  |
| 10/Rifampicin | 0.0625/0.0625 | −0.14 |
|  | (0.125) |  |
|  | 0.25/0.25 | −0.43 |
|  | (0.5) |  |
|  | 2.5/2.5 | 4.68 |
|  | (5) |  |
| A1/Rifampicin | 0.0625/0.0625 | 0.12 |
|  | (0.125) |  |
|  | 0.25/0.25 | 0.27 |
|  | (0.5) |  |
|  | 2.5/2.5 | 4.51 |
|  | (5) |  |

In Vivo Nephrotoxicity

A model of nephrotoxicity of polymyxins (adapted from Yousef et al. Antimicrob. Agents Chemother. 2011, 55, 4044-4049) was established in rats. The Example Compounds 1, 4, and 10 were examined in the model and compared to Colistin (in its sulphate form). After one week acclimatisation, male Sprague-Dawley rats were surgically prepared with a jugular cannula and were housed individually, as required, either in pre-assigned housing cages or metabolic cages. Colistin and the Example Compounds were prepared in saline.

Compounds were introduced via the jugular cannula twice a day 7 hours apart for seven days. Each dose was increased progressively for three days up to the top dose that was then administered until termination of the study. Twenty-four hour urine collection (on ice) was performed at pre-dose and on days 4 and 7. The dose regimen is set out in Table 10 below.

TABLE 10

Dose regimen used in the in vivo nephrotoxicity study

| Dose Regimens | Day 1 a.m. | Day 1 p.m. | Day 2 a.m. | Day 2 p.m. | Day 3 a.m. | Day 3 p.m. | Day 4 to Day 7 or Day 10 a.m. | Day 4 to Day 7 or Day 10 p.m. |
|---|---|---|---|---|---|---|---|---|
| 2 mg/kg bid | 0.25 | 0.5 | 0.625 | 0.625 | 0.875 | 1.375 | 2 | 2 |
| 8 mg/kg bid | 1 | 2 | 2.5 | 2.5 | 3.5 | 5.5 | 8 | 8 |

The doses in the table are indicated in mg drug base/kg (free base).

The activity in urine of the N-acetyl-beta-D-glucosaminidase (NAG) was determined spectrophotometrically using the NAG assay kit from Roche Applied Science. Biomarkers of kidney injury were determined using the Kidney Injury Panel II from the Multi-Spot® Assay System (Meso Scale Discovery).

Figure 2:
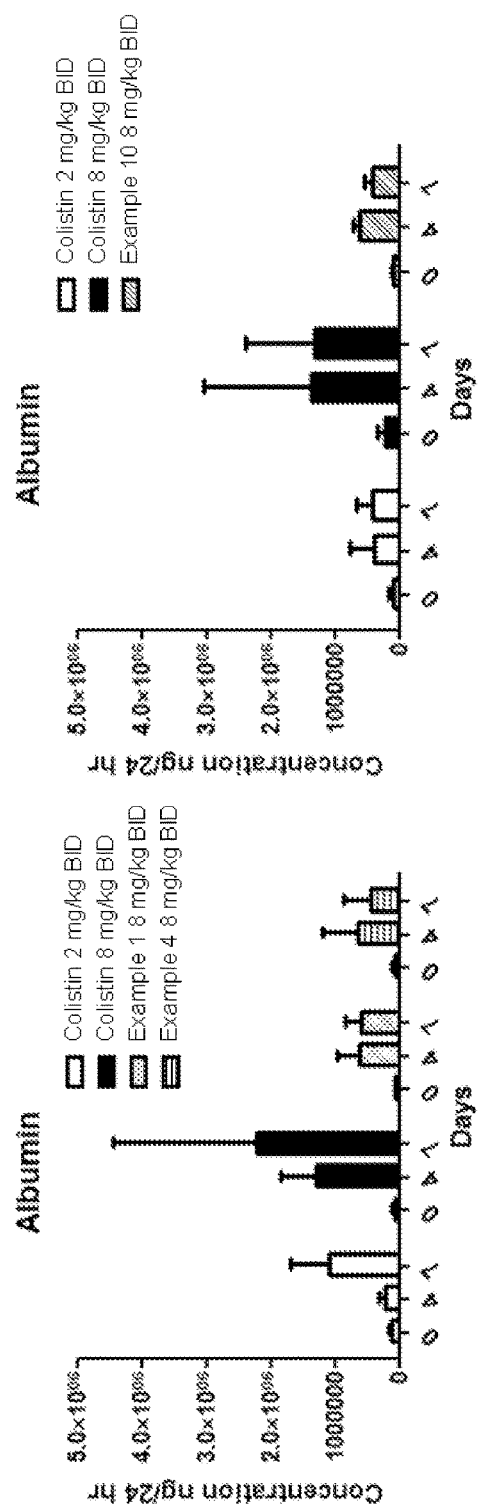
FIG. 2 shows the concentration of albumin (ng/24 h) at days 0, 4 and 7 for compounds 1, 4 and 10 and Colistin. The left-hand graph shows from left to right Colistin (2 mg/kg BID), Colistin (8 mg/kg BID), compound 1 (8 mg/kg BID) and 4 (8 mg/kg BID). The right-hand graph shows Colistin (2 mg/kg BID), Colistin (8 mg/kg BID) and compound 10 (8 mg/kg BID).
Figure 3:
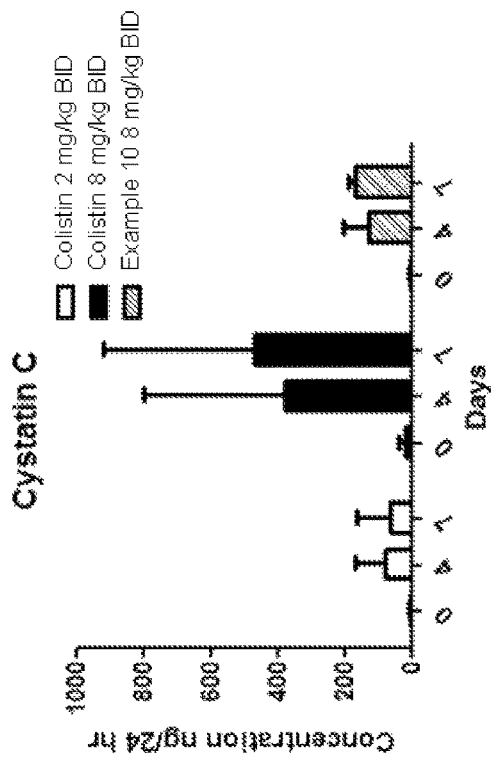
FIG. 3 shows the concentration of cystatin C (ng/24 h) at days 0, 4 and 7 for compounds 1, 4 and 10 and Colistin. The left-hand graph shows from left to right Colistin (2 mg/kg BID), Colistin (8 mg/kg BID), compound 1 (8 mg/kg BID) and 4 (8 mg/kg BID). The right-hand graph shows Colistin (2 mg/kg BID), Colistin (8 mg/kg BID) and compound 10 (8 mg/kg BID).
Figure 3:
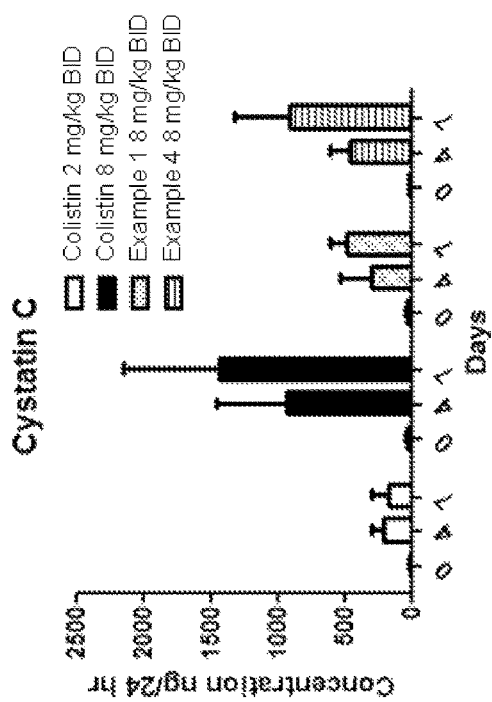

Example Compounds 1, 4, and 10 dosed using the 8 mg/kg regimen showed significantly reduced levels of the renal biomarkers NAG, albumin and cystatin C compared to Colistin at the same dose regimen (see FIGS. 1 to 3). The response was similar to that elicited by Colistin at a maximum concentration of 2 mg/kg.

In Vivo Efficacy Against *E. coli* Thigh Infection in Mice—Example Compounds

The in vivo efficacy of 6 compounds of the invention (Examples 1, 2, 3, 4, 7 and 10) was evaluated in a mouse thigh infection model of *E. coli*. The results are summarized in Table 11 and 11A.

Groups of 5 female specific-pathogen-free CD-1 mice weighing 22±2 g were used. The animals were made neutropenic by intraperitoneal administration of cyclophosphamide on days −4 (150 mg/kg) and −1 (100 mg/kg). On Day 0, animals were inoculated intramuscularly with $10^5$ CFU/mouse of *Escherichia coli* isolate ATCC25922 into the right thigh. At 1 h, the CFU count was determined from 5 mice and the remaining mice (five per group) were treated with a subcutaneous injection of the drug at +1 and 6 hr post-infection. In each study, there were two dose groups per test compound, 1.5 and 5 mg/kg BID, respectively.

The Example Compounds and polymyxin B were prepared in Normal Saline at 2 mg/mL and the solution was adjusted to pH 6-7 by addition of 0.1M $H_2SO_4$ or 4.2% $NaHCO_3$ as required. Twenty-four hours after infection, the mice were euthanized humanely. The muscle of the right thigh of each animal was harvested, homogenized, serially diluted and plated on Brain Heart Infusion agar+0.5% charcoal (w/v) for CFU determination. Decrease of the total CFU of right thigh as compared to control counts at 24 h post-infection was determined for each dose group.

The compounds 1 and 4 at 10 mg/kg/day demonstrated an efficacy comparable to that of polymyxin B with over 3 $log_{10}$ reduction in bacterial counts.

TABLE 11

In vivo Efficacy Versus *E. coli* ATCC25922 Thigh Infections in Neutropenic Mice

| Example No | Total daily dosage (mg/kg) | Mean $log_{10}$ CFU reduction vs. control |
|---|---|---|
| Polymyxin B | 3 | 2.5 [a] |
|  | 10 | 4.2 [a] |
| 1 | 3 | 0.98 [b] |
|  | 10 | 4.48 [b] |
| 2 | 3 | 1.09 |
|  | 10 | 2.15 |
| 3 | 3 | 0 [b] |
|  | 10 | 0.82 [b] |
| 4 | 3 | 0.72 [b] |
|  | 10 | 3.38 [b] |
| 7 | 3 | 1.19 |
|  | 10 | 1.85 |

[a] mean values of 5 independent studies; [b] mean value of 2 independent studies. The doses in the table are indicated in mg sulfate salt/kg.

The in vivo efficacy of the compound of Example 10 was evaluated separately in a mouse thigh infection model of *E. coli.* using the methods described in the examples above. The result is summarized in Table 11A in comparison with Polymyxin B.

TABLE 11A

In vivo Efficacy Versus *E. coli* ATCC25922 Thigh Infections in Neutropenic Mice

| Example | Total daily dosage (mg/kg) | Mean $log_{10}$ CFU reduction vs. control |
|---|---|---|
| Polymyxin B | 3 | 3.75 |
|  | 10 | 4.87 |
| 10 | 3 | 0 |
|  | 10 | 4.05 |

The doses in the table are indicated in mg sulfate salt/kg.

Compound 10 at 10 mg/kg/day demonstrated an efficacy comparable to that of polymyxin B with over 3 $log_{10}$ reduction in bacterial counts.

Using the same procedure as described above, the in vivo efficacy of three compounds of the invention (Examples 1, 4 and 10) was evaluated in a mouse thigh infection model of *Klebsiella pneumoniae* ATCC10031, using Colistin (Polymyxin E) as comparator. The results are summarized in Table 11B. The compounds 1, 4 and 10 at 10 mg/kg/day demonstrated an efficacy comparable to that of Colistin with approx. 2 $log_{10}$ reduction in bacterial counts.

TABLE 11B

In vivo efficacy versus *K.pneumoniae* ATCC10031 thigh infections in Neutropenic Mice.

| Example | Total daily dosage (mg/Kg) | Mean $log_{10}$ CFU reduction vs. control |
|---|---|---|
| Colistin | 10 | 2.60 |
| 1 | 10 | 2.22 |
| 4 | 10 | 1.92 |
| 10 | 10 | 2.30 |

The doses in the table are indicated in mg sulfate salt/kg.

Additional Biological Activity

In Vivo Efficacy Versus *E. coli* ATCC25922 Thigh Infection in Neutropenic Mice—Combination The in vivo efficacy of A1 was evaluated alone and in 1:1 (w:w) combination with rifampicin in a mouse thigh infection of *E. coli* 25922, using the same protocol as described for compounds 10 and 27 (Table 9), and using the dose levels indicated in Table 12. The results are summarised in Table 12

TABLE 12

In vivo efficacy versus *E. coli* ATCC25922 Thigh Infection in Neutropenic Mice

| Treatment | Dose (mg/kg) | Log reduction from vehicle (CFU/g) |
|---|---|---|
| Pre-treatment | NA | 3.31 |
| Vehicle | NA | 0.00 |
| A1 | 0.25 | 0.05 |
|  | 0.5 | −0.11 |
|  | 1 | −0.05 |
|  | 2 | 0.12 |
|  | 4 | 0.26 |
| A1/Rifampicin | 0.25/0.25 (0.5 total) | −0.11 |
|  | 0.5/0.5 (1 total) | 0.01 |
|  | 1/1 (2 total) | 1.46 |
|  | 2/2 (4 total) | 4.09 |
|  | 4/4 (8 total) | 4.91 |
| Polymyxin B/Rifampicin | 2/2 (4 total) | 4.80 |
| Polymyxin B | 4/0 (4 total) | 3.61 |

The doses in the table are indicated in mg sulfate salt/kg.

A1 in 1:1 combination with Rifampicin at 4 mg/Kg total dose gave a log reduction in bacterial counts of 4.09 compared to the non-treated control. Polymyxin B in 1:1 combination with Rifampicin at the same dose gave a 4.8 log reduction in bacterial counts.

In Vivo Efficacy Against *P. aeruginosa* ATCC 27853 Thigh Infection in Mice—Combination An in vivo efficacy study comparing Polymyxin B, Example 37 and Example 41 in 1:1 combination with Rifampicin was performed in a 9 hour thigh burden model of *P. aeruginosa* ATCC27853 infection in male CD1 mice. The results are summarized in Table 13.

In this study, 4 male mice were used in each compound treatment group and 6 for vehicle control. Mice were rendered temporarily neutropenic by immunosuppression with cyclophosphamide at 150 mg/kg 4 days before infection and 100 mg/kg 1 day before infection by intraperitoneal injection. 24 hours post the second round of immunosuppression, mice were infected with *P. aeruginosa* ATCC27853 intramuscularly into both lateral thigh muscles under inhaled anaesthesia using ~2.5 to 5×10$^5$ CFU/mouse thigh. Polymyxin B, Example 37 and Example 41 were administered at 0.25, 1 and 2.5 mg/kg in conjunction with Rifampicin at an equivalent dose. This gave total antibacterial levels of 0.5, 2 and 5 mg/kg for each combination (Table 1). Compounds were administered in solution by intravenous (IV) bolus injection into the lateral tail vein. This was performed three times at 1, 3.5 and 6 hours post infection at a dose volume of 10 mL/kg (0.25 mL/25 g mouse). The vehicle control group was treated with 0.9% saline for injection also at 10 mL/kg IV thrice at 1, 3.5 and 6 hours post infection.

At 1 hour post infection, 4 animals were humanely euthanized using pentabarbitone overdose to provide a pre-treatment control group. At 9 hours post infection, the clinical condition of all animals was assessed prior to them being humanely euthanized by pentabarbitone overdose. Animal weight was determined before both thighs were removed and weighed individually. Individual thigh tissue samples were homogenized in ice cold sterile phosphate buffered saline. Thigh homogenates were then quantitatively cultured onto CLED agar and incubated at 37° C. for 24 hours before colonies were counted.

TABLE 13

In vivo efficacy of compounds Example 37, Example 41 and Polymyxin versus *P. aeruginosa* ATCC27853 thigh infection in Neutropenic mice.

| Treatment | Dose (mg/kg) | Log reduction from vehicle (CFU/g) |
|---|---|---|
| Pre-treatment | NA | 2.23 |
| Vehicle | NA | — |
| Ex 37/Rifampicin | 0.25/0.25 (0.5 total) | 0.21 |
|  | 1/1 (2 total) | 1.42 |
|  | 2.5/2.5 (5 total) | 1.75 |
| Ex 41/Rifampicin | 0.25/0.25 (0.5 total) | 0.47 |
|  | 1/1 (2 total) | 1.03 |
|  | 2.5/2.5 (5 total) | 2.73 |
| Polymyxin B/Rifampicin | 0.25/0.25 (0.5 total) | 1.70 |
|  | 1/1 (2 total) | 1.04 |
|  | 2.5/2.5 (5 total) | 5.37 |

The doses in the table are indicated in mg sulfate salt/kg.

Example 37 tested 1:1 with rifampicin at a total dose of 5 mg/kg gave a 1.75 log reduction in bacterial counts compared to non-treated control, whereas Example 41:rifampicin gave a 2.73 log reduction, and Polymyxin B:rifampicin gave a 5.37 log reduction at the same dose level.

In Vivo Efficacy Against *P. aeruginosa* Thigh Infection in Mice—Mono Therapy

An in vivo efficacy study comparing two dose levels of Example 27, Example 38, Example 42, Example 47, Example 52 with Polymyxin B at three dose levels was performed in a 9 hour thigh burden model of *P. aeruginosa* ATCC 27853 infection in neutropenic male ICR mice, using the protocol described for Examples 37 and 41. Results are given in Table 14.

Example 27, Example 38, Example 42, Example 47 and Example 52 were administered at two doses (2 and 4 mg/kg). Three doses of Polymyxin B were used as comparator (1, 2 and 4 mg/kg). Compounds were administered in solution by intravenous (IV) bolus injection into the lateral tail vein. Treatment was administered three times at 1, 3.5 and 6 hours post infection at a dose volume of 10 mL/kg (0.25 mL/25 g mouse). The vehicle control group was treated with 0.9% saline for injection also at 10 mL/kg IV thrice at 1, 3.5 and 6 hours post infection.

TABLE 14

| Treatment | Dose (mg/kg) | Log reduction from vehicle (CFU/g) |
|---|---|---|
| Pre-treatment | NA | 2.22 |
| Vehicle | NA | 0.00 |
| Ex 27 | 2 | 0.24 |
|  | 4 | −0.58 |
| Ex 38 | 2 | −0.37 |
|  | 4 | 4.94 |

TABLE 14-continued

| Treatment | Dose (mg/kg) | Log reduction from vehicle (CFU/g) |
|---|---|---|
| Ex 42 | 2 | −0.03 |
|  | 4 | −0.28 |
| Ex 47 | 2 | −0.09 |
|  | 4 | 1.07 |
| Ex 52 | 2 | −0.14 |
|  | 4 | −0.18 |
| Polymyxin B | 1 | 0.58 |
|  | 2 | 1.67 |
|  | 4 | 5.09 |

The doses in the table are indicated in mg sulfate salt/kg.

Example 27, Example 42, and Example 52 at 2 or 4 mg/kg did not reduce thigh burdens significantly. Example 38, Example 47 did not affect thigh burdens significantly when administered at 2 mg/kg, but reduced burdens by 4.9 and 1.1 $Log_{10}$ CFU/g, respectively, when administered at 4 mg/kg.

A further in vivo efficacy study comparing two dose levels using Example 28, Example 39, and A3, and Polymyxin B at three dose levels was performed in a 9 hour thigh burden model of *P. aeruginosa* ATCC 27853 infection in neutropenic male ICR mice, using the protocol described for Examples 37 and 41. Results are given in Table 15.

TABLE 15

| Treatment | Dose (mg/kg) | Log reduction from vehicle (CFU/g) |
|---|---|---|
| Pre-treatment | NA | 1.79 |
| Vehicle | NA | 0.00 |
| Ex 28 | 2 | −0.38 |
|  | 4 | 0.20 |
| Ex 39 | 2 | 2.56 |
|  | 4 | 3.88 |
| A3 | 2 | 0.12 |
|  | 4 | 3.34 |
| Polymyxin B | 1 | −0.12 |
|  | 2 | 1.40 |
|  | 4 | 3.41 |

The doses in the table are indicated in mg sulfate salt/kg.

An in vivo efficacy study comparing A33 at 1.7 mg/Kg and 3.4 mg/kg free base equivalent with Polymyxin sulphate at 0.85, 1.7 and 3.4 mg/kg free base equivalent was performed in a 9 hour thigh burden model of *P. aeruginosa* ATCC 27853. The protocol was as described for Examples 37 and 41, except that the infection level was ~1×10⁴ CFU/mouse thigh. Results are given in Table 16.

TABLE 16

| Treatment | Dose (mg/kg) | Log reduction from vehicle (CFU/g) |
|---|---|---|
| Pre-treatment |  | 1.89 |
| Vehicle |  | 0.00 |

TABLE 16-continued

| Treatment | Dose (mg/kg) | Log reduction from vehicle (CFU/g) |
|---|---|---|
| A33 | 1.7 | 3.05 |
|  | 3.4 | 3.54 |
| Polymyxin B | 0.85 | 1.19 |
|  | 1.7 | 4.04 |
|  | 3.4 | 4.23 |

Dose in the table above refers to the free base equivalent.

Example A33 gave >3 log reduction in bacterial counts compared to non treated control, at both dose levels.

Effect of Hydroxyl and Amino Group Substituents on HK-2 Cell Toxicity

Example compounds were compared with a comparative example compound, C6, to show the benefits of hydroxyl and amino functionality in reducing HK-2 toxicity. Example compounds 1, 13 and A33 have significantly increased recorded $IC_{50}$ values against HK-2 compared with PMB. Whilst comparator compound C6 has reduced toxicity against HK-2 compared with PMB, the reduction is not as significant as that recorded for compounds 1, 13 and A33.

TABLE 17

Comparison of effect of hydroxyl and amino substituents on HK-2 Toxicity

| Example | $R_2$ | $R_3$ | $R_8$ | n | HK-2 relative to PMB |
|---|---|---|---|---|---|
| C6 | H | H | H | 1 | 3.3 |
| 1 | OH | H | H | 1 | 6.4 |
| A33 | H | $NH_2$ | H | 1 | 9.7 |
| 13 | H | H | $NH_2$ | 0 | 14 |

Additional Combination Activity

Further MIC tests were performed on example compounds 40 and 41 in the presence of Rifampicin against a panel of strains enriched for resistance to colistin or polymyxin B. MICs were determined in in line with CLSI susceptibility testing standards, in Cation-adjusted Mueller-Hinton broth II (Becton Dickinson). The data is set out in Table 18.

MICs (μg/mL) are reported as the total drug concentration for a 1:1 wt to wt combination of the example compound with Rifampicin. For example, a well at 2 μg/mL consisted of 1 μg/mL test compound and 1 μg/mL rifampicin.

TABLE 18

MIC values (micrograms/mL) for Polymyxin B alone, rifampicin alone, and for Polymyxin B and Example Compounds in a 1:1 combination with rifampicin

| Organism | Polymyxin B sulphate | Rifampicin | Example 40/ Rifampicin | Example 41/ Rifampicin | Polymyxin B/ Rifampicin |
|---|---|---|---|---|---|
| *Escherichia coli* (n = 9) | 1, 2, 2, 2, 8, 2, 8, 4, 8 | 16, 32, 8, 16, 16, 16, 16, 16, 16 | 0.25, 0.5, 0.5, 0.5, 2, 2, 8, 8, 8 | 0.25, 0.25, 0.25, 0.5, 2, 2, 4, 4, 4 | 2, 2, 2, 4, 2,4, 4, 4, 4 |

TABLE 18-continued

MIC values (micrograms/mL) for Polymyxin B alone, rifampicin alone, and for Polymyxin B and Example Compounds in a 1:1 combination with rifampicin

| Organism | Polymyxin B sulphate | Rifampicin | Example 40/ Rifampicin | Example 41/ Rifampicin | Polymyxin B/ Rifampicin |
|---|---|---|---|---|---|
| Klebsiella pneumoniae (n = 11) | 2, >32, 32, 4, 2, 2, 8, 8, 16, 32, >32 | 16, 32, >32, >32, 32, 32, 32, 32, >32, >32, >32 | 0.5, 0.5, 2, >32, >32, 0.5, 2, 4, 4, 16, >32 | 0.25, 0.5, 2, >32, >32, 0.5, 1, 2, 1, 4, 8 | 2, 4, 4, 16, 8, 4, 2, 4, 4, 4, 8 |
| Pseudomonas aeruginosa (n = 6) | 2, 2, 4, 8, >32, 16 | 32, 32, 16, 32, 32, 32 | 2, 2, 2, 4, 16, 16 | 2, 2, 2, 4, 8, 8 | 4, 4, 4, 8, 8, 8 |
| Acinetobacter baumanii (n = 8) | 4, 16, 32, 16, 16, 8, 16, >32 | 8, 4, 4, 2, 4, 4, 8, 8 | 2, 2, 2, 1, 2, 2, 2, 4, | 1, 1, 2, 1, 2, 2, 1, 2 | 2, 2, 2, 2, 4, 4, 2, 4 | where n indicates the number of strains within the panel for a particular organism.

In combination with rifampicin the example compounds have improved activity compared with polymyxin B against strains of E. coli, P. aeruginosa, K. pneumoniae and A. baumannii. The panel of organisms included resistant strains.

REFERENCES

All documents mentioned in this specification are incorporated herein by reference in their entirety.

de Visser et al, *J. Peptide Res*, 61, 2003, 298-306
Diaz et al. Syn Comm, 2008, 38, 2799
GCC 2012/22819
Handbook of Pharmaceutical Excipients, 5th edition, 2005
Katsuma et al. Chem. Pharm. Bull. 2009; 57, 332-336
Magee at al, *J. Med. Chem.*, 2013, 56, 5079
PCT/GB2012/052844
Petrosillo et al. Clin. Microbiol. Infect. 2008; 14, 816-827
Quale et al. *Microb. Drug Resist.* 2012; 18, 132-136
Remington's Pharmaceutical Sciences, 18th edition, Mack Publishing Company, Easton, Pa., 1990
Sato et al. Chem. Pharm. Bull. 2011; 59, 597-602
TW 101142961
U.S. Pat. No. 5,565,423
U.S. Pat. No. 8,415,307
Vaara et al, *Antimicrob. Agents and Chemotherapy*, 52, 2008. 3229-3236
Vaara et al. Microbiol. Rev. 1992; 56, 395-411
WO 1988/00950
WO 2008/017734
WO 2010/075416
WO 2012/168820
Yamada et al, *J. Peptide Res.* 64, 2004, 43-50
Yousef et al., Antimicrob. Agents Chemother. 2011, 55, 4044-4049

The invention claimed is:
1. A polymyxin compound, of formula (II) represented by:

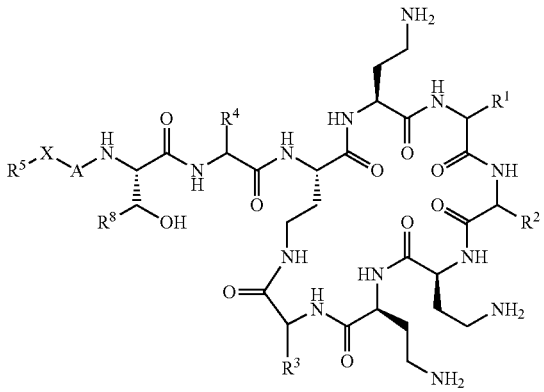

and pharmaceutically acceptable salts thereof, where:
—X— is —C(O)—, —NHC(O)—, —OC(O)—, —CH$_2$— or —SO$_2$—;
—R$^1$ together with the carbonyl group and nitrogen alpha to the carbon to which it is attached, is a phenylalanine, leucine or valine residue;
—R$^2$ together with the carbonyl group and nitrogen alpha to the carbon to which it is attached, is a leucine, threonine, iso-leucine, phenylalanine, valine or nor-valine residue;
—R$^3$ together with the carbonyl group and nitrogen alpha to the carbon to which it is attached, is a threonine or leucine residue;
each R$^6$ is independently hydrogen or C$_{1-4}$alkyl;
each R$^7$ is independently hydrogen or C$_{1-4}$alkyl;
—R$^8$ is methyl or hydrogen,
and wherein one of conditions (a), (b), (c), (d), (e) or (f) is met:
(a)
—R$^4$ is C$_{1-6}$ alkyl substituted with one hydroxyl group or one amino group;
-A- is a covalent bond or an amino acid; and
—R$^5$ is G-L$^2$-L$^1$-,
—G is C$_{5-12}$ aryl, where the C$_{5-12}$ aryl is optionally substituted one or more substituents selected from the group consisting of C$_{1-10}$ alkyl, halo, —CN, —NO$_2$, —CF$_3$, —NR$^{10}$C(O)R$^{10}$, —OCF$_3$, —CON(R$^{10}$)$_2$, —COOR$^9$, —OCOR$^{10}$, —NR$^{10}$COOR$^{10}$, —OCON(R$^{10}$)$_2$, —NR$^{10}$CON(R$^{10}$)$_2$, —OR$^9$, —SR$^9$, —NR$^{10}$SO$_2$R$^{10}$, —SO$_2$N(R$^{10}$)$_2$ and —SO$_2$R$^{10}$ where each —$R^9$ is independently $C_{1-10}$ alkyl and each —$R^{10}$ is independently —H or $C_{1-10}$ alkyl;
$L^1$- is a covalent bond, $C_{1-12}$ alkylene or $C_{2-12}$ heteroalkylene,
$L^2$- is a covalent bond or $C_{4-10}$ heterocyclylene,
—$R^5$ is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene;

(b)
—$R^4$ is $C_{1-6}$ alkyl substituted with one hydroxyl group or one amino group;
-A- is a covalent bond or an amino acid; and
—$R^5$ is G-$L^2$-$L^1$-, and -G is $C_{3-10}$ cycloalkyl,
$L^1$- is a covalent bond, $C_{1-12}$ alkylene or $C_{2-10}$ heteroalkylene,
$L^2$- is a covalent bond or $C_{4-12}$ heterocyclylene,
with the proviso that -$L^2$- is a covalent bond only when -$L^1$- is $C_{2-10}$ heteroalkylene,
—$R^5$ is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene;

(c)
—$R^4$ is $C_{1-6}$ alkyl substituted with one hydroxyl group or one amino group;
-A- is a covalent bond or an amino acid; and
(I) —$R^5$ is G-$L^2$-$L^1$-, where -G is $C_{3-10}$ cycloalkyl or $C_{2-12}$ alkyl,
-$L^1$- is a covalent bond or $C_{1-12}$ alkylene,
-$L^2$- is a covalent bond,
with the proviso that -$L^1$- is not $C_{1-12}$ alkylene when -G is $C_{2-12}$ alkyl, and —$R^5$ is substituted with:
two groups —$NR^6R^7$, and one, two or three hydroxyl groups; or
(II) —$R^5$ is G-$L^2$-$L^1$-, where -G is $C_{3-10}$ cycloalkyl or $C_{6-12}$ alkyl,
-$L^1$- is a covalent bond or $C_{1-12}$ alkylene,
-$L^2$- is a covalent bond,
with the proviso that -$L^1$- is not $C_{1-12}$ alkylene when -G is $C_{2-12}$ alkyl, and —$R^5$ is substituted with two or three groups —$NR^6R^7$ (d)
—$R^4$ is $C_{1-6}$ alkyl substituted with one hydroxyl group or one amino group;
-A- is a covalent bond or an amino acid;
—$R^5$ is D-$L^1$-, where D-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups;
-D is $C_{4-10}$ heterocyclyl;
-$L^1$- is a covalent bond, $C_{1-12}$ alkylene or $C_{2-12}$ heteroalkylene,
with the proviso that (i), (ii) and (iii) are optional substituents when -$L^1$- is a nitrogen-containing $C_{2-12}$ heteroalkylene;

(e)
—$R^4$ is $C_{1-6}$ alkyl substituted with one hydroxyl group or one amino group;
-A- is an amino acid; and
—$R^5$ is G-$L^2$-$L^1$-;
-G is $C_{2-12}$ alkyl, $C_{5-12}$ aryl or $C_{3-10}$ cycloalkyl;
-$L^1$- is a covalent bond, $C_{1-12}$ alkylene or $C_{2-12}$ heteroalkylene;
-$L^2$- is a covalent bond or $C_{4-10}$ heterocyclylene,
with the proviso that:
-$L^1$- is not $C_{1-12}$ alkylene when -G is $C_{2-12}$ alkyl, and G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene; or
—$R^5$ is D-$L^1$-, where -D is $C_{4-10}$ heterocyclyl and -$L^1$- is as defined above, and D-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -D is a nitrogen-containing $C_{4-10}$ heterocyclyl; and (f)
—$R^4$ is $C_1$alkyl substituted with one amino group or $C_{3-6}$ alkyl substituted with one amino group;
-A- is a covalent bond or an amino acid; and
(I) —$R^5$ is G-$L^2$-$L^1$-;
-G is $C_{2-12}$ alkyl, $C_{5-12}$ aryl or $C_{3-10}$ cycloalkyl;
-$L^1$- is a covalent bond, $C_{1-12}$ alkylene or $C_{2-12}$ heteroalkylene;
-$L^2$- is a covalent bond or $C_{4-10}$ heterocyclylene,
with the proviso that:
-$L^1$- is not $C_{1-12}$ alkylene when -G is $C_{2-12}$ alkyl, and G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$heteroalkylene and/or -$L^2$- is a nitrogen-containing $C_{4-10}$heterocyclylene; or
(II) —$R^5$ is D-$L^1$-, where -D is $C_{4-10}$ heterocyclyl and is as defined above, and D-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -D is a nitrogen-containing $C_{4-10}$ heterocyclyl.

2. A pharmaceutical composition comprising a compound or a pharmaceutically acceptable salt thereof of claim 1 and a biologically acceptable excipient, optionally together with a second active agent.

3. The compound or a pharmaceutically acceptable salt thereof according to claim 1, wherein the compound is a compound in which condition (a) or condition (f) is met.

4. The compound or a pharmaceutically acceptable salt thereof of claim 3, wherein
condition (f) is met and
—$R^5$ is G-$L^2$-$L^1$-;
  -G is $C_{2-12}$ alkyl, $C_{5-12}$ aryl or $C_{3-10}$ cycloalkyl;
  -$L^1$- is a covalent bond, $C_{1-12}$ alkylene or $C_{2-12}$ heteroalkylene;
  -$L^2$- is a covalent bond or $C_{4-10}$ heterocyclylene,
  with the proviso that:
  -$L^1$- is not $C_{1-12}$ alkylene when -G is $C_{2-12}$ alkyl, and G-$L^2$-$L^1$- is substituted with:
    (i) one, two or three hydroxyl groups, or
    (ii) one, two or three groups —$NR^6R^7$, or
    (iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene.

5. The compound or a pharmaceutically acceptable salt thereof of claim 4, wherein
—$R^5$ is G-$L^2$-$L^1$-; -G is $C_{2-12}$ alkyl;
and G-$L^2$-$L^1$- is substituted with:
  (i) one, two or three hydroxyl groups, or
  (ii) one, two or three groups —$NR^6R^7$, or
  (iii) one or two groups —$NR^6R^7$, and one, two or three hydroxyl groups.

6. The compound or a pharmaceutically acceptable salt thereof of claim 5, wherein
—$R^5$ is G-$L^2$-$L^1$-;
-G is $C_{2-12}$ alkyl; and
G-$L^2$-$L^1$- is substituted with: (ii) one, two or three groups —$NR^6R^7$.

7. The compound or a pharmaceutically acceptable salt thereof, of claim 1, wherein the compound is:

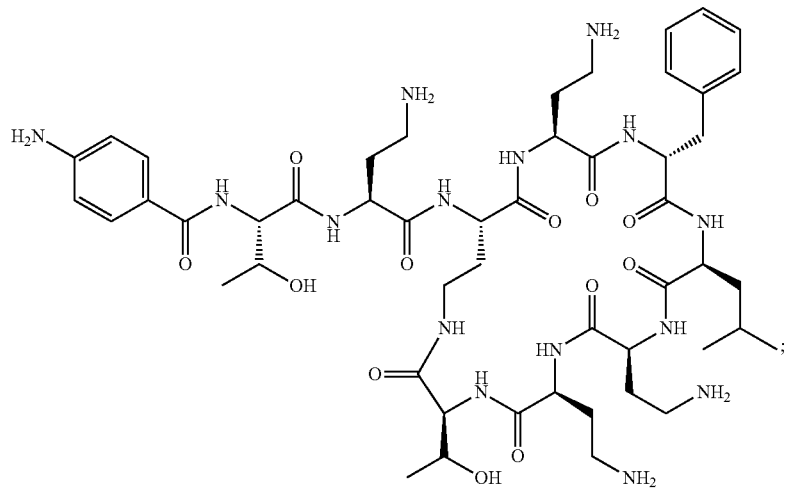

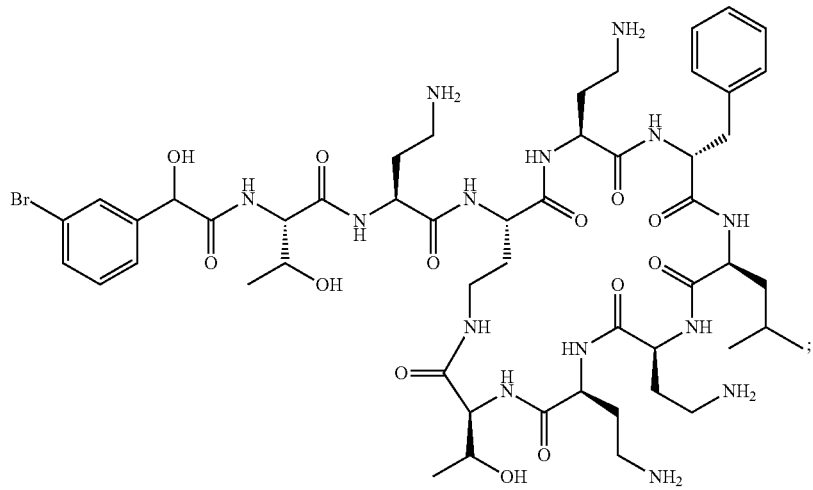

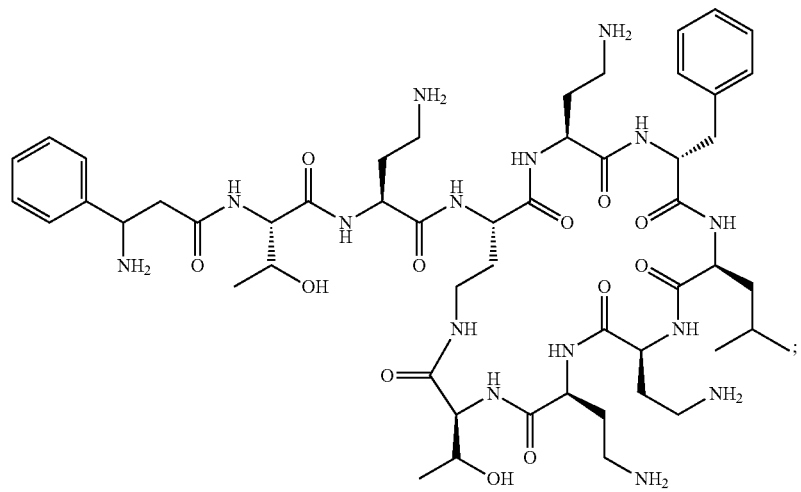
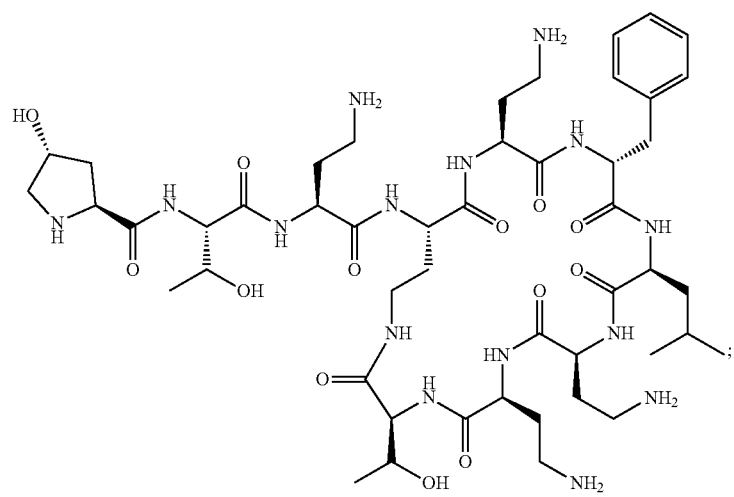
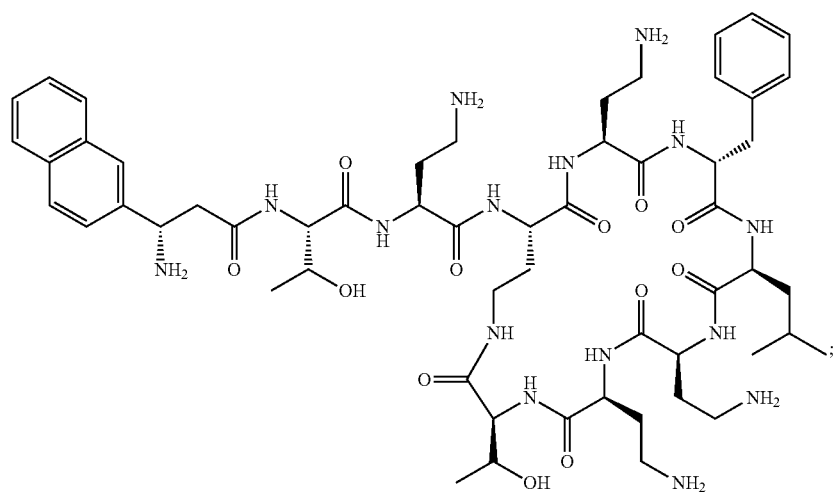

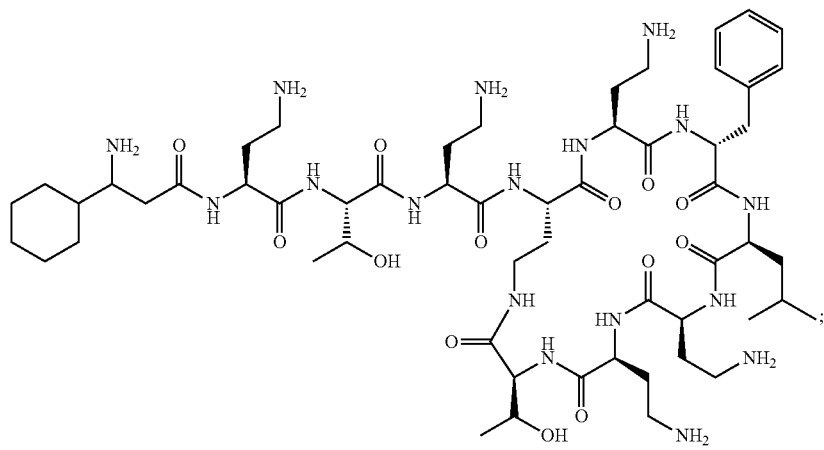
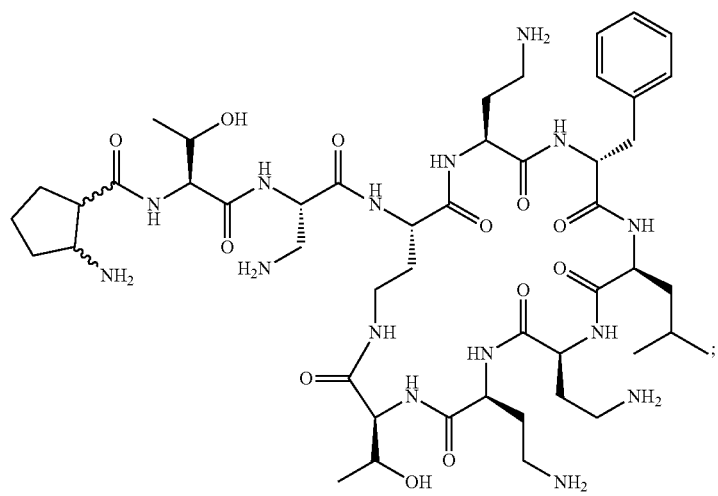
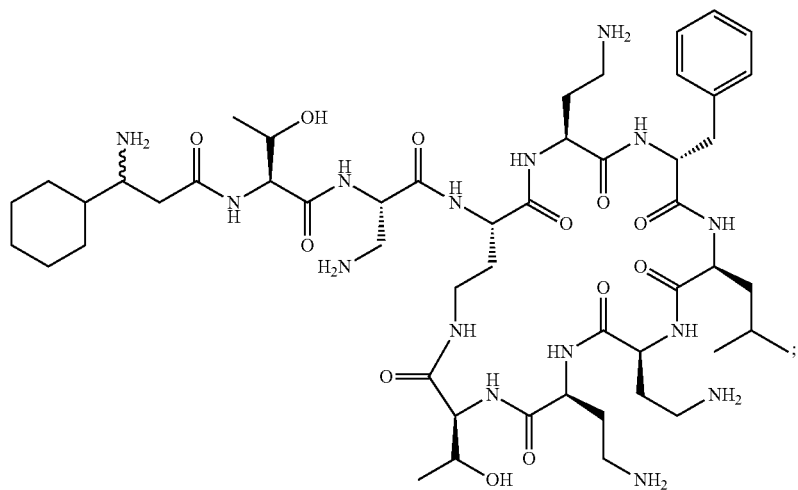

-continued
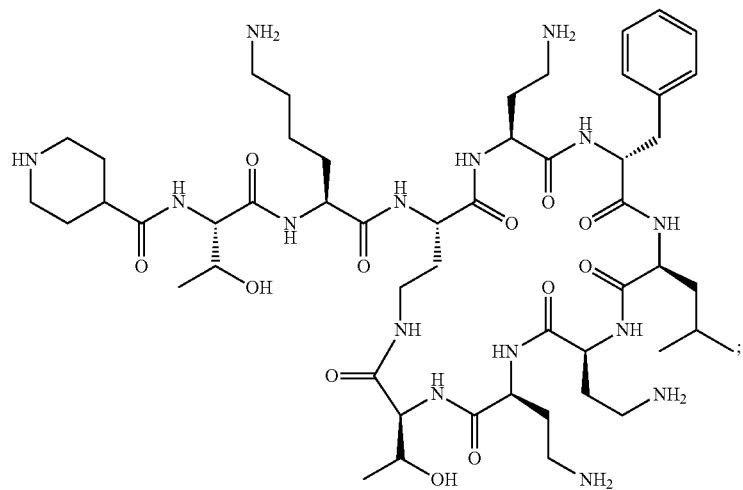
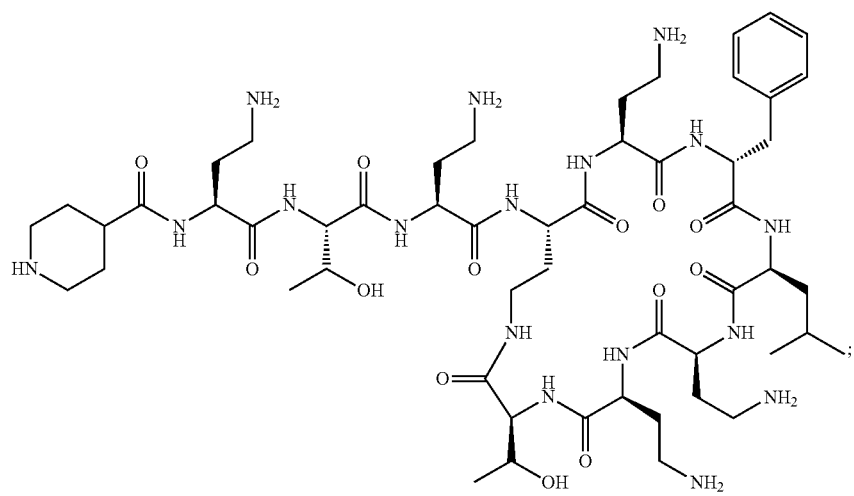
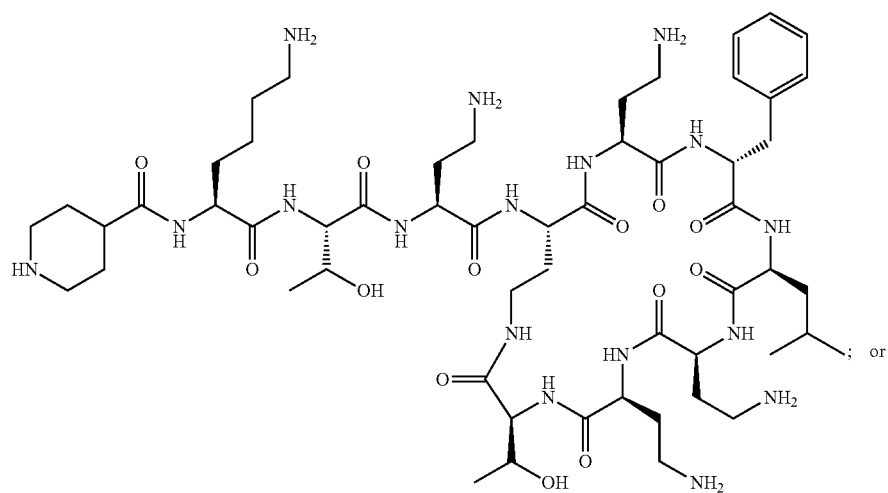

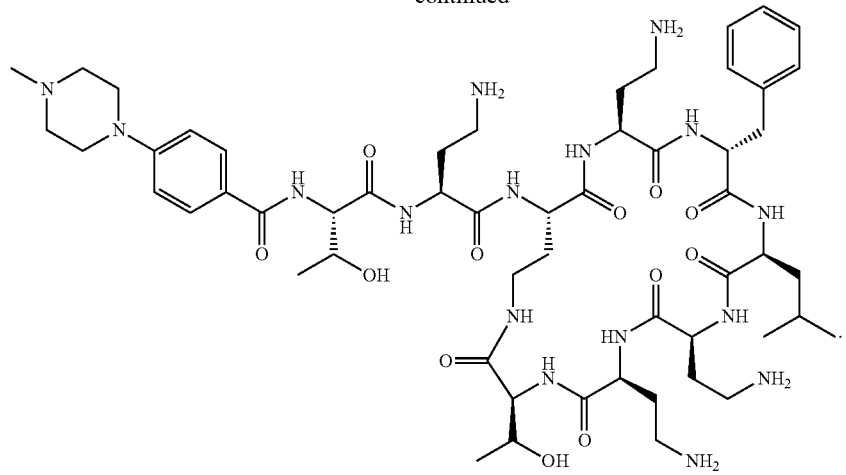

8. The compound or a pharmaceutically acceptable salt thereof of claim 1, wherein —X— is —C(O)—.

9. The compound or a pharmaceutically acceptable salt thereof of claim 1, wherein —$R^1$ together with the carbonyl group and nitrogen alpha to the carbon to which it is attached, is a phenylalanine residue or a leucine residue;
- —$R^2$ together with the carbonyl group and nitrogen alpha to the carbon to which it is attached, is leucine or threonine residue;
- —$R^3$ together with the carbonyl group and nitrogen alpha to the carbon to which it is attached, is a threonine residue; and
- —$R^8$ is methyl.

10. The compound or a pharmaceutically acceptable salt thereof of claim 1, wherein -A- is a covalent bond.

11. The compound or a pharmaceutically acceptable salt thereof of claim 1, wherein -A- is an amino acid.

12. The compound or a pharmaceutically acceptable salt thereof of claim 1, wherein —$R^5$ is G-$L^2$-$L^1$-.

13. The compound or a pharmaceutically acceptable salt thereof of claim 12, wherein
- -$L^1$- is a covalent bond or a $C_{1-12}$ alkylene group; and/or
- -$L^2$- is a covalent bond.

14. The compound or a pharmaceutically acceptable salt thereof of claim 1, wherein
- -G is $C_{2-12}$ alkyl.

15. The compound or a pharmaceutically acceptable salt thereof of claim 1, wherein -G is $C_{3-10}$ cycloalkyl.

16. The compound or a pharmaceutically acceptable salt thereof of claim 1, wherein -G is $C_{5-12}$ aryl.

17. The compound or a pharmaceutically acceptable salt thereof of claim 1,
- G-$L^2$-$L^1$- is substituted with:
  (i) one, two or three hydroxyl groups, or
  (ii) one, two or three groups —$NR^6R^7$, or
  (iii) one or two groups —$NR^6R^7$, and one, two or three hydroxyl groups.

18. The compound or a pharmaceutically acceptable salt thereof of claim 1, wherein —$R^5$ is D-$L^1$-.

19. The compound or a pharmaceutically acceptable salt thereof of claim 1, wherein -D is a nitrogen-containing heterocyclyl group.

20. The compound or a pharmaceutically acceptable salt thereof of claim 1, represented by the formula

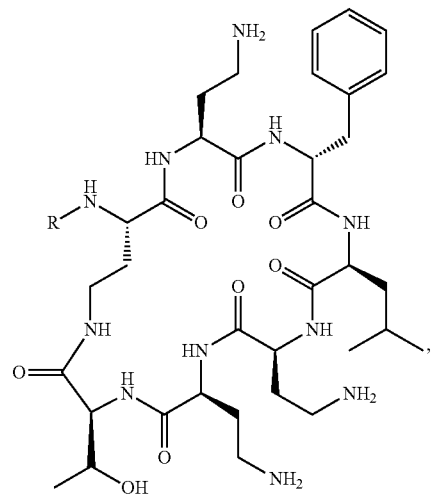

wherein R is

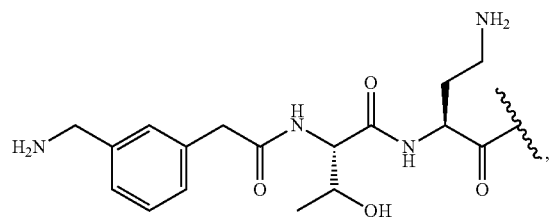

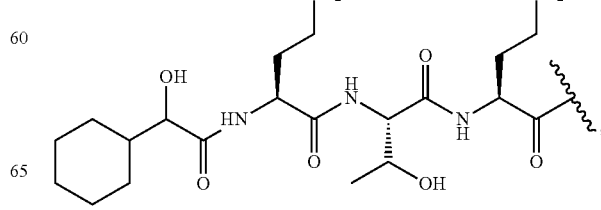

189
-continued
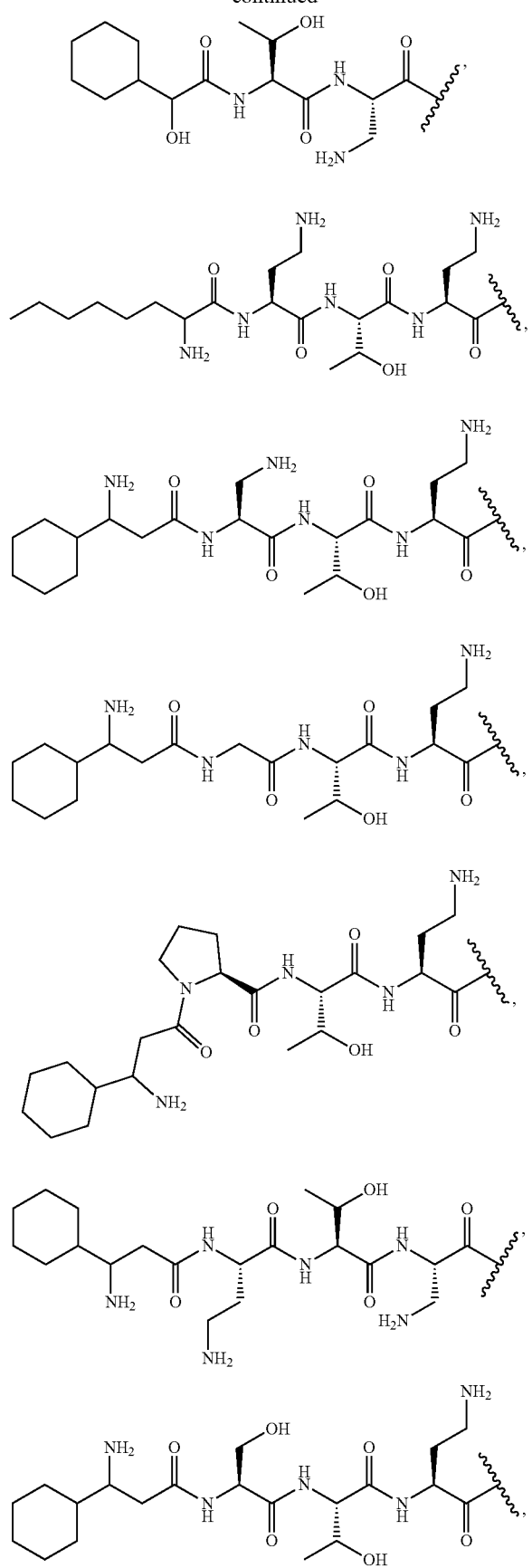
190
-continued
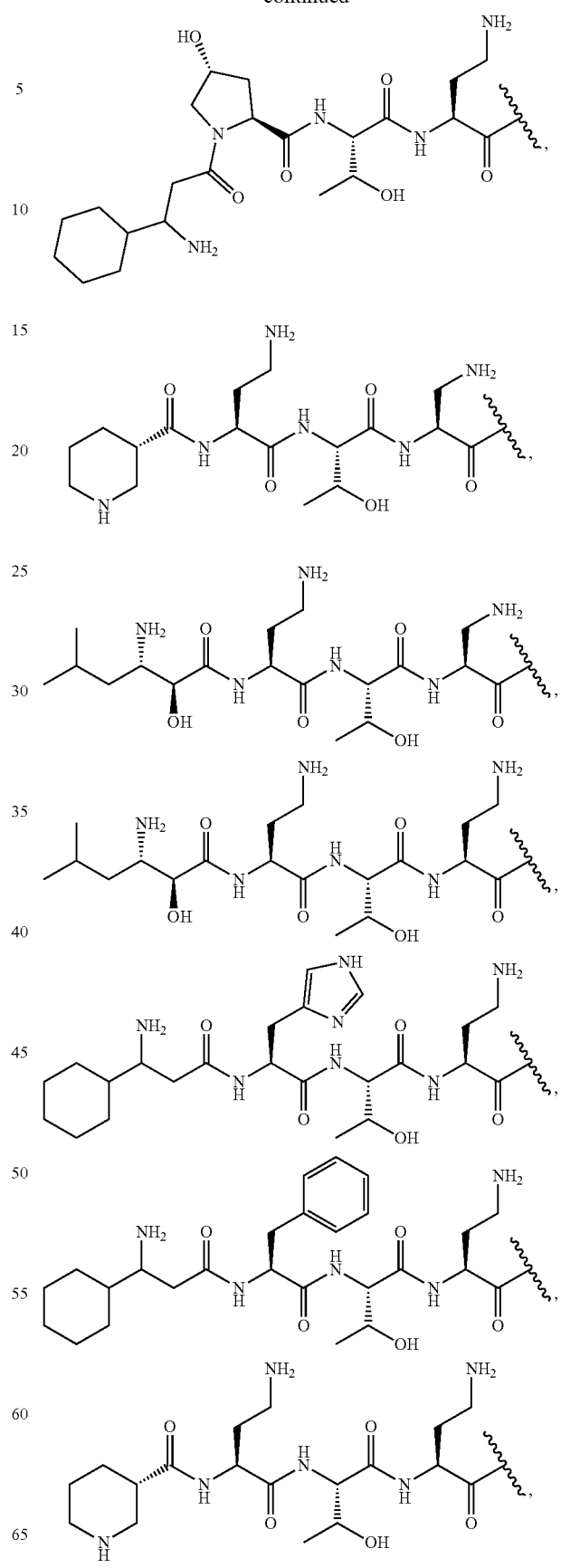

-continued

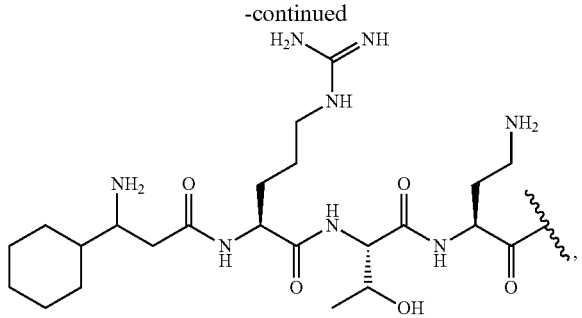

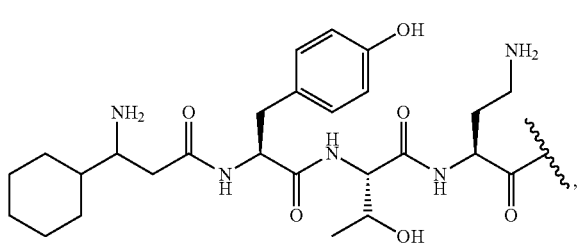

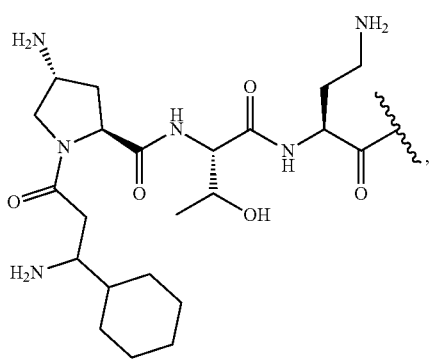

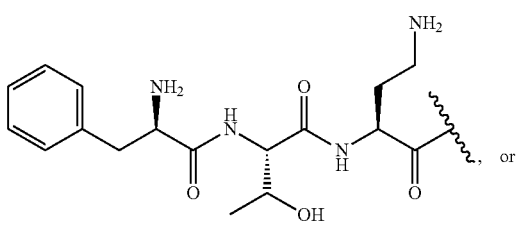, or

-continued

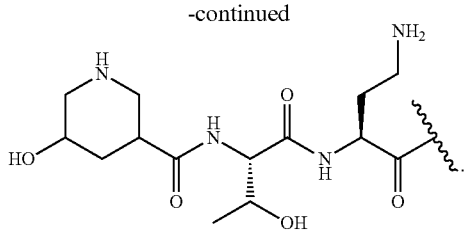

21. A pharmaceutical composition comprising a compound or a pharmaceutically acceptable salt thereof of claim 1 together with a second active agent and a biologically acceptable excipient.

22. A method of treating a Gram negative bacterial infection, the method comprising administering to a subject in need thereof a polymyxin compound and an active agent,
wherein the active agent is selected from the group consisting of: rifampicin, rifabutin, rifalazil, rifapentine, rifaximin, oxacillin, methicillin, ampicillin, cloxacillin, carbenicillin, piperacillin, tricarcillin, flucloxacillin, nafcillin, azithromycin, clarithromycin, erythromycin, telithromycin, cethromycin, solithromycin, aztreonam, BAL30072, meropenem, doripenem, imipenem, ertapenem, biapenem, tomopenem, panipenem, tigecycline, omadacycline, eravacycline, doxycycline, minocycline, ciprofloxacin, levofloxacin, moxifloxacin, delafloxacin, fusidic acid, novobiocin, teichoplanin, telavancin, dalbavancin, and oritavancin, and pharmaceutically acceptable salts thereof; and
the polymyxin compound is a compound of claim 1.

23. The method according to claim 1, wherein the active agent is selected from the group consisting of rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts thereof.

24. A method of treating a Gram negative bacterial infection, the method comprising the step of administering to a subject in need thereof a polymyxin compound or a pharmaceutically acceptable salt thereof of claim 1.

25. A method of treating a Gram negative bacterial infection, wherein the method comprises administering to a subject in need thereof a polymyxin compound or a pharmaceutically acceptable salt thereof of claim 1 and an active agent selected from the group consisting of rifampicin, fusidic acid, novobiocin, oxacillin, azithromycin, aztreonam, meropenem, tigecycline, and ciprofloxacin, and pharmaceutically acceptable salts thereof.

\* \* \* \* \*